US007309597B2

(12) United States Patent
Liao et al.

(10) Patent No.: US 7,309,597 B2
(45) Date of Patent: Dec. 18, 2007

(54) ALANINE 2,3-AMINOMUTASE

(75) Inventors: Hans H. Liao, Eden Prairie, MN (US); Ravi R. Gokarn, Minneapolis, MN (US); Steven J. Gort, Brooklyn Center, MN (US); Holly J. Jessen, Chanhassen, MN (US); Olga Selifonova, Plymouth, MN (US)

(73) Assignee: Cargill, Incorporated, Wayzata, MN (US)

( * ) Notice: Subject to any disclaimer, the term of this patent is extended or adjusted under 35 U.S.C. 154(b) by 323 days.

(21) Appl. No.: 10/502,040

(22) PCT Filed: Jan. 17, 2003

(86) PCT No.: PCT/US03/01635

§ 371 (c)(1),
(2), (4) Date: Jul. 19, 2004

(87) PCT Pub. No.: WO03/062173

PCT Pub. Date: Jul. 31, 2003

(65) Prior Publication Data

US 2005/0221466 A1 Oct. 6, 2005

Related U.S. Application Data

(60) Provisional application No. 60/375,785, filed on Apr. 25, 2002, provisional application No. 60/350,727, filed on Jan. 18, 2002.

(51) Int. Cl.

| | |
|---|---|
| ***C12N 9/90*** | (2006.01) |
| ***C12N 1/19*** | (2006.01) |
| ***C12N 1/21*** | (2006.01) |
| ***C12N 5/04*** | (2006.01) |
| ***C12N 15/63*** | (2006.01) |
| ***C07H 21/04*** | (2006.01) |
| ***A01H 1/00*** | (2006.01) |

(52) U.S. Cl. .............. 435/233; 435/252.3; 435/254.11; 435/320.1; 435/410; 536/23.2; 800/278

(58) Field of Classification Search ..................... None
See application file for complete search history.

(56) References Cited

U.S. PATENT DOCUMENTS

| | | | |
|---|---|---|---|
| 6,136,576 | A | 10/2000 | Diaz-Torres et al. |
| 6,177,264 | B1 | 1/2001 | Eggeling et al. |
| 6,184,006 | B1 | 2/2001 | Rieping et al. |
| 6,248,874 | B1 | 6/2001 | Frey et al. |
| 2002/0173637 | A1 | 11/2002 | Frey et al. |
| 2003/0113882 | A1 | 6/2003 | Frey et al. |

FOREIGN PATENT DOCUMENTS

| | | |
|---|---|---|
| WO | WO 01/16346 | 3/2001 |
| WO | WO 01/21771 A2 | 3/2001 |
| WO | WO 02/42418 | 5/2002 |
| WO | WO 2006/047589 A2 | 5/2006 |

OTHER PUBLICATIONS

Begley et al., "The Biosynthesis of Coenzyme A in Bacteria," *Vitam. Horm. 61*:157-171 (2001).

Cronan, "β-Alanine Synthesis in *Escherichia coli*," *J. Bacteriol. 141*:1291-1297 (1980).

Dusch et al., "Expression of *Corynebacterium glutamicum panD* Gene Encoding L-Aspartate-α-Decarboxylase Leads to Pantothenate Overproduction in *Escherichia coli*," *Appl. Environ. Microbiol. 65*:1530-1539 (1999).

Ramjee et al., "*Escherichia coli* L-Aspartate-α-Decarboxylase: Preprotein Processing and Observation of Reaction Intermediates by Electrospray Mass Spectrometry," *Biochem. J. 323*:661-669 (1997).

*Primary Examiner*—Elizabeth Slobodyansky

(57) ABSTRACT

Alanine 2,3-aminomutase sequences are disclosed, as are cells having alanine 2,3-aminomutase activity and methods of selecting for such cells. Methods for producing beta-alanine, pantothenate, 3-hydroxypropionic acid, as well as other organic compounds, are disclosed.

35 Claims, 6 Drawing Sheets

FIG. 4

| | | |
|---|---|---|
| BSKam | 1 | mknkwykpkrhwkeielwkdvpeekwndwlwqlthtvrtlddlkkvinlt |
| MUTANT | 1 | mknkwykpkrhwkeielwkdvpeekwndwlwqlthtvrtlddlkkvinlt |
| BSKam | 51 | edeeegvristktiplnitpyyaslmdpdnprcpvrmqsvplseemhktk |
| MUTANT | 51 | edeeegvristktiplnitpyyaslmdpdnprcpvrmqsvplseemhktk |
| BSKam | 101 | yd**l**edplhededspvpglthrypdrvlflvtnq<u>cs**m**ycryctrrrf</u>sgqi |
| MUTANT | 101 | yd**m**edplhededspvpglthrypdrvlflvtnq<u>cs**v**ycryctrrrf</u>sgqi |
| BSKam | 151 | gmgvpkkqldaaiayiretpeirdclisggdgllindqileyilkelrsi |
| MUTANT | 151 | gmgvpkkqldaaiayiretpeirdclisggdgllindqileyilkelrsi |
| BSKam | 201 | phlevirigtrapvvfpqritdhlceilkkyhpvwlnthfntsiemtees |
| MUTANT | 201 | phlevirigtrapvvfpqritdhlceilkkyhpvwlnthfntsiemtees |
| BSKam | 251 | veaceklvnagvpvgnqavvlagindsvpimkklmhd*lvkirv*rpyyiyq |
| MUTANT | 251 | veaceklvnagvpvgnqavvlagindsvpimkklmhdlvkirvrpyyiyq |
| BSKam | 301 | cdlsegighfrapvskgleiieglrghtsgyavptfvv**d**apggggkialq |
| MUTANT | 301 | cdlsegighfrapvskgleiieglrghtsgyavptfvv**h**apggggkialq |
| BSKam | 351 | pnyvlsqspdkvilrnfegvitsypepenyipnqadayfesvfpetadkk |
| MUTANT | 351 | pnyvlsqspdkvilrnfegvitsypepenyipnqadayfesvfpetadkk |
| BSKam | 401 | epiglsaifadkevsftpenvdrikrreayianpehetlkdrrekrdqlk |
| MUTANT | 401 | epiglsaifadkevsftpenvdrikrreayianpehetlkdrrekrdqlk |
| BSKam | 451 | ekkflaqqkkqketecggdss |
| MUTANT | 451 | ekkflaqqkkqketecggdss |

FIG. 5

```
Pgkam     1 maesrrkyyfpdvtdeqwndwhwqvlnrietldqlkkyvtltaeeeegvk
Pgaam     1 maesrrkyyfpdvtdeqwydwhwqvlnrietldqlkkyvtltaeeeegvk

Pgkam    51 eslkvlrmaitpyylslidpenpncpirkqaipthqelvrapedqvdpls
Pgaam    51 espkvlrmaitpyylslidpenpncpirkqaiptqqelvrapedqvdpls

Pgkam   101 ededspvpglthrypdrvlflitdkcsmycrhctrrrfagqkdasspser
Pgaam   101 ededspvpglthrypdrvlflitdkcsmycrhctrrrfagqkdasspser

Pgkam   151 idrcidyiantptvrdvllsggdallvsderleyilkrlreiphveivri
Pgaam   151 idrcidyiantptvrdvllsggdallvsderleyilkrlreiphveivri

Pgkam   201 gsrtpvvlpqritpqlvdmlkkyhpvwlnthfnhpnevteeaveacerma
Pgaam   201 gsrtpvvlpqritpqlvdmlkkyhpvwlnthfnhpnevteeaveacerma

Pgkam   251 nagiplgnqtvllrgindcthvmkrlvhllvkmrvrpyyiyvcdlslgig
Pgaam   251 nagiplgnqtvllrgindcthvmkrlvhllvkmrvrpyyiyvcdlslgig

Pgkam   301 hfrtpvskgieiienlrghtsgyavptfvvdapggggkipvmpnyvvsqs
Pgaam   301 hfrtpvskgieiienlrghtsgyavptfvvgapggggkipvtpnyvvsqs

Pgkam   351 prhvvlrnyegvittytepenyheecdcedcragkhkegvaalsggqqla
Pgaam   351 prhvvlrnyegvittytepenyheecdcedcragkhkegvaalsggqqla

Pgkam   401 iepsdlarkkrkfdkn
Pgaam   401 iepsdlarkkrkfdkn
```

FIG. 6

| | | |
|---|---|---|
| Pgkam | 1 | maesrrkyyfp-----------dvtdeqwndwhwqvlnrietldqlkkyv |
| Pgaam | 1 | maesrrkyyfp-----------dvtdeqwydwhwqvlnrietldqlkkyv |
| Bskam | 1 | ---mknkwykpkrhwkeielwkdvpeekwndwlwqlthtvrtlddlkkvi |
| Bsaam | 1 | ---mknkwykpkrhwkeielwkdvpeekwndwlwqlthtvrtlddlkkvi |
| | | |
| Pgkam | 40 | tltaeeeegvkeslkvlrmaitpyylslidpenpncpirkqaipthqelv |
| Pgaam | 40 | tltaeeeegvkespkvlrmaitpyylslidpenpncpirkqaiptqqelv |
| Bskam | 48 | nltedeeegvristktiplnitpyyaslmdpdnprcpvrmqsvplseemh |
| Bsaam | 48 | nltedeeegvristktiplnitpyyaslmdpdnprcpvrmqsvplseemh |
| | | |
| Pgkam | 90 | rapedqvdplsededspvpglthrypdrvlflitdkcsmycrhctrrrfa |
| Pgaam | 90 | rapedqvdplsededspvpglthrypdrvlflitdkcsmycrhctrrrfa |
| Bskam | 98 | ktkydledplhededspvpglthrypdrvlflvtnqcsmycryctrrrfs |
| Bsaam | 98 | ktkydmedplhededspvpglthrypdrvlflvtnqcsvycryctrrrfs |
| | | |
| Pgkam | 140 | gqkdasspseridrcidyiantptvrdvllsggdallvsderleyilkrl |
| Pgaam | 140 | gqkdasspseridrcidyiantptvrdvllsggdallvsderleyilkrl |
| Bskam | 148 | gqigmgvpkkqldaaiayiretpeirdclisggdgllindqileyilkel |
| Bsaam | 148 | gqigmgvpkkqldaaiayiretpeirdclisggdgllindqileyilkel |
| | | |
| Pgkam | 190 | reiphveivrigsrtpvvlpqritpqlvdmlkkyhpvwlnthfnhpnevt |
| Pgaam | 190 | reiphveivrigsrtpvvlpqritpqlvdmlkkyhpvwlnthfnhpnevt |
| Bskam | 198 | rsiphlevirigtrapvvfpqritdhlceilkkyhpvwlnthfntsiemt |
| Bsaam | 198 | rsiphlevirigtrapvvfpqritdhlceilkkyhpvwlnthfntsiemt |
| | | |
| Pgkam | 240 | eeaveacermanagiplgnqtvllrgindcthvmkrlvhllvkmrvrpyy |
| Pgaam | 240 | eeaveacermanagiplgnqtvllrgindcthvmkrlvhllvkmrvrpyy |
| Bskam | 248 | eesveaceklvnagvpvgnqavvlagindsvpimkklmhdlvkirvrpyy |
| Bsaam | 248 | eesveaceklvnagvpvgnqavvlagindsvpimkklmhdlvkirvrpyy |
| | | |
| Pgkam | 290 | iyvcdlslgighfrtpvskgieiienlrghtsgyavptfvv**d**apggggki |
| Pgaam | 290 | iyvcdlslgighfrtpvskgieiienlrghtsgyavptfvv**g**apggggki |
| Bskam | 298 | iyqcdlsegighfrapvskgleiieglrghtsgyavptfvv**d**apggggki |
| Bsaam | 298 | iyqcdlsegighfrapvskgleiieglrghtsgyavptfvv**h**apggggki |
| | | |
| Pgkam | 340 | pvmpnyvvsqsprhvvlrnyegvittytepeny-------heecdcedcr |
| Pgaam | 340 | pvtpnyvvsqsprhvvlrnyegvittytepeny-------heecdcedcr |
| Bskam | 348 | alqpnyvlsqspdkvilrnfegvitsypepenyipnqadayfesvfpeta |
| Bsaam | 348 | alqpnyvlsqspdkvilrnfegvitsypepenyipnqadayfesvfpeta |
| | | |
| Pgkam | 383 | agkhkegvaalsggqqlaiepsdlar------------------------ |
| Pgaam | 383 | agkhkegvaalsggqqlaiepsdlar------------------------ |
| Bskam | 398 | dkkepiglsaifadkevsftpenvdrikrreayianpehetlkdrrekrd |
| Bsaam | 398 | dkkepiglsaifadkevsftpenvdrikrreayianpehetlkdrrekrd |
| | | |
| Pgkam | 409 | --kkrkf--------------dkn |
| Pgaam | 409 | --kkrkf--------------dkn |
| Bskam | 448 | qlkekkflaqqkkqketecggdss |
| Bsaam | 448 | qlkekkflaqqkkqketecggdss |

SEQUENCE LISTING

<160> NUMBER OF SEQ ID NOS: 66

<210> SEQ ID NO 1
<211> LENGTH: 40
<212> TYPE: DNA
<213> ORGANISM: Artificial Sequence
<220> FEATURE:
<223> OTHER INFORMATION: PCR primer

<400> SEQUENCE: 1
gcgcgaggag gagttcatat gaaaaacaaa tggtataaac          40

<210> SEQ ID NO 2
<211> LENGTH: 36
<212> TYPE: DNA
<213> ORGANISM: Artificial Sequence
<220> FEATURE:
<223> OTHER INFORMATION: PCR primer

<400> SEQUENCE: 2
cgggcaccgc ttcgaggcgg ccgcaccatt cgcatg              36

<210> SEQ ID NO 3
<211> LENGTH: 1416
<212> TYPE: DNA
<213> ORGANISM: Bacillus subtilis

<400> SEQUENCE: 3
ttgaaaaaca aatggtataa accgaaacgg cattggaagg agatcgagtt atggaaggac          60
gttccggaag agaaatggaa cgattggctt tggcagctga cacacactgt aagaacgtta         120
gatgatttaa agaaagtcat taatctgacc gaggatgaag aggaaggcgt cagaatttct         180
accaaaacga tccccttaaa tattacacct tactatgctt ctttaatgga ccccgacaat         240
ccgagatgcc cggtacgcat gcagtctgtg ccgctttctg aagaaatgca caaaacaaaa         300
tacgatctgg aagacccgct tcatgaggat gaagattcac cggtacccgg tctgacacac         360
cgctatcccg accgtgtgct gtttcttgtc acgaatcaat gttccatgta ctgccgctac         420
tgcacaagaa ggcgcttttc cggacaaatc ggaatgggcg tccccaaaaa acagcttgat         480

-continued

```
gctgcaattg cttatatccg ggaaacaccc gaaatccgcg attgtttaat ttcaggcggt    540

gatgggctgc tcatcaacga ccaaatttta gaatatattt taaaagagct gcgcagcatt    600

ccgcatctgg aagtcatcag aatcggaaca agagctcccg tcgtctttcc gcagcgcatt    660

accgatcatc tgtgcgagat attgaaaaaa tatcatccgg tctggctgaa cacccatttt    720

aacacaagca tcgaaatgac agaagaatcc gttgaggcat gtgaaaagct ggtgaacgcg    780

ggagtgccgg tcggaaatca ggctgtcgta ttagcaggta ttaatgattc ggttccaatt    840

atgaaaaagc tcatgcatga cttggtaaaa atcagagtcc gtccttatta tatttaccaa    900

tgtgatctgt cagaaggaat agggcatttc agagctcctg tttccaaagg tttggagatc    960

attgaagggc tgagaggtca tacctcaggc tatgcggttc ctacctttgt cgttgacgca   1020

ccaggcggag gaggtaaaat cgccctgcag ccaaactatg tcctgtcaca aagtcctgac   1080

aaagtgatct taagaaattt tgaaggtgtg attacgtcat atccggaacc agagaattat   1140

atccccaatc aggcagacgc ctattttgag tccgttttcc ctgaaaccgc tgacaaaaag   1200

gagccgatcg ggctgagtgc catttttgct gacaaagaag tttcgtttac acctgaaaat   1260

gtagacagaa tcaaaaggag agaggcatac atcgcaaatc cggagcatga aacattaaaa   1320

gatcggcgtg agaaaagaga tcagctcaaa gaaaagaaat ttttggcgca gcagaaaaaa   1380

cagaaagaga ctgaatgcgg aggggattct tcatga                             1416
```

<210> SEQ ID NO 4
<211> LENGTH: 60
<212> TYPE: DNA
<213> ORGANISM: Artificial Sequence
<220> FEATURE:
<223> OTHER INFORMATION: PCR primer

<400> SEQUENCE: 4

```
tatcaattcg ttacaggcga tacatggcac gcttcggcgc gtgtaggctg gagctgcttc     60
```

<210> SEQ ID NO 5
<211> LENGTH: 60
<212> TYPE: DNA
<213> ORGANISM: Artificial Sequence
<220> FEATURE:
<223> OTHER INFORMATION: PCR primer

<400> SEQUENCE: 5

```
gatgtcgcgg ctggtgagta accagccgca gggataacaa catatgaata tcctccttag     60
```

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6

```
ttaccgagca gcgttcagag                                                 20
```

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7

```
cacctggcgg tgacaaccat                                                 20
```

-continued

<210> SEQ ID NO 8
<211> LENGTH: 60
<212> TYPE: DNA
<213> ORGANISM: Artificial Sequence
<220> FEATURE:
<223> OTHER INFORMATION: PCR primer

<400> SEQUENCE: 8
gcggcgtgaa gtttcccaac ccgttctgcc tctcttcttc gtgtaggctg gagctgcttc 60

<210> SEQ ID NO 9
<211> LENGTH: 60
<212> TYPE: DNA
<213> ORGANISM: Artificial Sequence
<220> FEATURE:
<223> OTHER INFORMATION: PCR primer

<400> SEQUENCE: 9
ttacaacgtt accgggtgtt ctttctcgcc tttcttaaac catatgaata tcctccttag 60

<210> SEQ ID NO 10
<211> LENGTH: 51
<212> TYPE: DNA
<213> ORGANISM: Artificial Sequence
<220> FEATURE:
<223> OTHER INFORMATION: PCR primer

<400> SEQUENCE: 10
cacaaaacaa aatacgatat ggaagacccg ctccatgagg atgaagattc a 51

<210> SEQ ID NO 11
<211> LENGTH: 51
<212> TYPE: DNA
<213> ORGANISM: Artificial Sequence
<220> FEATURE:
<223> OTHER INFORMATION: PCR primer

<400> SEQUENCE: 11
tgaatcttca tcctcatgga gcgggtcttc catatcgtat tttgttttgt g 51

<210> SEQ ID NO 12
<211> LENGTH: 28
<212> TYPE: DNA
<213> ORGANISM: Artificial Sequence
<220> FEATURE:
<223> OTHER INFORMATION: PCR primer

<400> SEQUENCE: 12
gaatcaatgt tccgtatact gccgctac 28

<210> SEQ ID NO 13
<211> LENGTH: 28
<212> TYPE: DNA
<213> ORGANISM: Artificial Sequence
<220> FEATURE:
<223> OTHER INFORMATION: PCR primer

<400> SEQUENCE: 13
gtagcggcag tatacggaac attgattc 28

<210> SEQ ID NO 14
<211> LENGTH: 31
<212> TYPE: DNA
<213> ORGANISM: Artificial Sequence
<220> FEATURE:

-continued

<223> OTHER INFORMATION: PCR primer

<400> SEQUENCE: 14
gttcctacct ttgttgtaca cgcaccaggc g 31

<210> SEQ ID NO 15
<211> LENGTH: 31
<212> TYPE: DNA
<213> ORGANISM: Artificial Sequence
<220> FEATURE:
<223> OTHER INFORMATION: pcr primer

<400> SEQUENCE: 15
cgcctggtgc gtgtacaaca aaggtaggaa c 31

<210> SEQ ID NO 16
<211> LENGTH: 23
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)..(23)
<223> OTHER INFORMATION: y is t/u or c; s is g or c; b is g, c or t/u.

<400> SEQUENCE: 16
ttyatyggby tsggbaayat ggg 23

<210> SEQ ID NO 17
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)..(20)
<223> OTHER INFORMATION: y is t/u or c; s is g or c; b is g, c or t/u; w is a or t/u; n is a, c, g or t/u.

<400> SEQUENCE: 17
gaygcnccng tbwssggbgg 20

<210> SEQ ID NO 18
<211> LENGTH: 21
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)..(21)
<223> OTHER INFORMATION: y is t/u or c; r is g or a; n is a, c, g or t/u.

<400> SEQUENCE: 18
catrttrttr caratyttng c 21

<210> SEQ ID NO 19
<211> LENGTH: 27
<212> TYPE: DNA
<213> ORGANISM: Artificial Sequence
<220> FEATURE:
<223> OTHER INFORMATION: PCR primer

<400> SEQUENCE: 19
ggtttacgag ggcgagaacg gcttgct 27

<210> SEQ ID NO 20
<211> LENGTH: 1416
<212> TYPE: DNA
<213> ORGANISM: Bacillus subtilis
<220> FEATURE:
<221> NAME/KEY: CDS
<222> LOCATION: (1)..(1416)
<223> OTHER INFORMATION:

<400> SEQUENCE: 20

```
atg aaa aac aaa tgg tat aaa ccg aaa cgg cat tgg aag gag atc gag       48
Met Lys Asn Lys Trp Tyr Lys Pro Lys Arg His Trp Lys Glu Ile Glu
1               5                   10                  15

tta tgg aag gac gtt ccg gaa gag aaa tgg aac gat tgg ctt tgg cag       96
Leu Trp Lys Asp Val Pro Glu Glu Lys Trp Asn Asp Trp Leu Trp Gln
            20                  25                  30

ctg aca cac act gta aga acg tta gat gat tta aag aaa gtc att aat      144
Leu Thr His Thr Val Arg Thr Leu Asp Asp Leu Lys Lys Val Ile Asn
        35                  40                  45

ctg acc gag gat gaa gag gaa ggc gtc aga att tct acc aaa acg atc      192
Leu Thr Glu Asp Glu Glu Glu Gly Val Arg Ile Ser Thr Lys Thr Ile
    50                  55                  60

ccc tta aat att aca cct tac tat gct tct tta atg gac ccc gac aat      240
Pro Leu Asn Ile Thr Pro Tyr Tyr Ala Ser Leu Met Asp Pro Asp Asn
65                  70                  75                  80

ccg aga tgc ccg gta cgc atg cag tct gtg ccg ctt tct gaa gaa atg      288
Pro Arg Cys Pro Val Arg Met Gln Ser Val Pro Leu Ser Glu Glu Met
                85                  90                  95

cac aaa aca aaa tac gat atg gaa gac ccg ctt cat gag gat gaa gat      336
His Lys Thr Lys Tyr Asp Met Glu Asp Pro Leu His Glu Asp Glu Asp
            100                 105                 110

tca ccg gta ccc ggt ctg aca cac cgc tat ccc gac cgt gtg ctg ttt      384
Ser Pro Val Pro Gly Leu Thr His Arg Tyr Pro Asp Arg Val Leu Phe
        115                 120                 125

ctt gtc acg aat caa tgt tcc gtg tac tgc cgc tac tgc aca aga agg      432
Leu Val Thr Asn Gln Cys Ser Val Tyr Cys Arg Tyr Cys Thr Arg Arg
    130                 135                 140

cgc ttt tcc gga caa atc gga atg ggc gtc ccc aaa aaa cag ctt gat      480
Arg Phe Ser Gly Gln Ile Gly Met Gly Val Pro Lys Lys Gln Leu Asp
145                 150                 155                 160

gct gca att gct tat atc cgg gaa aca ccc gaa atc cgc gat tgt tta      528
Ala Ala Ile Ala Tyr Ile Arg Glu Thr Pro Glu Ile Arg Asp Cys Leu
                165                 170                 175

att tca ggc ggt gat ggg ctg ctc atc aac gac caa att tta gaa tat      576
Ile Ser Gly Gly Asp Gly Leu Leu Ile Asn Asp Gln Ile Leu Glu Tyr
            180                 185                 190

att tta aaa gag ctg cgc agc att ccg cat ctg gaa gtc atc aga atc      624
Ile Leu Lys Glu Leu Arg Ser Ile Pro His Leu Glu Val Ile Arg Ile
        195                 200                 205

gga aca aga gct ccc gtc gtc ttt ccg cag cgc att acc gat cat ctg      672
Gly Thr Arg Ala Pro Val Val Phe Pro Gln Arg Ile Thr Asp His Leu
    210                 215                 220

tgc gag ata ttg aaa aaa tat cat ccg gtc tgg ctg aac acc cat ttt      720
Cys Glu Ile Leu Lys Lys Tyr His Pro Val Trp Leu Asn Thr His Phe
225                 230                 235                 240

aac aca agc atc gaa atg aca gaa gaa tcc gtt gag gca tgt gaa aag      768
Asn Thr Ser Ile Glu Met Thr Glu Glu Ser Val Glu Ala Cys Glu Lys
                245                 250                 255

ctg gtg aac gcg gga gtg ccg gtc gga aat cag gct gtc gta tta gca      816
Leu Val Asn Ala Gly Val Pro Val Gly Asn Gln Ala Val Val Leu Ala
```

-continued

```
            260                 265                 270

ggt att aat gat tcg gtt cca att atg aaa aag ctc atg cat gac ttg      864
Gly Ile Asn Asp Ser Val Pro Ile Met Lys Lys Leu Met His Asp Leu
        275                 280                 285

gta aaa atc aga gtc cgt cct tat tat att tac caa tgt gat ctg tca      912
Val Lys Ile Arg Val Arg Pro Tyr Tyr Ile Tyr Gln Cys Asp Leu Ser
    290                 295                 300

gaa gga ata ggg cat ttc aga gct cct gtt tcc aaa ggt ttg gag atc      960
Glu Gly Ile Gly His Phe Arg Ala Pro Val Ser Lys Gly Leu Glu Ile
305                 310                 315                 320

att gaa ggg ctg aga ggt cat acc tca ggc tat gcg gtt cct acc ttt     1008
Ile Glu Gly Leu Arg Gly His Thr Ser Gly Tyr Ala Val Pro Thr Phe
                325                 330                 335

gtc gtt cac gca cca ggc gga gga ggt aaa atc gcc ctg cag ccg aac     1056
Val Val His Ala Pro Gly Gly Gly Gly Lys Ile Ala Leu Gln Pro Asn
            340                 345                 350

tat gtc ctg tca caa agt cct gac aaa gtg atc tta aga aat ttt gaa     1104
Tyr Val Leu Ser Gln Ser Pro Asp Lys Val Ile Leu Arg Asn Phe Glu
        355                 360                 365

ggt gtg att acg tca tat ccg gaa cca gag aat tat atc ccc aat cag     1152
Gly Val Ile Thr Ser Tyr Pro Glu Pro Glu Asn Tyr Ile Pro Asn Gln
    370                 375                 380

gca gac gcc tat ttt gag tcc gtt ttc cct gaa acc gct gac aaa aag     1200
Ala Asp Ala Tyr Phe Glu Ser Val Phe Pro Glu Thr Ala Asp Lys Lys
385                 390                 395                 400

gag ccg atc ggg ctg agt gcc att ttt gct gac aaa gaa gtt tcg ttt     1248
Glu Pro Ile Gly Leu Ser Ala Ile Phe Ala Asp Lys Glu Val Ser Phe
                405                 410                 415

aca cct gaa aat gta gac aga atc aaa agg aga gag gca tac atc gca     1296
Thr Pro Glu Asn Val Asp Arg Ile Lys Arg Arg Glu Ala Tyr Ile Ala
            420                 425                 430

aat ccg gag cat gaa aca tta aaa gat cgg cgt gag aaa aga gat cag     1344
Asn Pro Glu His Glu Thr Leu Lys Asp Arg Arg Glu Lys Arg Asp Gln
        435                 440                 445

ctc aaa gaa aag aaa ttt ttg gcg cag cag aaa aaa cag aaa gag act     1392
Leu Lys Glu Lys Lys Phe Leu Ala Gln Gln Lys Lys Gln Lys Glu Thr
    450                 455                 460

gaa tgc gga ggg gat tct tca tga                                     1416
Glu Cys Gly Gly Asp Ser Ser
465                 470


<210> SEQ ID NO 21
<211> LENGTH: 471
<212> TYPE: PRT
<213> ORGANISM: Bacillus subtilis

<400> SEQUENCE: 21

Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95
```

-continued

```
His Lys Thr Lys Tyr Asp Met Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Val Tyr Cys Arg Tyr Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240

Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Gly His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val His Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Phe
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Asp Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470
```

<210> SEQ ID NO 22
<211> LENGTH: 438
<212> TYPE: DNA
<213> ORGANISM: Clostridium propionicum
<220> FEATURE:

```
<221> NAME/KEY: CDS
<222> LOCATION: (1)..(438)
<223> OTHER INFORMATION:

<400> SEQUENCE: 22

atg gta ggt aaa aag gtt gta cat cat tta atg atg agc gca aaa gat       48
Met Val Gly Lys Lys Val Val His His Leu Met Met Ser Ala Lys Asp
1               5                   10                  15

gct cac tat act gga aac tta gta aac ggc gct aga att gtg aat cag       96
Ala His Tyr Thr Gly Asn Leu Val Asn Gly Ala Arg Ile Val Asn Gln
            20                  25                  30

tgg ggc gac gtt ggt aca gaa tta atg gtt tat gtt gat ggt gac ata      144
Trp Gly Asp Val Gly Thr Glu Leu Met Val Tyr Val Asp Gly Asp Ile
        35                  40                  45

agc tta ttc ttg ggc tac aaa gat atc gaa ttc aca gct cct gta tat      192
Ser Leu Phe Leu Gly Tyr Lys Asp Ile Glu Phe Thr Ala Pro Val Tyr
    50                  55                  60

gtt ggt gac ttt atg gaa tac cac ggc tgg att gaa aaa gtt ggt aac      240
Val Gly Asp Phe Met Glu Tyr His Gly Trp Ile Glu Lys Val Gly Asn
65                  70                  75                  80

cag tcc tat aca tgt aaa ttt gaa gca tgg aaa gtt gca aca atg gtt      288
Gln Ser Tyr Thr Cys Lys Phe Glu Ala Trp Lys Val Ala Thr Met Val
                85                  90                  95

gat atc aca aat cct cag gat aca cgc gca aca gct tgt gag cct ccg      336
Asp Ile Thr Asn Pro Gln Asp Thr Arg Ala Thr Ala Cys Glu Pro Pro
            100                 105                 110

gta ttg tgc gga aga gca acg ggt agt ttg ttc atc gca aaa aaa gat      384
Val Leu Cys Gly Arg Ala Thr Gly Ser Leu Phe Ile Ala Lys Lys Asp
        115                 120                 125

cag aga ggc cct cag gaa tcc tct ttt aaa gag aga aag cac ccc ggt      432
Gln Arg Gly Pro Gln Glu Ser Ser Phe Lys Glu Arg Lys His Pro Gly
    130                 135                 140

gaa tga                                                              438
Glu
145


<210> SEQ ID NO 23
<211> LENGTH: 145
<212> TYPE: PRT
<213> ORGANISM: Clostridium propionicum

<400> SEQUENCE: 23

Met Val Gly Lys Lys Val Val His His Leu Met Met Ser Ala Lys Asp
1               5                   10                  15

Ala His Tyr Thr Gly Asn Leu Val Asn Gly Ala Arg Ile Val Asn Gln
            20                  25                  30

Trp Gly Asp Val Gly Thr Glu Leu Met Val Tyr Val Asp Gly Asp Ile
        35                  40                  45

Ser Leu Phe Leu Gly Tyr Lys Asp Ile Glu Phe Thr Ala Pro Val Tyr
    50                  55                  60

Val Gly Asp Phe Met Glu Tyr His Gly Trp Ile Glu Lys Val Gly Asn
65                  70                  75                  80

Gln Ser Tyr Thr Cys Lys Phe Glu Ala Trp Lys Val Ala Thr Met Val
                85                  90                  95

Asp Ile Thr Asn Pro Gln Asp Thr Arg Ala Thr Ala Cys Glu Pro Pro
            100                 105                 110

Val Leu Cys Gly Arg Ala Thr Gly Ser Leu Phe Ile Ala Lys Lys Asp
        115                 120                 125

Gln Arg Gly Pro Gln Glu Ser Ser Phe Lys Glu Arg Lys His Pro Gly
```

-continued 130 135 140

Glu
145

<210> SEQ ID NO 24
<211> LENGTH: 1554
<212> TYPE: DNA
<213> ORGANISM: Megasphaera elsdenii
<220> FEATURE:
<221> NAME/KEY: CDS
<222> LOCATION: (1)..(1554)
<223> OTHER INFORMATION:

<400> SEQUENCE: 24 atg aga aaa gta gaa atc att aca gct gaa caa gca gct cag ctc gta 48
Met Arg Lys Val Glu Ile Ile Thr Ala Glu Gln Ala Ala Gln Leu Val
1 5 10 15 aaa gac aac gac acg att acg tct atc ggc ttt gtc agc agc gcc cat 96
Lys Asp Asn Asp Thr Ile Thr Ser Ile Gly Phe Val Ser Ser Ala His
20 25 30 ccg gaa gca ctg acc aaa gct ttg gaa aaa cgg ttc ctg gac acg aac 144
Pro Glu Ala Leu Thr Lys Ala Leu Glu Lys Arg Phe Leu Asp Thr Asn
35 40 45 acc ccg cag aac ttg acc tac atc tat gca ggc tct cag ggc aaa cgc 192
Thr Pro Gln Asn Leu Thr Tyr Ile Tyr Ala Gly Ser Gln Gly Lys Arg
50 55 60 gat ggc cgt gcc gct gaa cat ctg gca cac aca ggc ctt ttg aaa cgc 240
Asp Gly Arg Ala Ala Glu His Leu Ala His Thr Gly Leu Leu Lys Arg
65 70 75 80 gcc atc atc ggt cac tgg cag act gta ccg gct atc ggt aaa ctg gct 288
Ala Ile Ile Gly His Trp Gln Thr Val Pro Ala Ile Gly Lys Leu Ala
85 90 95 gtc gaa aac aag att gaa gct tac aac ttc tcg cag ggc acg ttg gtc 336
Val Glu Asn Lys Ile Glu Ala Tyr Asn Phe Ser Gln Gly Thr Leu Val
100 105 110 cac tgg ttc cgc gcc ttg gca ggt cat aag ctc ggc gtc ttc acc gac 384
His Trp Phe Arg Ala Leu Ala Gly His Lys Leu Gly Val Phe Thr Asp
115 120 125 atc ggt ctg gaa act ttc ctc gat ccc cgt cag ctc ggc ggc aag ctc 432
Ile Gly Leu Glu Thr Phe Leu Asp Pro Arg Gln Leu Gly Gly Lys Leu
130 135 140 aat gac gta acc aaa gaa gac ctc gtc aaa ctg atc gaa gtc gat ggt 480
Asn Asp Val Thr Lys Glu Asp Leu Val Lys Leu Ile Glu Val Asp Gly
145 150 155 160 cat gaa cag ctt ttc tac ccg acc ttc ccg gtc aac gta gct ttc ctc 528
His Glu Gln Leu Phe Tyr Pro Thr Phe Pro Val Asn Val Ala Phe Leu
165 170 175 cgc ggt acg tat gct gat gaa tcc ggc aat atc acc atg gac gaa gaa 576
Arg Gly Thr Tyr Ala Asp Glu Ser Gly Asn Ile Thr Met Asp Glu Glu
180 185 190 atc ggg cct ttc gaa agc act tcc gta gcc cag gcc gtt cac aac tgt 624
Ile Gly Pro Phe Glu Ser Thr Ser Val Ala Gln Ala Val His Asn Cys
195 200 205 ggc ggt aaa gtc gtc gtc cag gtc aaa gac gtc gtc gct cac ggc agc 672
Gly Gly Lys Val Val Val Gln Val Lys Asp Val Val Ala His Gly Ser
210 215 220 ctc gac ccg cgc atg gtc aag atc cct ggc atc tat gtc gac tac gtc 720
Leu Asp Pro Arg Met Val Lys Ile Pro Gly Ile Tyr Val Asp Tyr Val
225 230 235 240 gtc gta gca gct ccg gaa gac cat cag cag acg tat gac tgc gaa tac 768
Val Val Ala Ala Pro Glu Asp His Gln Gln Thr Tyr Asp Cys Glu Tyr -continued

```
            245                 250                 255

gat ccg tcc ctc agc ggt gaa cat cgt gct cct gaa ggc gct acc gat      816
Asp Pro Ser Leu Ser Gly Glu His Arg Ala Pro Glu Gly Ala Thr Asp
        260                 265                 270

gca gct ctc ccc atg agc gct aag aaa atc atc ggc cgc cgc ggc gct      864
Ala Ala Leu Pro Met Ser Ala Lys Lys Ile Ile Gly Arg Arg Gly Ala
    275                 280                 285

ttg gaa ttg act gaa aac gct gtc gtc aac ctc ggc gtc ggt gct ccg      912
Leu Glu Leu Thr Glu Asn Ala Val Val Asn Leu Gly Val Gly Ala Pro
    290                 295                 300

gaa tac gtt gct tct gtt gcc ggt gaa gaa ggt atc gcc gat acc att      960
Glu Tyr Val Ala Ser Val Ala Gly Glu Glu Gly Ile Ala Asp Thr Ile
305                 310                 315                 320

acc ctg acc gtc gaa ggt ggc gcc atc ggt ggc gta ccg cag ggc ggt     1008
Thr Leu Thr Val Glu Gly Gly Ala Ile Gly Gly Val Pro Gln Gly Gly
                325                 330                 335

gcc cgc ttc ggt tcg tcc cgc aat gcc gat gcc atc atc gac cac acc     1056
Ala Arg Phe Gly Ser Ser Arg Asn Ala Asp Ala Ile Ile Asp His Thr
            340                 345                 350

tat cag ttc gac ttc tac gat ggc ggc ggt ctg gac atc gct tac ctc     1104
Tyr Gln Phe Asp Phe Tyr Asp Gly Gly Gly Leu Asp Ile Ala Tyr Leu
        355                 360                 365

ggc ctg gcc cag tgc gat ggc tcg ggc aac atc aac gtc agc aag ttc     1152
Gly Leu Ala Gln Cys Asp Gly Ser Gly Asn Ile Asn Val Ser Lys Phe
    370                 375                 380

ggt act aac gtt gcc ggc tgc ggc ggt ttc ccc aac att tcc cag cag     1200
Gly Thr Asn Val Ala Gly Cys Gly Gly Phe Pro Asn Ile Ser Gln Gln
385                 390                 395                 400

aca ccg aat gtt tac ttc tgc ggc acc ttc acg gct ggc ggc ttg aaa     1248
Thr Pro Asn Val Tyr Phe Cys Gly Thr Phe Thr Ala Gly Gly Leu Lys
                405                 410                 415

atc gct gtc gaa gac ggc aaa gtc aag atc ctc cag gaa ggc aaa gcc     1296
Ile Ala Val Glu Asp Gly Lys Val Lys Ile Leu Gln Glu Gly Lys Ala
            420                 425                 430

aag aag ttc atc aaa gct gtc gac cag atc act ttc aac ggt tcc tat     1344
Lys Lys Phe Ile Lys Ala Val Asp Gln Ile Thr Phe Asn Gly Ser Tyr
        435                 440                 445

gca gcc cgc aac ggc aaa cac gtt ctc tac atc aca gaa cgc tgc gta     1392
Ala Ala Arg Asn Gly Lys His Val Leu Tyr Ile Thr Glu Arg Cys Val
    450                 455                 460

ttt gaa ctg acc aaa gaa ggc ttg aaa ctc atc gaa gtc gca ccg ggc     1440
Phe Glu Leu Thr Lys Glu Gly Leu Lys Leu Ile Glu Val Ala Pro Gly
465                 470                 475                 480

atc gat att gaa aaa gat atc ctc gct cac atg gac ttc aag ccg atc     1488
Ile Asp Ile Glu Lys Asp Ile Leu Ala His Met Asp Phe Lys Pro Ile
                485                 490                 495

att gat aat ccg aaa ctc atg gat gcc cgc ctc ttc cag gac ggt ccc     1536
Ile Asp Asn Pro Lys Leu Met Asp Ala Arg Leu Phe Gln Asp Gly Pro
            500                 505                 510

atg gga ctg aaa aaa taa                                             1554
Met Gly Leu Lys Lys
        515


<210> SEQ ID NO 25
<211> LENGTH: 517
<212> TYPE: PRT
<213> ORGANISM: Megasphaera elsdenii

<400> SEQUENCE: 25

Met Arg Lys Val Glu Ile Ile Thr Ala Glu Gln Ala Ala Gln Leu Val
```

-continued

```
1               5                   10                  15

Lys Asp Asn Asp Thr Ile Thr Ser Ile Gly Phe Val Ser Ser Ala His
            20                  25                  30

Pro Glu Ala Leu Thr Lys Ala Leu Glu Lys Arg Phe Leu Asp Thr Asn
        35                  40                  45

Thr Pro Gln Asn Leu Thr Tyr Ile Tyr Ala Gly Ser Gln Gly Lys Arg
    50                  55                  60

Asp Gly Arg Ala Ala Glu His Leu Ala His Thr Gly Leu Leu Lys Arg
65                  70                  75                  80

Ala Ile Ile Gly His Trp Gln Thr Val Pro Ala Ile Gly Lys Leu Ala
                85                  90                  95

Val Glu Asn Lys Ile Glu Ala Tyr Asn Phe Ser Gln Gly Thr Leu Val
            100                 105                 110

His Trp Phe Arg Ala Leu Ala Gly His Lys Leu Gly Val Phe Thr Asp
        115                 120                 125

Ile Gly Leu Glu Thr Phe Leu Asp Pro Arg Gln Leu Gly Gly Lys Leu
    130                 135                 140

Asn Asp Val Thr Lys Glu Asp Leu Val Lys Leu Ile Glu Val Asp Gly
145                 150                 155                 160

His Glu Gln Leu Phe Tyr Pro Thr Phe Pro Val Asn Val Ala Phe Leu
                165                 170                 175

Arg Gly Thr Tyr Ala Asp Glu Ser Gly Asn Ile Thr Met Asp Glu Glu
            180                 185                 190

Ile Gly Pro Phe Glu Ser Thr Ser Val Ala Gln Ala Val His Asn Cys
        195                 200                 205

Gly Gly Lys Val Val Val Gln Val Lys Asp Val Val Ala His Gly Ser
    210                 215                 220

Leu Asp Pro Arg Met Val Lys Ile Pro Gly Ile Tyr Val Asp Tyr Val
225                 230                 235                 240

Val Val Ala Ala Pro Glu Asp His Gln Gln Thr Tyr Asp Cys Glu Tyr
                245                 250                 255

Asp Pro Ser Leu Ser Gly Glu His Arg Ala Pro Glu Gly Ala Thr Asp
            260                 265                 270

Ala Ala Leu Pro Met Ser Ala Lys Lys Ile Ile Gly Arg Arg Gly Ala
        275                 280                 285

Leu Glu Leu Thr Glu Asn Ala Val Val Asn Leu Gly Val Gly Ala Pro
    290                 295                 300

Glu Tyr Val Ala Ser Val Ala Gly Glu Glu Gly Ile Ala Asp Thr Ile
305                 310                 315                 320

Thr Leu Thr Val Glu Gly Gly Ala Ile Gly Gly Val Pro Gln Gly Gly
                325                 330                 335

Ala Arg Phe Gly Ser Ser Arg Asn Ala Asp Ala Ile Ile Asp His Thr
            340                 345                 350

Tyr Gln Phe Asp Phe Tyr Asp Gly Gly Gly Leu Asp Ile Ala Tyr Leu
        355                 360                 365

Gly Leu Ala Gln Cys Asp Gly Ser Gly Asn Ile Asn Val Ser Lys Phe
    370                 375                 380

Gly Thr Asn Val Ala Gly Cys Gly Gly Phe Pro Asn Ile Ser Gln Gln
385                 390                 395                 400

Thr Pro Asn Val Tyr Phe Cys Gly Thr Phe Thr Ala Gly Gly Leu Lys
                405                 410                 415

Ile Ala Val Glu Asp Gly Lys Val Lys Ile Leu Gln Glu Gly Lys Ala
            420                 425                 430
```

```
Lys Lys Phe Ile Lys Ala Val Asp Gln Ile Thr Phe Asn Gly Ser Tyr
        435                 440                 445

Ala Ala Arg Asn Gly Lys His Val Leu Tyr Ile Thr Glu Arg Cys Val
    450                 455                 460

Phe Glu Leu Thr Lys Glu Gly Leu Lys Leu Ile Glu Val Ala Pro Gly
465                 470                 475                 480

Ile Asp Ile Glu Lys Asp Ile Leu Ala His Met Asp Phe Lys Pro Ile
                485                 490                 495

Ile Asp Asn Pro Lys Leu Met Asp Ala Arg Leu Phe Gln Asp Gly Pro
            500                 505                 510

Met Gly Leu Lys Lys
        515

<210> SEQ ID NO 26
<211> LENGTH: 26
<212> TYPE: DNA
<213> ORGANISM: Artificial Sequence
<220> FEATURE:
<223> OTHER INFORMATION: PCR primer

<400> SEQUENCE: 26

caagctgggt ctgttcatgc tggatg                                              26

<210> SEQ ID NO 27
<211> LENGTH: 27
<212> TYPE: DNA
<213> ORGANISM: Artificial Sequence
<220> FEATURE:
<223> OTHER INFORMATION: PCR primer

<400> SEQUENCE: 27

aagcggttct cgccctcgta aacctga                                             27

<210> SEQ ID NO 28
<211> LENGTH: 416
<212> TYPE: PRT
<213> ORGANISM: Porphyromonas gingivalis

<400> SEQUENCE: 28

Met Ala Glu Ser Arg Arg Lys Tyr Tyr Phe Pro Asp Val Thr Asp Glu
1               5                   10                  15

Gln Trp Asn Asp Trp His Trp Gln Val Leu Asn Arg Ile Glu Thr Leu
            20                  25                  30

Asp Gln Leu Lys Lys Tyr Val Thr Leu Thr Ala Glu Glu Glu Glu Gly
        35                  40                  45

Val Lys Glu Ser Leu Lys Val Leu Arg Met Ala Ile Thr Pro Tyr Tyr
    50                  55                  60

Leu Ser Leu Ile Asp Pro Glu Asn Pro Asn Cys Pro Ile Arg Lys Gln
65                  70                  75                  80

Ala Ile Pro Thr His Gln Glu Leu Val Arg Ala Pro Glu Asp Gln Val
                85                  90                  95

Asp Pro Leu Ser Glu Asp Glu Asp Ser Pro Val Pro Gly Leu Thr His
            100                 105                 110

Arg Tyr Pro Asp Arg Val Leu Phe Leu Ile Thr Asp Lys Cys Ser Met
        115                 120                 125

Tyr Cys Arg His Cys Thr Arg Arg Arg Phe Ala Gly Gln Lys Asp Ala
    130                 135                 140

Ser Ser Pro Ser Glu Arg Ile Asp Arg Cys Ile Asp Tyr Ile Ala Asn
```

-continued

```
145                 150                 155                 160

Thr Pro Thr Val Arg Asp Val Leu Leu Ser Gly Gly Asp Ala Leu Leu
                165                 170                 175

Val Ser Asp Glu Arg Leu Glu Tyr Ile Leu Lys Arg Leu Arg Glu Ile
            180                 185                 190

Pro His Val Glu Ile Val Arg Ile Gly Ser Arg Thr Pro Val Val Leu
        195                 200                 205

Pro Gln Arg Ile Thr Pro Gln Leu Val Asp Met Leu Lys Lys Tyr His
    210                 215                 220

Pro Val Trp Leu Asn Thr His Phe Asn His Pro Asn Glu Val Thr Glu
225                 230                 235                 240

Glu Ala Val Glu Ala Cys Glu Arg Met Ala Asn Ala Gly Ile Pro Leu
                245                 250                 255

Gly Asn Gln Thr Val Leu Leu Arg Gly Ile Asn Asp Cys Thr His Val
            260                 265                 270

Met Lys Arg Leu Val His Leu Leu Val Lys Met Arg Val Arg Pro Tyr
        275                 280                 285

Tyr Ile Tyr Val Cys Asp Leu Ser Leu Gly Ile Gly His Phe Arg Thr
    290                 295                 300

Pro Val Ser Lys Gly Ile Glu Ile Ile Glu Asn Leu Arg Gly His Thr
305                 310                 315                 320

Ser Gly Tyr Ala Val Pro Thr Phe Val Val Asp Ala Pro Gly Gly Gly
                325                 330                 335

Gly Lys Ile Pro Val Met Pro Asn Tyr Val Val Ser Gln Ser Pro Arg
            340                 345                 350

His Val Val Leu Arg Asn Tyr Glu Gly Val Ile Thr Thr Tyr Thr Glu
        355                 360                 365

Pro Glu Asn Tyr His Glu Glu Cys Asp Cys Glu Asp Cys Arg Ala Gly
    370                 375                 380

Lys His Lys Glu Gly Val Ala Ala Leu Ser Gly Gly Gln Gln Leu Ala
385                 390                 395                 400

Ile Glu Pro Ser Asp Leu Ala Arg Lys Lys Arg Lys Phe Asp Lys Asn
                405                 410                 415


<210> SEQ ID NO 29
<211> LENGTH: 1251
<212> TYPE: DNA
<213> ORGANISM: Porphyromonas gingivalis
<220> FEATURE:
<221> NAME/KEY: CDS
<222> LOCATION: (1)..(1251)
<223> OTHER INFORMATION:

<400> SEQUENCE: 29

atg gca gaa agt cgt aga aag tat tat ttc cct gat gtc acc gat gag       48
Met Ala Glu Ser Arg Arg Lys Tyr Tyr Phe Pro Asp Val Thr Asp Glu
1               5                   10                  15

caa tgg tac gac tgg cat tgg cag gtc ctc aat cga att gag acg ctc       96
Gln Trp Tyr Asp Trp His Trp Gln Val Leu Asn Arg Ile Glu Thr Leu
            20                  25                  30

gac cag ctg aaa aag tac gtt aca ctc acc gct gaa gaa gaa gag gga      144
Asp Gln Leu Lys Lys Tyr Val Thr Leu Thr Ala Glu Glu Glu Glu Gly
        35                  40                  45

gta aaa gaa tcg ccc aaa gta ctc cga atg gct atc aca cct tat tat      192
Val Lys Glu Ser Pro Lys Val Leu Arg Met Ala Ile Thr Pro Tyr Tyr
    50                  55                  60

ttg agt ttg ata gac ccc gag aat cct aat tgt ccg att cgt aaa caa      240
```

-continued

```
Leu Ser Leu Ile Asp Pro Glu Asn Pro Asn Cys Pro Ile Arg Lys Gln
65                  70                  75                  80

gcc att cct act caa cag gaa ctg gta cgt gct cct gaa gat cag gta      288
Ala Ile Pro Thr Gln Gln Glu Leu Val Arg Ala Pro Glu Asp Gln Val
                85                  90                  95

gac cca ctt agt gaa gat gaa gat tcg ccc gta ccc gga ctg act cat      336
Asp Pro Leu Ser Glu Asp Glu Asp Ser Pro Val Pro Gly Leu Thr His
            100                 105                 110

cgt tat ccg gat cgt gta ttg ttc ctt atc acg gac aaa tgt tcg atg      384
Arg Tyr Pro Asp Arg Val Leu Phe Leu Ile Thr Asp Lys Cys Ser Met
        115                 120                 125

tac tgt cgt cat tgt act cgc cgt cgc ttc gca gga cag aaa gat gct      432
Tyr Cys Arg His Cys Thr Arg Arg Arg Phe Ala Gly Gln Lys Asp Ala
    130                 135                 140

tct tct cct tct gag cgc atc gat cga tgc att gac tat ata gcc aat      480
Ser Ser Pro Ser Glu Arg Ile Asp Arg Cys Ile Asp Tyr Ile Ala Asn
145                 150                 155                 160

aca ccg aca gtc cgc gat gtt ttg cta tcg gga ggc gat gcc ctc ctt      528
Thr Pro Thr Val Arg Asp Val Leu Leu Ser Gly Gly Asp Ala Leu Leu
                165                 170                 175

gtc agc gac gaa cgc ttg gaa tac ata ttg aag cgt ctg cgc gaa ata      576
Val Ser Asp Glu Arg Leu Glu Tyr Ile Leu Lys Arg Leu Arg Glu Ile
            180                 185                 190

cct cat gtg gag att gtt cgt ata gga agc cgt acg ccg gta gtc ctc      624
Pro His Val Glu Ile Val Arg Ile Gly Ser Arg Thr Pro Val Val Leu
        195                 200                 205

cct cag cgt ata acg cct caa ttg gtg gat atg ctc aaa aaa tat cat      672
Pro Gln Arg Ile Thr Pro Gln Leu Val Asp Met Leu Lys Lys Tyr His
    210                 215                 220

ccg gtg tgg ctg aac act cac ttc aac cac ccg aat gaa gtt acc gaa      720
Pro Val Trp Leu Asn Thr His Phe Asn His Pro Asn Glu Val Thr Glu
225                 230                 235                 240

gaa gca gta gag gct tgt gaa aga atg gcc aat gcc ggt att ccg ttg      768
Glu Ala Val Glu Ala Cys Glu Arg Met Ala Asn Ala Gly Ile Pro Leu
                245                 250                 255

ggt aac caa acg gtt tta ttg cgt gga atc aat gat tgt aca cat gtg      816
Gly Asn Gln Thr Val Leu Leu Arg Gly Ile Asn Asp Cys Thr His Val
            260                 265                 270

atg aag aga ttg gta cat ttg ctg gta aag atg cgt gtg cgt cct tac      864
Met Lys Arg Leu Val His Leu Leu Val Lys Met Arg Val Arg Pro Tyr
        275                 280                 285

tat ata tat gta tgc gat ctt tcg ctt gga ata ggt cat ttc cgc acg      912
Tyr Ile Tyr Val Cys Asp Leu Ser Leu Gly Ile Gly His Phe Arg Thr
    290                 295                 300

ccg gta tct aaa gga atc gaa att atc gaa aat ttg cgc gga cac acc      960
Pro Val Ser Lys Gly Ile Glu Ile Ile Glu Asn Leu Arg Gly His Thr
305                 310                 315                 320

tcg ggc tat gca gtt cct acc ttt gtg gta ggt gct ccg ggg ggt ggt     1008
Ser Gly Tyr Ala Val Pro Thr Phe Val Val Gly Ala Pro Gly Gly Gly
                325                 330                 335

ggt aag ata cct gta acg ccg aac tat gtt gta tct cag tcc cca cga     1056
Gly Lys Ile Pro Val Thr Pro Asn Tyr Val Val Ser Gln Ser Pro Arg
            340                 345                 350

cat gtg gtt ctt cgc aat tat gaa ggt gtt atc aca acc tat acg gag     1104
His Val Val Leu Arg Asn Tyr Glu Gly Val Ile Thr Thr Tyr Thr Glu
        355                 360                 365

ccg gag aat tat cat gag gag tgc gat tgt gag gac tgt cga gcc ggt     1152
Pro Glu Asn Tyr His Glu Glu Cys Asp Cys Glu Asp Cys Arg Ala Gly
    370                 375                 380
```

-continued

```
aag cat aaa gag ggt gta gct gca ctt tcc gga ggt cag cag ttg gct      1200
Lys His Lys Glu Gly Val Ala Ala Leu Ser Gly Gly Gln Gln Leu Ala
385                 390                 395                 400

atc gag cct tcc gac tta gct cgc aaa aaa cgc aag ttt gat aag aac      1248
Ile Glu Pro Ser Asp Leu Ala Arg Lys Lys Arg Lys Phe Asp Lys Asn
                405                 410                 415

tga                                                                  1251


<210> SEQ ID NO 30
<211> LENGTH: 416
<212> TYPE: PRT
<213> ORGANISM: Porphyromonas gingivalis

<400> SEQUENCE: 30

Met Ala Glu Ser Arg Arg Lys Tyr Tyr Phe Pro Asp Val Thr Asp Glu
1               5                   10                  15

Gln Trp Tyr Asp Trp His Trp Gln Val Leu Asn Arg Ile Glu Thr Leu
            20                  25                  30

Asp Gln Leu Lys Lys Tyr Val Thr Leu Thr Ala Glu Glu Glu Glu Gly
        35                  40                  45

Val Lys Glu Ser Pro Lys Val Leu Arg Met Ala Ile Thr Pro Tyr Tyr
    50                  55                  60

Leu Ser Leu Ile Asp Pro Glu Asn Pro Asn Cys Pro Ile Arg Lys Gln
65                  70                  75                  80

Ala Ile Pro Thr Gln Gln Glu Leu Val Arg Ala Pro Glu Asp Gln Val
                85                  90                  95

Asp Pro Leu Ser Glu Asp Glu Asp Ser Pro Val Pro Gly Leu Thr His
            100                 105                 110

Arg Tyr Pro Asp Arg Val Leu Phe Leu Ile Thr Asp Lys Cys Ser Met
        115                 120                 125

Tyr Cys Arg His Cys Thr Arg Arg Arg Phe Ala Gly Gln Lys Asp Ala
    130                 135                 140

Ser Ser Pro Ser Glu Arg Ile Asp Arg Cys Ile Asp Tyr Ile Ala Asn
145                 150                 155                 160

Thr Pro Thr Val Arg Asp Val Leu Leu Ser Gly Gly Asp Ala Leu Leu
                165                 170                 175

Val Ser Asp Glu Arg Leu Glu Tyr Ile Leu Lys Arg Leu Arg Glu Ile
            180                 185                 190

Pro His Val Glu Ile Val Arg Ile Gly Ser Arg Thr Pro Val Val Leu
        195                 200                 205

Pro Gln Arg Ile Thr Pro Gln Leu Val Asp Met Leu Lys Lys Tyr His
    210                 215                 220

Pro Val Trp Leu Asn Thr His Phe Asn His Pro Asn Glu Val Thr Glu
225                 230                 235                 240

Glu Ala Val Glu Ala Cys Glu Arg Met Ala Asn Ala Gly Ile Pro Leu
                245                 250                 255

Gly Asn Gln Thr Val Leu Leu Arg Gly Ile Asn Asp Cys Thr His Val
            260                 265                 270

Met Lys Arg Leu Val His Leu Leu Val Lys Met Arg Val Arg Pro Tyr
        275                 280                 285

Tyr Ile Tyr Val Cys Asp Leu Ser Leu Gly Ile Gly His Phe Arg Thr
    290                 295                 300

Pro Val Ser Lys Gly Ile Glu Ile Ile Glu Asn Leu Arg Gly His Thr
305                 310                 315                 320

Ser Gly Tyr Ala Val Pro Thr Phe Val Val Gly Ala Pro Gly Gly Gly
```

-continued

```
                325                 330                 335

Gly Lys Ile Pro Val Thr Pro Asn Tyr Val Val Ser Gln Ser Pro Arg
            340                 345                 350

His Val Val Leu Arg Asn Tyr Glu Gly Val Ile Thr Thr Tyr Thr Glu
        355                 360                 365

Pro Glu Asn Tyr His Glu Glu Cys Asp Cys Glu Asp Cys Arg Ala Gly
    370                 375                 380

Lys His Lys Glu Gly Val Ala Ala Leu Ser Gly Gly Gln Gln Leu Ala
385                 390                 395                 400

Ile Glu Pro Ser Asp Leu Ala Arg Lys Lys Arg Lys Phe Asp Lys Asn
                405                 410                 415


<210> SEQ ID NO 31
<211> LENGTH: 471
<212> TYPE: PRT
<213> ORGANISM: Bacillus subtilis

<400> SEQUENCE: 31

Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Leu Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Met Tyr Cys Arg Tyr Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240

Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285
```

-continued

```
Val Lys Ile Arg Val Arg Pro Tyr Tyr Ile Tyr Gln Cys Asp Leu Ser
    290                 295                 300

Glu Gly Ile Gly His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val Asp Ala Pro Gly Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Phe
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Asp Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470
```

<210> SEQ ID NO 32
<211> LENGTH: 28
<212> TYPE: DNA
<213> ORGANISM: Artificial Sequence
<220> FEATURE:
<223> OTHER INFORMATION: PCR primer

<400> SEQUENCE: 32

```
cgcattcaag tcaaagacgt tcaggcta                                          28
```

<210> SEQ ID NO 33
<211> LENGTH: 1387
<212> TYPE: DNA
<213> ORGANISM: Alcaligenes faecalis
<220> FEATURE:
<221> NAME/KEY: CDS
<222> LOCATION: (408)..(1304)
<223> OTHER INFORMATION:

<400> SEQUENCE: 33

```
cattacacag gctctgcagc agtggcaggg cagtgccgac ccctggttgt cccgtgccgc      60

gcaaaccttc gccaaaggtg cgcctggttc ggctcgtttg tcctttgagc tgctggagag     120

ggtgcatcac ctgtctttgg ccgatgtttt ccgtctggaa tacattgtgt cgctgcaatg     180

tggcgtacag ggcgacttcc aggaaggcat acgggcactg ctgattgata aagacaaaca     240

gccgcgctgg aatcctgcct cgctggaaca ggcggatgca cgctgggtgg aacgtttttt     300

tgttcctgcc tggccggcag aaacgactca tcccttggct gacctgtaac ccaggcagac     360

cgctgcggcg ccagacggcg ccgctttcat aatgacgagg agacaaa atg agt aac       416
                                                    Met Ser Asn
                                                    1

acg att gca ttt atc ggg ctg ggc cat atg ggt aaa ccc atg gcg ctg       464
Thr Ile Ala Phe Ile Gly Leu Gly His Met Gly Lys Pro Met Ala Leu
    5                   10                  15
```

-continued

```
aat ctg ctc aaa gcc ggt cat agc ctg aac gtc ttt gac ttg aat gcg      512
Asn Leu Leu Lys Ala Gly His Ser Leu Asn Val Phe Asp Leu Asn Ala
20                  25                  30                  35

caa gcc atg cag gaa ctg cag gca gca ggg gca cag gtg ggg gaa tcg      560
Gln Ala Met Gln Glu Leu Gln Ala Ala Gly Ala Gln Val Gly Glu Ser
                40                  45                  50

gcg gtg caa atc gcc caa gac gcg cag atg gtc ttt acc atg ctg cct      608
Ala Val Gln Ile Ala Gln Asp Ala Gln Met Val Phe Thr Met Leu Pro
            55                  60                  65

gct ggc cgc cat gtt cgt cag gtt tac gag ggc gag aac ggc ttg ctg      656
Ala Gly Arg His Val Arg Gln Val Tyr Glu Gly Glu Asn Gly Leu Leu
        70                  75                  80

cag act gtg gcc ccc ggt acg gtg ctg gtc gat tgc agc acc att gat      704
Gln Thr Val Ala Pro Gly Thr Val Leu Val Asp Cys Ser Thr Ile Asp
    85                  90                  95

gcg caa acc agc cag gat ctg gcg gcc aaa gcc agc aag ctg ggt ctg      752
Ala Gln Thr Ser Gln Asp Leu Ala Ala Lys Ala Ser Lys Leu Gly Leu
100                 105                 110                 115

ttc atg ctg gat gcg ccg gtc tcc ggt ggg acc ggt ggc gcc att gct      800
Phe Met Leu Asp Ala Pro Val Ser Gly Gly Thr Gly Gly Ala Ile Ala
                120                 125                 130

ggc acc ttg acc ttt atg gtc ggg ggc gag gat cag gcc ctg gaa aag      848
Gly Thr Leu Thr Phe Met Val Gly Gly Glu Asp Gln Ala Leu Glu Lys
            135                 140                 145

gcg cgc cct tac ttg gat gcc atg ggc aag aac att ttc cac gcg ggt      896
Ala Arg Pro Tyr Leu Asp Ala Met Gly Lys Asn Ile Phe His Ala Gly
        150                 155                 160

aaa gcc ggt gcg ggt cag gtt gcc aag att tgc aac aat atg ctc ttg      944
Lys Ala Gly Ala Gly Gln Val Ala Lys Ile Cys Asn Asn Met Leu Leu
    165                 170                 175

ggg att ttg atg gcg ggt act gct gaa gcc ttg gct ttg ggc gtt gcc      992
Gly Ile Leu Met Ala Gly Thr Ala Glu Ala Leu Ala Leu Gly Val Ala
180                 185                 190                 195

cac ggt ctg gac cct gcc gtg ctg tcg acc atc atg gcg cgc agt tcc     1040
His Gly Leu Asp Pro Ala Val Leu Ser Thr Ile Met Ala Arg Ser Ser
                200                 205                 210

ggt cga aac tgg gca acc gag ctg tac aac ccc tgg cct ggg gtg atg     1088
Gly Arg Asn Trp Ala Thr Glu Leu Tyr Asn Pro Trp Pro Gly Val Met
            215                 220                 225

ccg gat gta ccg gct tcg cgt gat tat cag ggc ggt ttt gcg acg ggc     1136
Pro Asp Val Pro Ala Ser Arg Asp Tyr Gln Gly Gly Phe Ala Thr Gly
        230                 235                 240

ctg atg ctc aaa gac ctg ggt ctg gca gcc gat gcg gct gtc agc cag     1184
Leu Met Leu Lys Asp Leu Gly Leu Ala Ala Asp Ala Ala Val Ser Gln
    245                 250                 255

aac agc gcg acg cct ttg ggc gaa ctg gca cgt aac ctg ttc gcc ttg     1232
Asn Ser Ala Thr Pro Leu Gly Glu Leu Ala Arg Asn Leu Phe Ala Leu
260                 265                 270                 275

cac gcc gca caa ggt cag aat gca ggg ctg gat ttc tcc agc att ctt     1280
His Ala Ala Gln Gly Gln Asn Ala Gly Leu Asp Phe Ser Ser Ile Leu
                280                 285                 290

aat ttg tac cgt cag aag cac taa gttctggcag tgcgtagggc aggggctgca    1334
Asn Leu Tyr Arg Gln Lys His
            295

gttccagcgc ctgtccttgc tccaattgaa actggccttg ttccaggtcc gcc          1387
```

<210> SEQ ID NO 34
<211> LENGTH: 298
<212> TYPE: PRT

-continued

<213> ORGANISM: Alcaligenes faecalis

<400> SEQUENCE: 34

Met Ser Asn Thr Ile Ala Phe Ile Gly Leu Gly His Met Gly Lys Pro
1               5                   10                  15

Met Ala Leu Asn Leu Leu Lys Ala Gly His Ser Leu Asn Val Phe Asp
            20                  25                  30

Leu Asn Ala Gln Ala Met Gln Glu Leu Gln Ala Ala Gly Ala Gln Val
        35                  40                  45

Gly Glu Ser Ala Val Gln Ile Ala Gln Asp Ala Gln Met Val Phe Thr
    50                  55                  60

Met Leu Pro Ala Gly Arg His Val Arg Gln Val Tyr Glu Gly Glu Asn
65                  70                  75                  80

Gly Leu Leu Gln Thr Val Ala Pro Gly Thr Val Leu Val Asp Cys Ser
                85                  90                  95

Thr Ile Asp Ala Gln Thr Ser Gln Asp Leu Ala Ala Lys Ala Ser Lys
            100                 105                 110

Leu Gly Leu Phe Met Leu Asp Ala Pro Val Ser Gly Gly Thr Gly Gly
        115                 120                 125

Ala Ile Ala Gly Thr Leu Thr Phe Met Val Gly Gly Glu Asp Gln Ala
    130                 135                 140

Leu Glu Lys Ala Arg Pro Tyr Leu Asp Ala Met Gly Lys Asn Ile Phe
145                 150                 155                 160

His Ala Gly Lys Ala Gly Ala Gly Gln Val Ala Lys Ile Cys Asn Asn
                165                 170                 175

Met Leu Leu Gly Ile Leu Met Ala Gly Thr Ala Glu Ala Leu Ala Leu
            180                 185                 190

Gly Val Ala His Gly Leu Asp Pro Ala Val Leu Ser Thr Ile Met Ala
        195                 200                 205

Arg Ser Ser Gly Arg Asn Trp Ala Thr Glu Leu Tyr Asn Pro Trp Pro
    210                 215                 220

Gly Val Met Pro Asp Val Pro Ala Ser Arg Asp Tyr Gln Gly Gly Phe
225                 230                 235                 240

Ala Thr Gly Leu Met Leu Lys Asp Leu Gly Leu Ala Ala Asp Ala Ala
                245                 250                 255

Val Ser Gln Asn Ser Ala Thr Pro Leu Gly Glu Leu Ala Arg Asn Leu
            260                 265                 270

Phe Ala Leu His Ala Ala Gln Gly Gln Asn Ala Gly Leu Asp Phe Ser
        275                 280                 285

Ser Ile Leu Asn Leu Tyr Arg Gln Lys His
    290                 295

<210> SEQ ID NO 35
<211> LENGTH: 36
<212> TYPE: DNA
<213> ORGANISM: Artificial Sequence
<220> FEATURE:
<223> OTHER INFORMATION: PCR primer

<400> SEQUENCE: 35
gggaattcca tatggtaggt aaaaaggttg tacatc 36

<210> SEQ ID NO 36
<211> LENGTH: 34
<212> TYPE: DNA
<213> ORGANISM: Artificial Sequence
<220> FEATURE:

-continued

<223> OTHER INFORMATION: PCR primer

<400> SEQUENCE: 36
cgacggatcc attcgtccgc ttgaataact aaag 34

<210> SEQ ID NO 37
<211> LENGTH: 36
<212> TYPE: DNA
<213> ORGANISM: Artificial Sequence
<220> FEATURE:
<223> OTHER INFORMATION: PCR primer

<400> SEQUENCE: 37
cgacggatcc cgaaaatgtc accaaaaatt attgag 36

<210> SEQ ID NO 38
<211> LENGTH: 28
<212> TYPE: DNA
<213> ORGANISM: Artificial Sequence
<220> FEATURE:
<223> OTHER INFORMATION: PCR primer

<400> SEQUENCE: 38
agagagcata tgtcttttca ccttcggc 28

<210> SEQ ID NO 39
<211> LENGTH: 35
<212> TYPE: DNA
<213> ORGANISM: Artificial Sequence
<220> FEATURE:
<223> OTHER INFORMATION: PCR primer

<400> SEQUENCE: 39
agagagggat ccgcggctcc cacaatgttg aaatg 35

<210> SEQ ID NO 40
<211> LENGTH: 32
<212> TYPE: DNA
<213> ORGANISM: Artificial Sequence
<220> FEATURE:
<223> OTHER INFORMATION: PCR primer

<400> SEQUENCE: 40
agagagcata tgacaaataa tgaaagcaaa gg 32

<210> SEQ ID NO 41
<211> LENGTH: 39
<212> TYPE: DNA
<213> ORGANISM: Artificial Sequence
<220> FEATURE:
<223> OTHER INFORMATION: PCR primer

<400> SEQUENCE: 41
gggaattcca tatgagaaaa gtagaaatca ttacagctg 39

<210> SEQ ID NO 42
<211> LENGTH: 38
<212> TYPE: DNA
<213> ORGANISM: Artificial Sequence
<220> FEATURE:
<223> OTHER INFORMATION: PCR primer

<400> SEQUENCE: 42
acgttgatct ccttctacat tattttttca gtcccatg 38

-continued

<210> SEQ ID NO 43
<211> LENGTH: 38
<212> TYPE: DNA
<213> ORGANISM: Artificial Sequence
<220> FEATURE:
<223> OTHER INFORMATION: PCR primer

<400> SEQUENCE: 43
catgggactg aaaaaataat gtagaaggag atcaacgt 38

<210> SEQ ID NO 44
<211> LENGTH: 30
<212> TYPE: DNA
<213> ORGANISM: Artificial Sequence
<220> FEATURE:
<223> OTHER INFORMATION: PCR primer

<400> SEQUENCE: 44
cgacggatcc tcaacgacca ctgaagttgg 30

<210> SEQ ID NO 45
<211> LENGTH: 32
<212> TYPE: DNA
<213> ORGANISM: Artificial Sequence
<220> FEATURE:
<223> OTHER INFORMATION: PCR primer

<400> SEQUENCE: 45
ctagtctaga gctttctaag aaacgatttc cg 32

<210> SEQ ID NO 46
<211> LENGTH: 53
<212> TYPE: DNA
<213> ORGANISM: Artificial Sequence
<220> FEATURE:
<223> OTHER INFORMATION: PCR primer

<400> SEQUENCE: 46
gggaattcca tatgcgtaac ttcctcctgc tatcattcac cggggtgctt tct 53

<210> SEQ ID NO 47
<211> LENGTH: 30
<212> TYPE: DNA
<213> ORGANISM: Artificial Sequence
<220> FEATURE:
<223> OTHER INFORMATION: PCR primer

<400> SEQUENCE: 47
ctagtctaga ggaaaccgct taacgaactc 30

<210> SEQ ID NO 48
<211> LENGTH: 54
<212> TYPE: DNA
<213> ORGANISM: Artificial Sequence
<220> FEATURE:
<223> OTHER INFORMATION: PCR primer

<400> SEQUENCE: 48
gggaattcca tatgcgtaac ttcctcctgc tattattgag ggtgctttgc atcc 54

<210> SEQ ID NO 49
<211> LENGTH: 31
<212> TYPE: DNA
<213> ORGANISM: Artificial Sequence
<220> FEATURE:
<223> OTHER INFORMATION: PCR primer -continued

<400> SEQUENCE: 49

```
ccggaattct ttaatatgcg atttggagga g                                    31


<210> SEQ ID NO 50
<211> LENGTH: 39
<212> TYPE: DNA
<213> ORGANISM: Artificial Sequence
<220> FEATURE:
<223> OTHER INFORMATION: PCR primer

<400> SEQUENCE: 50

gtccgtctcc ctttcagctt aaatcgctat tcttatagc                            39


<210> SEQ ID NO 51
<211> LENGTH: 39
<212> TYPE: DNA
<213> ORGANISM: Artificial Sequence
<220> FEATURE:
<223> OTHER INFORMATION: PCR primer

<400> SEQUENCE: 51

gctataagaa tagcgattta agctgaaagg gagacggac                            39


<210> SEQ ID NO 52
<211> LENGTH: 30
<212> TYPE: DNA
<213> ORGANISM: Artificial Sequence
<220> FEATURE:
<223> OTHER INFORMATION: PCR primer

<400> SEQUENCE: 52

cgacggatcc gcagtgagtg agccttggag                                      30


<210> SEQ ID NO 53
<211> LENGTH: 435
<212> TYPE: DNA
<213> ORGANISM: Clostridium propionicum
<220> FEATURE:
<221> NAME/KEY: CDS
<222> LOCATION: (1)..(435)
<223> OTHER INFORMATION:

<400> SEQUENCE: 53

atg gta ggt aaa aag gtt gta cat cat tta atg atg agc gca aaa gac       48
Met Val Gly Lys Lys Val Val His His Leu Met Met Ser Ala Lys Asp
1               5                   10                  15

gct cac tat act gga aac tta gta aac ggc gct aga atc gtg aat cag       96
Ala His Tyr Thr Gly Asn Leu Val Asn Gly Ala Arg Ile Val Asn Gln
            20                  25                  30

tgg ggc gac gta ggt aca gaa tta atg gtt tat gtt gat ggt gac atc      144
Trp Gly Asp Val Gly Thr Glu Leu Met Val Tyr Val Asp Gly Asp Ile
        35                  40                  45

agc tta ttc ttg ggc tac aaa gat atc gaa ttc aca gct cct gta tat      192
Ser Leu Phe Leu Gly Tyr Lys Asp Ile Glu Phe Thr Ala Pro Val Tyr
    50                  55                  60

gtt ggt gat ttt atg gaa tac cac ggc tgg att gaa aaa gtt ggc aac      240
Val Gly Asp Phe Met Glu Tyr His Gly Trp Ile Glu Lys Val Gly Asn
65                  70                  75                  80

cag tcc tat aca tgt aaa ttt gaa gca tgg aaa gta gca aag atg gtt      288
Gln Ser Tyr Thr Cys Lys Phe Glu Ala Trp Lys Val Ala Lys Met Val
                85                  90                  95

gat atc aca aat cca cag gat aca cgt gca aca gct tgt gaa cct ccg      336
Asp Ile Thr Asn Pro Gln Asp Thr Arg Ala Thr Ala Cys Glu Pro Pro
            100                 105                 110
```

-continued

```
gta ctt tgt ggt act gca aca ggc agc ctt ttc atc gca aag gat aat      384
Val Leu Cys Gly Thr Ala Thr Gly Ser Leu Phe Ile Ala Lys Asp Asn
        115                 120                 125

cag aga ggt cct cag gaa tct tcc ttc aag gat gca aag cac cct caa      432
Gln Arg Gly Pro Gln Glu Ser Ser Phe Lys Asp Ala Lys His Pro Gln
    130                 135                 140

taa                                                                  435
```

<210> SEQ ID NO 54
<211> LENGTH: 144
<212> TYPE: PRT
<213> ORGANISM: Clostridium propionicum

<400> SEQUENCE: 54

```
Met Val Gly Lys Lys Val Val His His Leu Met Met Ser Ala Lys Asp
1               5                   10                  15

Ala His Tyr Thr Gly Asn Leu Val Asn Gly Ala Arg Ile Val Asn Gln
            20                  25                  30

Trp Gly Asp Val Gly Thr Glu Leu Met Val Tyr Val Asp Gly Asp Ile
        35                  40                  45

Ser Leu Phe Leu Gly Tyr Lys Asp Ile Glu Phe Thr Ala Pro Val Tyr
    50                  55                  60

Val Gly Asp Phe Met Glu Tyr His Gly Trp Ile Glu Lys Val Gly Asn
65                  70                  75                  80

Gln Ser Tyr Thr Cys Lys Phe Glu Ala Trp Lys Val Ala Lys Met Val
                85                  90                  95

Asp Ile Thr Asn Pro Gln Asp Thr Arg Ala Thr Ala Cys Glu Pro Pro
            100                 105                 110

Val Leu Cys Gly Thr Ala Thr Gly Ser Leu Phe Ile Ala Lys Asp Asn
        115                 120                 125

Gln Arg Gly Pro Gln Glu Ser Ser Phe Lys Asp Ala Lys His Pro Gln
    130                 135                 140
```

<210> SEQ ID NO 55
<211> LENGTH: 43
<212> TYPE: DNA
<213> ORGANISM: Artificial Sequence
<220> FEATURE:
<223> OTHER INFORMATION: PCR primer

<400> SEQUENCE: 55

```
aaggaaaaaa gcggccgcag attaaaggag gaattctcaa tgg                         43
```

<210> SEQ ID NO 56
<211> LENGTH: 30
<212> TYPE: DNA
<213> ORGANISM: Artificial Sequence
<220> FEATURE:
<223> OTHER INFORMATION: PCR primer

<400> SEQUENCE: 56

```
ctagtctaga tcaacgacca ctgaagttgg                                        30
```

<210> SEQ ID NO 57
<211> LENGTH: 40
<212> TYPE: DNA
<213> ORGANISM: Artificial Sequence
<220> FEATURE:
<223> OTHER INFORMATION: PCR primer

<400> SEQUENCE: 57

-continued aaggaaaaaa gcggccgctt taatatgcga tttggaggag 40

<210> SEQ ID NO 58
<211> LENGTH: 30
<212> TYPE: DNA
<213> ORGANISM: Artificial Sequence
<220> FEATURE:
<223> OTHER INFORMATION: PCR primer

<400> SEQUENCE: 58
ctagtctaga gcagtgagtg agccttggag 30

<210> SEQ ID NO 59
<211> LENGTH: 24
<212> TYPE: DNA
<213> ORGANISM: Artificial Sequence
<220> FEATURE:
<223> OTHER INFORMATION: PCR primer

<400> SEQUENCE: 59
cacacagaat tcattaaaga ggag 24

<210> SEQ ID NO 60
<211> LENGTH: 62
<212> TYPE: DNA
<213> ORGANISM: Artificial Sequence
<220> FEATURE:
<223> OTHER INFORMATION: PCR primer

<400> SEQUENCE: 60
cataatcaaa ctcaaagtca accatataag atctcctcct tacttcatga agaatcccct 60
cc 62

<210> SEQ ID NO 61
<211> LENGTH: 62
<212> TYPE: DNA
<213> ORGANISM: Artificial Sequence
<220> FEATURE:
<223> OTHER INFORMATION: PRC primer

<400> SEQUENCE: 61
ggaggggatt cttcatgaag taaggaggag atcttatatg gttgactttg agtttgatta 60
tg 62

<210> SEQ ID NO 62
<211> LENGTH: 51
<212> TYPE: DNA
<213> ORGANISM: Artificial Sequence
<220> FEATURE:
<223> OTHER INFORMATION: PCR primer

<400> SEQUENCE: 62
cgtgttactc attttgtctc ctcgtcattt acttgaagtc tgctaagata c 51

<210> SEQ ID NO 63
<211> LENGTH: 51
<212> TYPE: DNA
<213> ORGANISM: Artificial Sequence
<220> FEATURE:
<223> OTHER INFORMATION: PCR primer

<400> SEQUENCE: 63
gtatcttagc agacttcaag taaatgacga ggagacaaaa tgagtaacac g 51

-continued

```
<210> SEQ ID NO 64
<211> LENGTH: 60
<212> TYPE: DNA
<213> ORGANISM: Artificial Sequence
<220> FEATURE:
<223> OTHER INFORMATION: PCR primer

<400> SEQUENCE: 64

tcattcaccc gtgaggccat gaatatatct ccttcttaag cttagtgctt ctgacggtac     60


<210> SEQ ID NO 65
<211> LENGTH: 60
<212> TYPE: DNA
<213> ORGANISM: Artificial Sequence
<220> FEATURE:
<223> OTHER INFORMATION: PCR primer

<400> SEQUENCE: 65

gtaccgtcag aagcactaag cttaagaagg agatatattc atggcctcac gggtgaatga     60


<210> SEQ ID NO 66
<211> LENGTH: 32
<212> TYPE: DNA
<213> ORGANISM: Artificial Sequence
<220> FEATURE:
<223> OTHER INFORMATION: PCR primer

<400> SEQUENCE: 66

gactagatat ctcaggagta ctcatgggtg aa                                   32
```

ALANINE 2,3-AMINOMUTASE

CROSS-REFERENCE TO RELATED APPLICATIONS

This is the U.S. National Stage of International Application No. PCT/US03/01635, filed Jan. 17, 2003 (published in English under PCT Article 21(2)), which in turn claims the benefit of U.S. Patent Applications 60/350,727 filed Jan. 18, 2002 and 60/375,785 filed Apr. 25, 2002.

FIELD

This disclosure relates to alanine 2,3-aminomutase nucleic acid and amino acid sequences, cells having alanine 2,3-aminomutase activity which can convert alpha-alanine to beta-alanine, and methods using these cells to make beta-alanine, pantothenic acid, 3-hydroxypropionic acid, and other organic compounds.

BACKGROUND

Organic chemicals such as organic acids, esters, and polyols can be used to synthesize plastic materials and other products. To meet the increasing demand for organic chemicals, more efficient and cost-effective production methods are being developed which utilize raw materials based on carbohydrates rather than hydrocarbons. For example, certain bacteria have been used to produce large quantities of lactic acid used in the production of polylactic acid.

3-hydroxypropionic acid (3-HP) is an organic acid. Several chemical synthesis routes have been described to produce 3-HP, and biocatalytic routes have also been disclosed (WO 01/16346 to Suthers et al). 3-HP has utility for specialty synthesis and can be converted to commercially important intermediates by known art in the chemical industry, e.g., acrylic acid by dehydration, malonic acid by oxidation, esters by esterification reactions with alcohols, and 1,3-propanediol by reduction.

SUMMARY

The compound 3-hydroxypropionic acid (3-HP) can be produced biocatalyticly from PEP or pyruvate, through a key beta-alanine intermediate (FIG. 1). Beta-alanine can be synthesized in cells from carnosine, beta-alanyl arginine, beta-alanyl lysine, uracil via 5,6-dihydrouracil and N-carbamoyl-beta-alanine, N-acetyl-beta-alanine, anserine, or aspartate (FIGS. 1 and 2). However, these routes are relatively inefficient because they require rare precursors or starting compounds that are more valuable than 3-HP.

Therefore, production of 3-HP using biocatalytic routes would be more efficient if alpha-alanine could be converted to beta-alanine directly (FIG. 1). Unfortunately, an enzyme that interconverts alpha-alanine to beta-alanine has not yet been identified. It would be advantageous if enzymatic activities that carry out the conversion of alpha-alanine to beta-alanine were identified, such as an alanine 2,3-aminomutase.

Herein disclosed are alanine 2,3-aminomutase nucleic acid sequences (such as SEQ ID NOS: 20 and 29), amino acid sequences (such as SEQ ID NOS: 21 and 30), as well as variants, fragments, fusions, and polymorphisms thereof that retain alanine 2,3-aminomutase activity. In one example, the polypeptide is a sequence that includes SEQ ID NO: 21 or 30, or variants, fragments, or fusions thereof that retain alanine 2,3-aminomutase activity. In one example, the polypeptide is a mutated lysine 2,3-aminomutase and/or a lysine 5,6-aminomutase amino acid sequence. The disclosed sequences can be used to transform cells, such that the transformed cells have alanine 2,3-aminomutase activity, which allows the cells to produce beta-alanine from alpha-alanine. Binding agents that specifically bind to an alanine 2,3-aminomutase are encompassed by this disclosure.

Cells having alanine 2,3-aminomutase activity, which allow the cell to convert alpha-alanine to beta-alanine, are disclosed. Such cells can be eukaryotic or prokaryotic cells, such as yeast cells, plant cells, *Lactobacillus, Lactococcus, Bacillus*, or *Escherichia* cells. In one example, the cell is transformed with a mutated lysine 2,3-aminomutase and/or a mutated lysine 5,6-aminomutase that confers to the transformed cells alanine 2,3-aminomutase activity. In another example, transformed cells include an alanine 2,3-aminomutase, such as SEQ ID NO: 21 or 30. The disclosed cells can be used to produce nucleic acid molecules, polypeptides, and organic compounds. The polypeptides can be used to catalyze the formation of organic compounds or can be used as antigens to create specific binding agents.

A production cell having at least one exogenous nucleic acid, such as a nucleic acid encoding for an alanine 2,3-aminomutase, is disclosed. In one example, the nucleic acid sequence includes SEQ ID NOS: 20 or 29 (or fragments, variants, or fusions thereof that retain alanine 2,3-aminomutase activity). In another example, the nucleic acid sequence encodes an amino acid sequence shown in SEQ ID NO: 21 or 30 (or fragments, variants or fusion proteins that of that retain alanine 2,3-aminomutase activity). Production cells can be used to express polypeptides that have an enzymatic activity such as CoA transferase activity, beta-alanine ammonia lyase activity, 3-hydroxypropionyl-CoA (3-HP-CoA) dehydratase activity, glutamate dehydrogenase, 3-hydroxypropionyl-CoA hydrolase, alanine dehydrogenase, pyruvate-glutamate transaminase, and/or 3-hydroxyisobutyryl-CoA hydrolase activity. In another example, production cells are used to express polypeptides that have an enzymatic activity such as beta-alanine-2-oxoglutarate aminotransferase and 3-HP dehydrogenase and/or 3-hydroxyisbutyrate dehydrogenase. Methods of producing polypeptides encoded by the nucleic acid sequences described above are disclosed.

A method of identifying a cell having alanine 2,3-aminomutase activity is disclosed. The method includes culturing a cell, which is functionally deleted for panD, in media which does not include beta-alanine nor pantothenate. For example, the cell can produce alpha-alanine from media sources of carbon, oxygen, hydrogen, and nitrogen, but which does not include beta-alanine. Cells capable of growing in the media are identified, wherein cell growth indicates that the cell is producing beta-alanine from alpha-alanine, which indicates the cell has alanine 2,3-aminomutase activity. In contrast, absence of cell growth indicates that the cell is not producing beta-alanine from alpha-alanine, which indicates the cell does not have alanine 2,3-aminomutase activity. In one example, prior to culturing the cell for selection, cells are transformed with one or more mutated lysine 2,3-aminomutases and/or lysine 5,6-aminomutases.

A method of producing a polypeptide having alanine 2,3-aminomutase activity is disclosed. In one example, the method includes culturing cells having at least one exogenous nucleic acid molecule that encodes an alanine 2,3-aminomutase (such as SEQ ID NOS: 20 and 29), which is capable of producing beta-alanine from alpha-alanine.

Several methods of producing 3-HP from beta-alanine using the disclosed cells having alanine 2,3-aminomutase activity are disclosed. In one example, the cell is transfected with one or more enzymes necessary to convert 3-HP from beta-alanine. In another example, the method includes purifying beta-alanine from the cell, then contacting the beta-alanine with polypeptides necessary to convert 3-HP from beta-alanine.

The cells, alanine 2,3-aminomutase nucleic and amino acid sequences (such as SEQ ID NOS: 20, 21, 29, and 30), and methods disclosed herein, can be used to produce pantothenate, 3-HP, and derivatives thereof such as coenzyme A (CoA), and other organic compounds such as 1,3-propanediol, acrylic acid, polymerized acrylate, esters of acrylate, polymerized 3-HP, co-polymers of 3-HP and other compounds such as butyrates, valerates and other compounds, esters of 3-HP, and malonic acid and its esters. 3-HP is both biologically and commercially important. For example, the nutritional industry can use 3-HP as a food, feed additive or preservative, while the derivatives mentioned above can be produced from 3-HP.

Nucleic acid molecules encoding for an alanine 2,3-aminomutase (such as SEQ ID NOS: 20 and 29) can be used to engineer host cells with the ability to produce 3-HP as well as other organic compounds such as those listed above. Alanine 2,3-aminomutase peptides (such as SEQ ID NOS: 21 and 30) can be used in cell-free systems to make 3-HP as well as other organic compounds such as those listed above. The cells described herein can be used in culture systems to produce large quantities of 3-HP as well as other organic compounds such as those listed above.

One aspect of the disclosure provides cells, which in addition to alanine 2,3-aminomutase activity, include other enzyme activities, such as CoA transferase activity, beta-alanyl-CoA ammonia lyase activity, and 3-hydroxypropionyl-CoA dehydratase activity. In addition, methods of making products from these cells are disclosed. In some examples, the cell also includes one or more exogenous nucleic acid molecules that encodes one or more polypeptides having: glutamate dehydrogenase activity, CoA transferase activity, 3-hydroxypropionyl-CoA hydrolase, and/or 3-hydroxyisobutyryl-CoA hydrolase activity, and alanine dehydrogenase or pyruvate-glutamate transaminase activity. In another example, the cell also includes 4-aminobutyrate and/or beta-alanine-2-oxoglutarate aminotransferase activity and 3-HP dehydrogenase activity and/or 3-hydroxyisobutyrate dehydrogenase activity. Additionally, the cell can include, CoA hydrolase activity, poly hydroxyacid synthase activity, and/or lipase or esterase activity.

In another example, a cell including alanine 2,3-aminomutase activity; CoA transferase activity; beta-alanyl-CoA ammonia lyase activity; alanine dehydrogenase or pyruvate-glutamate transaminase activity, and 3-HP-CoA dehydratase activity, produces a product, for example, 3-HP, and/or an ester of 3-HP, such as methyl 3-hydroxypropionate, ethyl 3-hydroxypropionate, propyl 3-hydroxypropionate, and/or butyl 3-hydroxypropionate. In some examples, the cell further includes glutamate dehydrogenase activity, CoA transferase activity, 3-hydroxypropionyl-CoA hydrolase, and/or 3-hydroxyisobutyryl-CoA hydrolase activity. Accordingly, the disclosure also provides methods of producing one or more of these products. These methods involve culturing the cell that includes CoA transferase activity; beta-alanyl-CoA ammonia lyase activity; 3-HP-CoA dehydratase activity and in some examples glutamate dehydrogenase activity, CoA transferase activity, 3-hydroxypropionyl-CoA hydrolase, 3-hydroxyisobutryl-CoA hydrolase activity, and/or alanine dehydrogenase or pyruvate-glutamate transaminase activity, under conditions that allow the product to be produced. These cells also can include lipase or esterase activity.

Another aspect of the disclosure provides cells, which in addition to alanine 2,3-aminomutase activity, have CoA transferase activity; beta-alanyl-CoA ammonia lyase activity; 3-hydroxypropionyl-CoA dehydratase activity; and poly hydroxyacid synthase activity. In some examples, these cells can contain an exogenous nucleic acid molecule that encodes one or more polypeptides having: CoA transferase activity; beta-alanyl-CoA ammonia lyase activity; 3-hydroxypropionyl-CoA dehydratase activity; alanine dehydrogenase or pyruvate-glutamate transaminase activity, and poly hydroxyacid synthase activity. This cell can be used, for example, to produce products such as polymerized 3-HP and co-polymers of 3-HP and other compounds such as butyrates, valerates and other compounds.

In another example, the cell, which in addition to alanine 2,3-aminomutase activity, has CoA transferase activity; beta-alanyl-CoA ammonia lyase activity; alanine dehydrogenase or pyruvate-glutamate transaminase activity, and poly hydroyxacid synthase activity, which can produce a product, for example, polymerized 3-HP. In some examples, these cells can contain one or more exogenous nucleic acid molecules that encode one or more of polypeptides having CoA transferase activity; beta-alanyl-CoA ammonia lyase activity; and/or poly hydroxyacid synthase activity.

Another aspect of the disclosure provides a cell including alanine 2,3-aminomutase activity, CoA transferase activity, beta-alanyl-CoA ammonia lyase activity, alanine dehydrogenase or pyruvate-glutamate transaminase activity, and lipase or esterase activity. In one example, the cell also includes CoA hydrolase activity. In some examples, the cell contains an exogenous nucleic acid molecule that encodes one or more polypeptides having CoA transferase activity; beta-alanyl-CoA ammonia lyase activity; lipase or esterase activity and/or CoA hydrolase activity. This cell can be used, among other things, to produce products such as esters of acrylate (e.g., methyl acrylate, ethyl acrylate, propyl acrylate, and butyl acrylate).

Cells which can produce 1,3-propanediol, and methods of their use are disclosed. 1,3-propanediol can be generated from either 3-HP-CoA or 3-HP via the use of polypeptides having enzymatic activity. When converting 3-HP-CoA to 1,3-propanediol, polypeptides having oxidoreductase activity or reductase activity, such as polypeptides having acetylating aldehyde:NAD(+) oxidoreductase and alcohol:NAD (+) oxidoreductase activities (e.g., enzymes from the 1.1.1.1 and/or 1.2.1.10 class of enzymes) can be used. When making 1,3-propanediol from 3-HP, a combination of a polypeptide having aldehyde dehydrogenase activity (e.g., an enzyme from the 1.2.1-class) and a polypeptide having alcohol dehydrogenase activity (e.g., an enzyme from the 1.1.1.-class) can be used, such as aldehyde dehydrogenase (NAD (P)+) (EC 1.2.1.-) and alcohol dehydrogenase (EC 1.1.1.1).

In some examples, products are produced in vitro (outside of a cell). In other examples, products are produced using a combination of in vitro and in vivo (within a cell) methods. In yet other examples, products are produced in vivo. For methods involving in vivo steps, the cells can be isolated cultured cells or whole organisms such as transgenic plants, non-human mammals, or single-celled organisms such as yeast and bacteria (e.g., *Lactobacillus, Lactococcus, Bacillus*, and *Escherichia* cells). Hereinafter such cells are referred to as production cells. Products produced by these production cells can be organic products such as beta-alanine, 3-HP, pantothenate, and derivatives thereof such as organic acids, polyols (i.e. 1,3-propanediol), coenzyme A (CoA), as well as an alanine 2,3-aminomutase described herein.

Pantothenate, a vitamin essential to many animals for growth and health, is involved in fatty acid synthesis and degradation. Deficiency of the vitamin results in generalized malaise clinically. Therefore, pantothenate produced using the methods disclosed herein can be administered to a subject having a pantothenic deficiency, at a therapeutically effective dose. Cells that produce pantothenate, and methods of producing pantothenate from beta-alanine using the disclosed cells, are disclosed.

Production cells used to produce pantothenate and/or CoA, can be used to express alpha-ketopantoate hydroxymethyltransferase (E.C. 2.1.2.11), alpha-ketopantoate reductase (E.C. 1.1.1.169), and pantothenate synthase (E.C. 6.3.2.1), to produce pantothenate, or in addition pantothenate kinase (E.C. 2.7.1.33), 4'-phosphopantethenoyl-1-cysteine synthetase (E.C. 6.3.2.5), 4'-phosphopantothenoylcysteine decarboxylase (E.C. 4.1.1.36), ATP:4'-phosphopantetheine adenyltransferase (E.C. 2.7.7.3), and dephospho-CoA kinase (E.C. 2.7.1.24), to produce coenzyme A.

BRIEF DESCRIPTION OF THE FIGURES

FIG. 4 is an alignment of a *B. subtilis* wild-type lysine 2,3-aminomutase (KAM, SEQ ID NO: 31), and a mutated form thereof which encodes an alanine 2,3-aminomutase (SEQ ID NO: 21). Substitutions are shown in bold. The Fe-S cluster-binding motif is underlined, and the putative PLP-binding motif is italicized.

FIG. 5 is an alignment of *P. gingivalis* wild-type lysine 2,3-aminomutase (kam, SEQ ID NO: 28) and a mutated form thereof which encodes an alanine 2,3-aminomutase (aam, SEQ ID NO: 30). Substitutions are shown in bold. The Fe-S cluster-binding motif is underlined, and the putative PLP-binding motif is italicized.

FIG. 6 is an alignment of a *B. subtilis* and *P. gingivalis* wild-type lysine 2,3-aminomutase (kam, SEQ ID NOS: 31 and 28), and a mutated form thereof which encodes an alanine 2,3-aminomutase (aam, SEQ ID NOS: 21 and 29). Substitutions with a common location are in bold.

SEQUENCE LISTING

Figure 1:
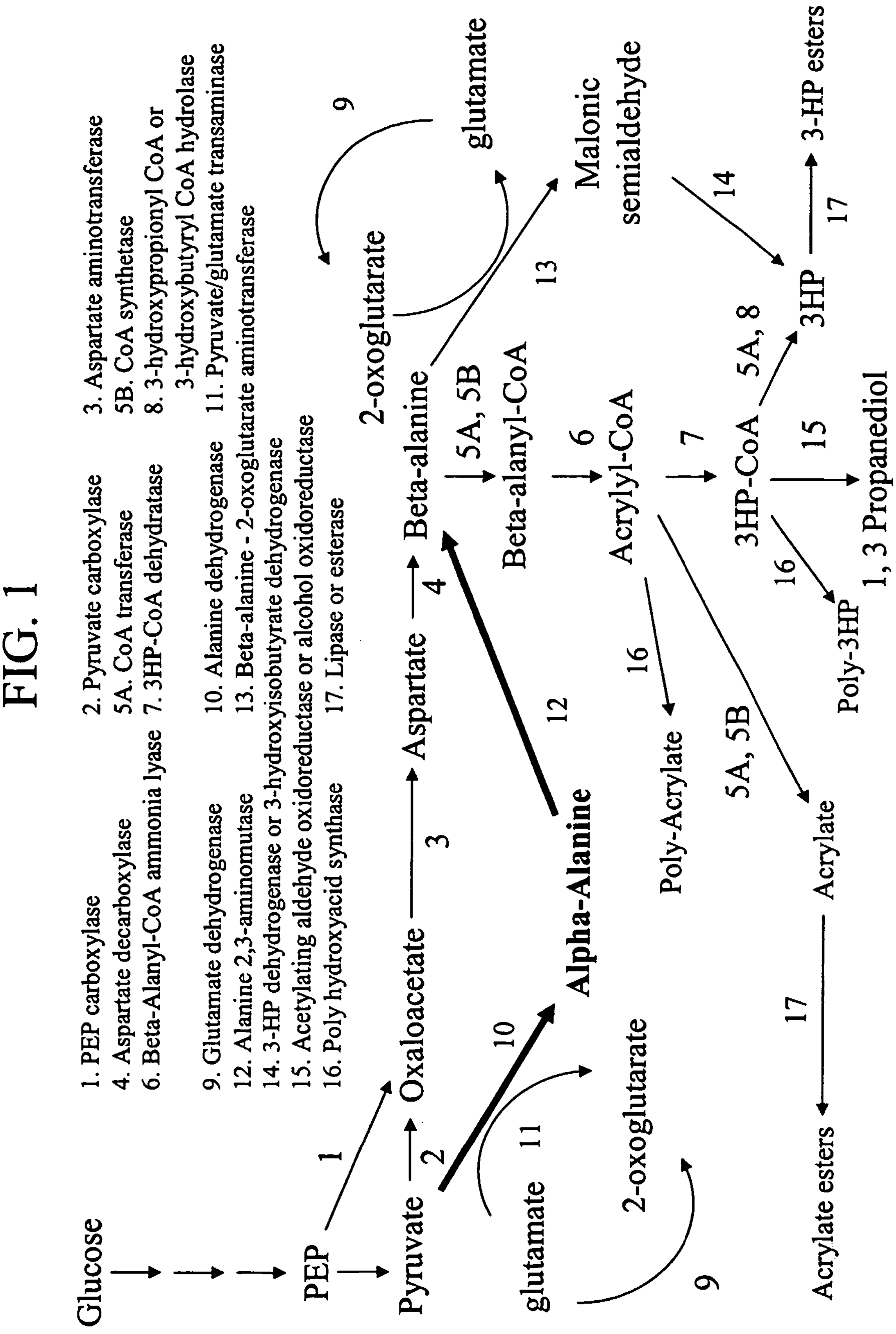
FIG. 1 is a diagram of a pathway for generating 3-HP and derivatives thereof via a beta-alanine intermediate, and for making beta-alanine from alpha-alanine.

The nucleic and amino acid sequences listed in the accompanying sequence listing are shown using standard letter abbreviations for nucleotide bases, and three letter code for amino acids.

Only one strand of each nucleic acid sequence is shown, but the complementary strand is understood as included by any reference to the displayed strand.

SEQ ID NOS: 1 and 2 are PCR primers used to clone a *B. subtilis* lysine 2,3-aminomutase (KAM) gene.

SEQ ID NO: 3 is a nucleic acid sequence of a *B. subtilis* KAM gene.

SEQ ID NOS: 4 and 5 are PCR primers used to amplify a CAT gene of pKD3.

SEQ ID NOS: 6 and 7 are PCR primers used to confirm correct insertion of the CAT gene into the panD locus.

SEQ ID NOS: 8 and 9 are nucleic acid sequences of primers used to amplify the CAT gene of pKD3.

SEQ ID NOS: 10 and 11 are nucleic acid sequences of primers used to generate an L103M mutation in the wildtype *B. subtilis* lysine 2,3-aminomutase gene.

SEQ ID NOS: 12 and 13 are nucleic acid sequences of primers used to generate an M136V mutation in the wildtype *B. subtilis* lysine 2,3-aminomutase gene.

SEQ ID NOS: 14 and 15 are nucleic acid sequences of primers used to generate an D339H mutation in the wildtype *B. subtilis* lysine 2,3-aminomutase gene.

SEQ ID NOS: 16-19, 26, 27 and 32 are nucleic acid sequences of primers used to clone a 3-HP dehydrogenase gene from *Alcaligenes faecalis* M3A.

SEQ ID NO: 20 is a nucleic acid sequence of an alanine 2,3-aminomutase DNA.

SEQ ID NO: 21 is an amino acid sequence of an alanine 2,3-aminomutase protein.

SEQ ID NO: 22 is a nucleic acid sequence of a beta-alanyl-CoA ammonia lyase (ACL-1) cDNA.

SEQ ID NO: 23 is an amino acid sequence of a beta-alanyl-CoA ammonia lyase (ACL-1) protein.

SEQ ID NO: 24 is a nucleic acid sequence of a CoA transferase cDNA.

SEQ ID NO: 25 is an amino acid sequence of a CoA transferase protein.

SEQ ID NO: 28 is an amino acid sequence of a *P. gingivalis* KAM.

SEQ ID NO: 29 is a nucleic acid sequence of an alanine 2,3-aminomutase.

SEQ ID NO: 30 is an amino acid sequence of an alanine 2,3-aminomutase protein.

SEQ ID NO: 31 is an amino acid sequence of a *B. subtilis* KAM.

SEQ ID NO: 33 is an nucleic acid sequence of a 3-HP dehydrogenase gene from *Alcaligenes faecalis* M3A.

SEQ ID NO: 34 is an amino acid sequence of a 3-HP dehydrogenase gene from *Alcaligenes faecalis* M3A.

SEQ ID NOS: 35-37 are nucleic acid sequences of primers used to clone beta-alanine-CoA ammonia lyase (ACL-1 and ACL-2).

SEQ ID NOS: 38-40 are nucleic acid sequences of primers used to clone CoA transferase from *E. coli.*

SEQ ID NOS: 41-48 are nucleic acid sequences of primers used to generate operons 1 and 2 which include ACL-1 or ACL-2, CoA transferase and CoA hydratase genes.

SEQ ID NOS: 49-52 are nucleic acid sequences of primers used to generate operon 3 which includes 4-aminobutyrate aminotransferase and 3-hydroxyisobutyrate dehydrogenase genes.

SEQ ID NO: 53 is a nucleic acid sequence of a beta-alanyl-CoA ammonia lyase (ACL-2) cDNA.

SEQ ID NO: 54 is an amino acid sequence of a beta-alanyl-CoA ammonia lyase (ACL-2) protein.

SEQ ID NOS: 55-56 are nucleic acid sequences of primers used to amplify the ATH-2 operon from the pATH-2-2-1 plasmid.

SEQ ID NOS: 57-58 are nucleic acid sequences of primers used to amplify the ATD operon from the pATD plasmid.

SEQ ID NOS: 59-60 are nucleic acid sequences of primers used to amplify a *B. subtilis* alanine 2,3 aminomutase.

SEQ ID NOS: 61-62 are nucleic acid sequences of primers used to amplify a rat beta-alanine aminotransferase gene.

SEQ ID NOS: 63-64 are nucleic acid sequences of primers used to amplify a 3-HP dehydrogenase from *A. faecalis.*

SEQ ID NOS: 65-66 are nucleic acid sequences of primers used to amplify an alpha-alanine aminotransferase gene from rat.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a protein" includes one or a plurality of such proteins, and reference to "comprising the cell" includes reference to one or more cells and equivalents thereof known to those skilled in the art, and so forth.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features and advantages of the disclosure are apparent from the following detailed description and the claims.

Alanine 2,3-aminomutase: An enzyme which can convert alpha-alanine to beta-alanine, for example in a cell. Includes any alanine 2,3-aminomutase gene, cDNA, RNA, or protein from any organism, such as a prokaryote. In one example, an alanine 2,3-aminomutase is a mutated lysine 2,3-aminomutase or a mutated lysine 5,6-aminomutase which has alanine 2,3-aminomutase activity: Lysine 2,3-aminomutases (or genes annotated in genetic databases as lysine 2,3 aminomutase) can be obtained from any organism, such as a prokaryote, for example *Bacillus subtilis, Deinococcus radiodurans, Clostridium subterminale, Porphyromonas gingivalis* or *E. coli*, and mutated using any method known in the art.

In particular examples, an alanine 2,3-aminomutase nucleic acid sequence includes the sequence shown in SEQ ID NOS: 20 or 29, or fragments, variants, or fusions thereof that retain the ability to encode a peptide or protein having alanine 2,3-aminomutase activity. In another example, an alanine 2,3-aminomutase protein includes the amino acid sequence shown in SEQ ID NO: 21 or 30, or fragments, fusions, or variants thereof that retain alanine 2,3-aminomutase activity.

In another example, an alanine 2,3-aminomutase sequence includes a full-length wild-type sequence, such as SEQ ID NO: 21 or 30, as well as shorter sequences which retain the ability to convert alpha-alanine to beta-alanine, such as amino acids 50-390 of SEQ ID NO: 21, amino acids 101-339 of SEQ ID NO: 21, amino acids 15-390 of SEQ ID NO: 30, and amino acids 15-340 of SEQ ID NO 30. This description includes alanine 2,3-aminomutase allelic variants, as well as any variant, fragment, or fusion sequence which retains the ability to convert alpha-alanine to beta-alanine.

Alanine 2,3-aminomutase activity: The ability of an alanine 2,3-aminomutase to convert alpha-alanine to beta-alanine. In one example, such activity occurs in a cell. In another example, such activity occurs in vitro. Such activity can be measured using any assay known in the art, for example the screening assays and enzyme assays described in EXAMPLES 6 and 9-11. In addition, an enzyme with alanine 2,3-aminomutase activity can be identified by incubating the enzyme with either alpha-alanine or beta-alanine and determining the reaction products by high-performance liquid chromatography (for example using the method of, Abe et al. *J. Chromatography B,* 712:43-9, 1998). In one example, it is the ability of an alanine 2,3-aminomutase to convert alpha-alanine to beta-alanine in an *E. coli* mutant functionally deleted for the panD gene.

Antibody: A molecule including an antigen binding site which specifically binds (immunoreacts with) an antigen. Examples include polyclonal antibodies, monoclonal antibodies, humanized monoclonal antibodies, or immunologically effective portions thereof.

Includes immunoglobulin molecules and immunologically active portions thereof. Naturally occurring antibodies (e.g., IgG) include four polypeptide chains, two heavy (H) chains and two light (L) chains inter-connected by disulfide bonds. However, the antigen-binding function of an antibody can be performed by fragments of a naturally occurring antibody. Immunologically effective portions of monoclonal antibodies include, but are not limited to: Fab, Fab', $F(ab')_2$, Fabc and Fv portions (for a review, see Better and Horowitz, *Methods. Enzymol.* 1989, 178:476-96). Other examples of antigen-binding fragments include, but are not limited to: (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment which consists of a VH domain; (v) an isolated complimentarity determining region (CDR); and (vi) an $F(ab')_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv) by recombinant methods. Such single chain antibodies are also included.

"Specifically binds" refers to the ability of a particular agent (a "specific binding agent") to specifically react with a particular analyte, for example to specifically immunoreact with an antibody, or to specifically bind to a particular peptide sequence. The binding is a non-random binding reaction, for example between an antibody molecule and an antigenic determinant. Binding specificity of an antibody is typically determined from the reference point of the ability of the antibody to differentially bind the specific antigen and an unrelated antigen, and therefore distinguish between two different antigens, particularly where the two antigens have unique epitopes. An antibody that specifically binds to a particular epitope is referred to as a "specific antibody".

Monoclonal or polyclonal antibodies can be produced to an alanine 2,3-aminomutase polypeptide (such as SEQ ID NO: 21 and/or 30), fragments of an alanine 2,3-aminomutase polypeptide (such as amino acids 50-390 of SEQ ID NO: 21, for example amino acids 101-339 of SEQ ID NO: 21, or amino acids 15-390 of SEQ ID NO: 30, for example amino acids 15-331 of SEQ ID NO: 30), or variants, fusions, or fragments thereof. Optimally, antibodies raised against one or more epitopes on a polypeptide antigen will specifically detect that polypeptide. That is, antibodies raised against one particular polypeptide would recognize and bind that particular polypeptide, and would not substantially recognize or bind to other polypeptides. The determination that an antibody specifically binds to a particular polypeptide is made by any one of a number of standard immunoassay methods; for instance, Western blotting (See, e.g., Sambrook et al. (ed.), Molecular Cloning: A Laboratory Manual, 2nd ed., vol. 1-3, Cold Spring Harbor Laboratory Press, Cold Spring Harbor, N.Y., 1989).

To determine that an antibody preparation (such as a preparation produced in a mouse against an alanine 2,3-aminomutase polypeptide, for example SEQ ID NO: 21 or 30) specifically detects the appropriate polypeptide (e.g., an alanine 2,3-aminomutase polypeptide) by Western blotting, total cellular protein can be extracted from cells and separated by SDS-polyacrylamide gel electrophoresis. The separated total cellular protein can then be transferred to a membrane (e.g., nitrocellulose), and the antibody preparation incubated with the membrane. After washing the membrane to remove non-specifically bound antibodies, the presence of specifically bound antibodies can be detected using an appropriate secondary antibody (e.g., an anti-mouse antibody) conjugated to an enzyme such as alkaline phosphatase since application of 5-bromo-4-chloro-3-indolyl phosphate/nitro blue tetrazolium results in the production of a densely blue-colored compound by immunolocalized alkaline phosphatase.

Substantially pure polypeptides suitable for use as an immunogen can be obtained from transfected cells, transformed cells, or wild-type cells. Polypeptide concentrations in the final preparation can be adjusted, for example, by concentration on an Amicon filter device, to the level of a few micrograms per milliliter. In addition, polypeptides ranging in size from full-length polypeptides to polypeptides having as few as nine amino acid residues can be utilized as immunogens. Such polypeptides can be produced in cell culture, can be chemically synthesized using standard methods, or can be obtained by cleaving large polypeptides into smaller polypeptides that can be purified. Polypeptides having as few as nine amino acid residues in length can be immunogenic when presented to an immune system in the context of a Major Histocompatibility Complex (MHC) molecule such as an MHC class I or MHC class II molecule. Accordingly, polypeptides having at least 9, 10, 11, 12, 13, 14, 15, 20, 25, 30, 35, 40, 45, 50, 55, 60, 70, 80, 90, 100, 150, 200, 250, 300, 350, 400, 450, 500, 550, 600, 650, 700, 750, 800, 900, 1000, 1050, 1100, 1150, 1200, 1250, 1300, 1350, or more consecutive amino acid residues of an alanine 2,3-aminomutase polypeptide can be used as immunogens for producing antibodies.

Monoclonal antibodies to any of the polypeptides disclosed herein can be prepared from murine hybridomas according to the classic method of Kohler & Milstein (Nature 256:495, 1975) or a derivative method thereof.

Polyclonal antiserum containing antibodies to the heterogeneous epitopes of any polypeptide disclosed herein can be prepared by immunizing suitable animals with the polypeptide (or fragment, fusion, or variant thereof), which can be unmodified or modified to enhance immunogenicity. An effective immunization protocol for rabbits can be found in Vaitukaitis et al. (*J. Clin. Endocrinol. Metab.* 33:988-91, 1971).

Antibody fragments can be used in place of whole antibodies and can be readily expressed in prokaryotic host cells. Methods of making and using immunologically effective portions of monoclonal antibodies, also referred to as "antibody fragments," are well known and include those described in Better & Horowitz (*Methods Enzymol.* 178:476-96, 1989), Glockshuber et al. (*Biochemistry* 29:1362-7, 1990), U.S. Pat. No. 5,648,237 ("Expression of Functional Antibody Fragments"), U.S. Pat. No. 4,946,778 ("Single Polypeptide Chain Binding Molecules"), U.S. Pat. No. 5,455,030 ("Immunotherapy Using Single Chain Polypeptide Binding Molecules"), and references cited therein.

Antigen: A compound, composition, or substance that can stimulate the production of antibodies or a T-cell response in an animal, including compositions that are administered, such as injected or absorbed, to an animal. An antigen reacts with the products of specific humoral or cellular immunity, including those induced by heterologous immunogens. The term "antigen" includes all related antigenic epitopes.

cDNA (complementary DNA): A piece of DNA lacking internal, non-coding segments (introns) and regulatory sequences which determine transcription. cDNA can be synthesized in the laboratory by reverse transcription from messenger RNA extracted from cells.

Conservative substitution: One or more amino acid substitutions (for example 1, 2, 5 or 10 residues) for amino acid residues having similar biochemical properties. Typically, conservative substitutions have little to no impact on the activity of a resulting polypeptide. For example, a conservative substitution is an amino acid substitution in an alanine 2,3-aminomutase peptide that does not substantially affect the ability of the peptide to convert alpha-alanine to beta-alanine. In a particular example, a conservative substitution is an amino acid substitution in an alanine 2,3-aminomutase peptide, such as a conservative substitution in SEQ ID NO: 21 or 30, that does not significantly alter the ability of the protein to convert alpha-alanine to beta-alanine. Methods that can be used to determine alanine 2,3-aminomutase activity are disclosed herein (EXAMPLES 6 and 9-11). An alanine scan can be used to identify which amino acid residues in an alanine 2,3-aminomutase peptide can tolerate an amino acid substitution. In one example, alanine 2,3-aminomutase activity is not altered by more than 25%, for example not more than 20%, for example not more than 10%, when an alanine, or other conservative amino acid (such as those listed below), is substituted for one or more native amino acids.

In one example, one conservative substitution is included in the peptide, such as a conservative substitution in SEQ ID NO: 21 or 30. In another example, 10 or less conservative substitutions are included in the peptide, such as five or less. A polypeptide can be produced to contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using standard peptide synthesis methods.

Substitutional variants are those in which at least one residue in the amino acid sequence has been removed and a different residue inserted in its place. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gin; Asp for Glu; Pro for Gly; Asn or Gin for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Further information about conservative substitutions can be found in, among other locations in, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988), WO 00/67796 (Curd et al.) and in standard textbooks of genetics and molecular biology.

Deletion: The removal of a sequence of a nucleic acid, for example DNA, the regions on either side being joined together.

Detectable: Capable of having an existence or presence ascertained. For example, production of beta-alanine from alpha-alanine is detectable if the signal generated from the beta-alanine is strong enough to be measurable.

DNA: Deoxyribonucleic acid. DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Exogenous: The term "exogenous" as used herein with reference to nucleic acid and a particular cell refers to any nucleic acid that does not originate from that particular cell as found in nature. Thus, a non-naturally-occurring nucleic acid is considered to be exogenous to a cell once introduced into the cell. A nucleic acid that is naturally-occurring also can be exogenous to a particular cell. For example, an entire chromosome isolated from a cell of person X is an exogenous nucleic acid with respect to a cell of person Y once that chromosome is introduced into Y's cell.

Functional deletion: A mutation, partial or complete deletion, insertion, or other variation made to a gene sequence which inhibits production of the gene product, and/or renders the gene product non-functional. For example, functional deletion of panD in *E. coli* prevents the production of β-alanine from aspartate by aspartate decarboxylase, which is encoded by the panD gene. This functional deletion of panD in *E. coli* inactivates aspartate decarboxylase which results in growth inhibition of the *E. coli* in the absence of beta-alanine or pantothenate in the growth medium.

Functionally Equivalent: Having an equivalent function. In the context of a alanine 2,3-aminomutase molecule, functionally equivalent molecules include different molecules that retain the function of alanine 2,3-aminomutase. For example, functional equivalents can be provided by sequence alterations in an alanine 2,3-aminomutase, wherein the peptide with one or more sequence alterations retains a function of the unaltered peptide, such that it retains its ability to convert alpha-alanine to beta-alanine.

Examples of sequence alterations include, but are not limited to, conservative substitutions, deletions, mutations, frameshifts, and insertions. In one example, a given polypeptide binds an antibody, and a functional equivalent is a polypeptide that binds the same antibody. Thus a functional equivalent includes peptides that have the same binding specificity as a polypeptide, and that can be used as a reagent in place of the polypeptide (such as in the production of pantothenic acid and 3-HP). In one example a functional equivalent includes a polypeptide wherein the binding sequence is discontinuous, wherein the antibody binds a linear epitope. Thus, if the peptide sequence is MKNKWYKPKR (amino acids 1-10 of SEQ ID NO: 21) a functional equivalent includes discontinuous epitopes, that can appear as follows (=any number of intervening amino acids): $NH_2$--MKNKWYKPK**R—COOH. In this example, the polypeptide is functionally equivalent to amino acids 1-10 of SEQ ID NO: 21 if the three dimensional structure of the polypeptide is such that it can bind a monoclonal antibody that binds amino acids 1-10 of SEQ ID NO: 21.

Hybridization: A method of testing for complementarity in the nucleotide sequence of two nucleic acid molecules, based on the ability of complementary single-stranded DNA and/or RNA to form a duplex molecule. Nucleic acid hybridization techniques can be used to obtain an isolated nucleic acid within the scope of the disclosure. Briefly, any nucleic acid having some homology to an alanine 2,3-aminomutase (such as homology to SEQ ID NOS: 20 and 29 or variants or fragments thereof) can be used as a probe to identify a similar nucleic acid by hybridization under conditions of moderate to high stringency. Once identified, the nucleic acid then can be purified, sequenced, and analyzed to determine if it is an alanine 2,3-aminomutase having alanine 2,3-aminomutase activity.

Hybridization can be done by Southern or Northern analysis to identify a DNA or RNA sequence, respectively, that hybridizes to a probe. The probe can be labeled, for example with a biotin, a fluorophore, digoxygenin, an enzyme, or a radioisotope such as $^{32}$p. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39-7.52 of Sambrook et al., (1989) Molecular Cloning, second edition, Cold Spring Harbor Laboratory, Plainview, N.Y. Typically, a probe is at least about 20 nucleotides in length. For example, a probe including 20 contiguous nucleotides of an alanine 2,3-aminomutase (such as 20 contiguous nucleotides of SEQ ID NO: 20 or 29) can be used to identify an identical or similar nucleic acid. In addition, probes longer or shorter than 20 nucleotides can be used.

The disclosure also provides isolated nucleic acid sequences that are at least about 12 bases in length (e.g., at least about 13, 14, 15, 16, 17, 18, 19, 20, 25, 30, 40, 50, 60, 100, 250, 500, 750, 1000, 1400, 2000, 3000, 4000, or 5000 bases in length) and hybridize, under hybridization conditions, to the sense or antisense strand of an alanine 2,3-aminomutase nucleic acid sequence, for example SEQ ID NO: 20 or 29). The hybridization conditions can be moderately or highly stringent hybridization conditions.

Moderately stringent hybridization conditions are when the hybridization is performed at about 42° C. in a hybridization solution containing 25 mM $KPO_4$ (pH 7.4), 5×SSC, 5× Denhart's solution, 50 μg/ml denatured, sonicated salmon sperm DNA, 50% formamide, 10% Dextran sulfate, and 1-15 ng/mL probe (about $5\times10^7$ cpm/μg), while the washes are performed at about 50° C. with a wash solution containing 2×SSC and 0.1% sodium dodecyl sulfate.

Highly stringent hybridization conditions are when the hybridization is performed at about 42° C. in a hybridization solution containing 25 mM $KPO_4$ (pH 7.4), 5×SSC, 5× Denhart's solution, 50 μg/nL denatured, sonicated salmon sperm DNA, 50% formamide, 10% Dextran sulfate, and 1-15 ng/mL probe (about $5\times10^7$ cpm/μg), while the washes are performed at about 65° C. with a wash solution containing 0.2×SSC and 0.1% sodium dodecyl sulfate.

Isolated: An "isolated" biological component (such as a nucleic acid molecule or protein) has been substantially separated or purified away from other biological components in the cell of the organism in which the component naturally occurs, i.e., other chromosomal and extrachromosomal DNA and RNA, and proteins. Nucleic acids and proteins that have been "isolated" include nucleic acids and proteins purified by standard purification methods. The term also embraces nucleic acids and proteins prepared by recombinant expression in a host cell as well as chemically synthesized nucleic acids, proteins and peptides.

In one example, isolated refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

In one example, the term "isolated" as used with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

Leucine 2,3-aminomutase: An enzyme which can convert alpha-leucine to beta-leucine. Includes any leucine 2,3-aminomutase gene, cDNA, RNA, or protein from any organism, such as a prokaryote or eukaryote, for example from rat, human, chicken, or *Clostridium sporogenes* (Poston, *J. Biol. Chem.* 251:1859-63, 1976). This description includes leucine 2,3-aminomutase allelic variants, as well as any variant, fragment, or fusion protein sequence which retains the ability to convert alpha-leucine to beta-leucine.

Lysine 2,3-aminomutase: An enzyme which can convert alpha-lysine to beta-lysine. Includes any lysine 2,3-aminomutase gene, cDNA, RNA, or protein from any organism, such as a prokaryote, for example *Bacillus subtilis, Deinococcus radiodurans, Clostridium subterminale, Porphyromonas gingivalis, Aquifex aeolicus, Haemophilus influenzae*, or *E. coli*. This description includes lysine 2,3-aminomutase allelic variants, as well as any variant, fragment, or fusion sequence which retains the ability to convert alpha-lysine to beta-lysine. In one example, includes polypeptides encoded by genes annotated as lysine 2,3-aminomutase in public DNA sequence databases, such as GenBank.

Nucleic acid: Encompasses both RNA and DNA including, without limitation, cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

Oligonucleotide: A linear polynucleotide (such as DNA or RNA) sequence of at least 9 nucleotides, for example at least 15, 18, 24, 25, 27, 30, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide.

Pantothenate or Pantothenic Acid: A commercially significant vitamin which is used in cosmetics, medicine, and nourishment. The terms pantothenic acid and pantothenate are used interchangeably herein, and refer not only to the free acid but also to the salts of D-pantothenic acid, such as the calcium salt, sodium salt, ammonium salt or potassium salt. Pantothenate can be produced by chemical synthesis or biotechnologically from beta-alanine using the cells and methods disclosed herein.

Methods for measuring the amount of pantothenate are known (for example see U.S. Pat. No. 6,184,006 to Rieping et al. and U.S. Pat. No. 6,177,264 to Eggeling et al.). For example, a quantitative determination of D-pantothenate can be made by using the *Lactobacillus plantarum* pantothenate assay (test strain: *Lactobacillus plantarum* ATCC 8014, Cat. No. 3211-30-3; culture medium: Bacto pantothenate assay medium (DIFCO Laboratories, Michigan, USA), cat. No. 0604-15-3). This indicator strain can grow only in the presence of pantothenate in the indicated culture medium and displays a photometrically measurable, linear dependency of the growth on the concentration of pantothenate in the medium. The hemicalcium salt of pantothenate can be used for calibration (Sigma Catalog Number P 2250). The optical density can be determined at a wavelength of 580 nm.

Peptide Modifications: The present disclosure includes alanine 2,3-aminomutase peptides, as well as synthetic embodiments. In addition, analogues (non-peptide organic molecules), derivatives (chemically functionalized peptide molecules obtained starting with the disclosed peptide sequences) and variants (homologs) having alanine 2,3-aminomutase activity can be utilized in the methods described herein. The peptides disclosed herein include a sequence of amino acids, that can be either L- and/or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide. Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as F, Cl, Br or I, or with $C_1$-$C_6$ alkyl, $C_1$-$C_{16}$alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains, resulting in such peptido- and organomimetics of the proteins of this invention having detectable alanine 2,3-aminomutase activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included within the scope of the disclosure are mimetics prepared using such techniques. In one example, a mimetic mimics the alanine 2,3-aminomutase activity generated by an alanine 2,3-aminomutase or a variant, fragment, or fusion thereof.

Polynucleotide: A linear nucleic acid sequence of any length. Therefore, a polynucleotide includes molecules which are at least about 15, 25, 50, 75, 100, 200 or 400 (oligonucleotides) and also nucleotides as long as a full-length cDNA.

Probes and primers: A "probe" includes an isolated nucleic acid containing a detectable label or reporter molecule. Typical labels include radioactive isotopes, ligands, chemiluminescent agents, fluorophores, and enzymes. Methods for labeling and guidance in the choice of labels appropriate for various purposes are discussed in, for example, Sambrook et al. (ed.), Molecular Cloning: A Laboratory Manual 2nd ed., vol. 1-3, Cold Spring Harbor Laboratory Press, Cold Spring Harbor, N.Y., 1989, and Ausubel et al. (ed.) Current Protocols in Molecular Biology, Greene Publishing and Wiley-Interscience, New York (with periodic updates), 1987.

"Primers" are typically nucleic acid molecules having ten or more nucleotides (e.g., nucleic acid molecules having between about 10 nucleotides and about 100 nucleotides). A primer can be annealed to a complementary target nucleic acid strand by nucleic acid hybridization to form a hybrid between the primer and the target nucleic acid strand, and then extended along the target nucleic acid strand by, for example, a DNA polymerase enzyme. Primer pairs can be used for amplification of a nucleic acid sequence, for example, by the polymerase chain reaction (PCR) or other nucleic-acid amplification methods.

Methods for preparing and using probes and primers are described, for example, in references such as Sambrook et al. (ed.) Molecular Cloning: A Laboratory Manual, 2nd ed., vol. 1-3, Cold Spring Harbor Laboratory Press, Cold Spring Harbor, N.Y., 1989; Ausubel et al. (ed.), Current Protocols in Molecular Biology, Greene Publishing and Wiley-Interscience, New York (with periodic updates), 1987; and Innis et al., PCR Protocols: A Guide to Methods and Applications, Academic Press: San Diego, 1990. PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with the length, but that a probe or primer can range in size from a full-length sequence to sequences as short as five consecutive nucleotides. Thus, for example, a primer of 20 consecutive nucleotides can anneal to a target with a higher specificity than a corresponding primer of only 15 nucleotides. Thus, in order to obtain greater specificity, probes and primers can be selected that comprise, for example, 25, 30, 35, 40, 50, 60, 70, 80, 90, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, or more consecutive nucleotides.

Promoter: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Purified: The term purified does not require absolute purity; rather, it is intended as a relative term. Thus, for example, a purified peptide preparation is one in which the peptide or protein is more enriched than the peptide or protein is in its environment within a cell, such that the peptide is substantially separated from cellular components (nucleic acids, lipids, carbohydrates, and other polypeptides) that may accompany it. In another example, a purified peptide preparation is one in which the peptide is substantially-free from contaminants, such as those that might be present following chemical synthesis of the peptide.

In one example, an alanine 2,3-aminomutase peptide is purified when at least 50% by weight of a sample is composed of the peptide, for example when at least 60%, 70%, 80%, 85%, 90%, 92%, 95%, 98%, or 99% or more of a sample is composed of the peptide. Examples of methods that can be used to purify an antigen, include, but are not limited to the methods disclosed in Sambrook et al. (Molecular Cloning: A Laboratory Manual, Cold Spring Harbor, N.Y., 1989, Ch. 17). Protein purity can be determined by, for example, polyacrylamide gel electrophoresis of a protein sample, followed by visualization of a single polypeptide band upon staining the polyacrylamide gel; high-pressure liquid chromatography; sequencing; or other conventional methods.

Recombinant: A recombinant nucleic acid is one that has a sequence that is not naturally occurring and/or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. Recombinant is also used to describe nucleic acid molecules that have been artificially manipulated, but contain the same regulatory sequences and coding regions that are found in the organism from which the nucleic acid was isolated.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (e.g., human and mouse sequences), compared to species more distantly related (e.g., human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Nat. Acad Sci. USA* 85:2444, 1988; Higgins & Sharp, *Gene,* 73:23744, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (e.g., C:\seq1.txt); j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\B12seq-i c:\seq1.txt-j c:\seq2.txt-p blastn-o c:\output.txt-q-1-r2.

To compare two amino acid sequences, the options of B12seq can be set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq-i c:seq1.txt-j c:seq2.txt-p blastp-o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

```
                     1                  20
Target Sequence:     AGGTCGTGTACTGTCAGTCA
                     | || ||| |||| |||| |
Identified Sequence: ACGTGGTGAACTGCCAGTGA
```

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least 75%, 80%, 85%, 90%, 95%, or 99% sequence identity.

When aligning short peptides (fewer than around 30 amino acids), the alignment should be performed using the Blast 2 sequences function, employing the PAM30 matrix set to default parameters (open gap 9, extension gap I penalties). Proteins with even greater similarity to the reference sequence will show increasing percentage identities when assessed by this method, such as at least 60%, 70%, 75%, 80%, 85%, 90%, 95%, 98%, 99% sequence identity. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions. Stringent conditions are sequence-dependent and are different under different environmental parameters. Nucleic acid molecules that hybridize under stringent conditions to an alanine 2,3-aminomutase gene sequence typically hybridize to a probe based on either an entire alanine 2,3-aminomutase gene or selected portions of the gene, respectively, under conditions described above.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, 70%, 80%, 90%, 95%, 98%, or 99% sequence identity determined by this method.

One of skill in the art will appreciate that these sequence identity ranges are provided for guidance only; it is possible that strongly significant homologs could be obtained that fall outside the ranges provided. An alternative (and not necessarily cumulative) indication that two nucleic acid sequences are substantially identical is that the polypeptide which the first nucleic acid encodes is immunologically cross reactive with the polypeptide encoded by the second nucleic acid.

Specific binding agent: An agent that binds substantially only to a defined target, such as a peptide target. For example, an alanine 2,3-aminomutase binding agent includes anti-alanine 2,3-aminomutase antibodies and other agents (such as peptide or drugs) that bind substantially to only an alanine 2,3-aminomutase. Antibodies to an alanine 2,3-aminomutase protein (or fragments thereof) can be used to purify or identify such a protein.

Transformed: A cell into which a nucleic acid molecule has been introduced, for example by molecular biology techniques. As used herein, the term transformation encompasses all techniques by which a nucleic acid molecule might be introduced into such a cell, including, but not limited to transfection with viral vectors, conjugation, transformation with plasmid vectors, and introduction of naked DNA by electroporation, lipofection, and particle gun acceleration.

Variants, fragments or fusion proteins: The disclosed alanine 2,3 aminomutase proteins, include variants, fragments, and fusions thereof. DNA sequences which encode for a protein (for example SEQ ID NO: 20 or 29), fusion alanine 2,3 aminomutase protein, or a fragment or variant of an alanine 2,3 aminomutase protein, can be engineered to allow the protein to be expressed in eukaryotic cells, bacteria, insects, and/or plants. To obtain expression, the DNA sequence can be altered and operably linked to other regulatory sequences. The final product, which contains the regulatory sequences and the protein, is referred to as a vector. This vector can be introduced into eukaryotic, bacteria, insect, and/or plant cells. Once inside the cell the vector allows the protein to be produced.

A fusion protein including a protein, such as an alanine 2,3-aminomutase (or variant, polymorphism, mutant, or fragment thereof), for example SEQ ID NO: 21 or 30, linked to other amino acid sequences that do not inhibit the desired activity of alanine 2,3-aminomutase, for example the ability to convert alpha-alanine to beta-alanine. In one example, the other amino acid sequences are no more than about 10, 12, 15, 20, 25, 30, or 50 amino acids in length.

One of ordinary skill in the art will appreciate that a DNA sequence can be altered in numerous ways without affecting the biological activity of the encoded protein. For example, PCR can be used to produce variations in the DNA sequence which encodes an alanine 2,3-aminomutase. Such variants can be variants optimized for codon preference in a host cell used to express the protein, or other sequence changes that facilitate expression.

Vector: A nucleic acid molecule as introduced into a cell, thereby producing a transformed cell. A vector may include nucleic acid sequences that permit it to replicate in the cell, such as an origin of replication. A vector may also include one or more selectable marker genes and other genetic elements known in the art.

Alanine 2,3-Aminomutase Nucleic Acids and Polypeptides

Polypeptides having alanine 2,3-aminomutase activity are disclosed herein. In one example, the polypeptide is a mutated aminomutase amino acid sequence, such as a lysine 2,3-aminomutase, leucine 2,3-aminomutase, or lysine 5,6-aminomutase sequence. Examples of a polypeptide having alanine 2,3-aminomutase activity are shown in SEQ ID NOS: 21 and 30. However, the disclosure also encompasses variants, fusions, and fragments of SEQ ID NOS: 21 and 30 which retain alanine 2,3-aminomutase activity. Examples of fragments which can be used include, but are not limited to: amino acids 50-390,50-350, 60-350,75-340, or 100-339 of SEQ ID NO: 21 and amino acids 1-390, 15-390, 15-340 or 19-331 of SEQ ID NO:30. Examples of substitutions which can be made, while still retaining alanine 2,3-aminomutase activity, include, but are not limited to: V21I or V21L; Y71P; L17I; K361R; A410V; and/or Y430F or Y430W of SEQ ID NO: 21, and T40S; V961 or V96L; D102E; A252V; and/or L393V of SEQ ID NO: 30, as well as combinations thereof.

The disclosure provides enzyme polypeptides, such as an alanine 2,3-aminomutase (for example SEQ ID NO: 21 and/or 30, and variants, fragments, and fusions thereof that retain alanine 2,3-aminomutase activity). One skilled in the art will understand that variant enzyme sequences can be used, as long as the enzyme retains the desired enzyme activity, such as alanine 2,3-aminomutase activity. For example, the disclosure provides polypeptides that contain at least 15 contiguous amino acids which are identical to an enzyme sequence, such as an alanine 2,3-aminomutase sequence. It will be appreciated that the disclosure also provides polypeptides that contain an amino acid sequence that is greater than at least 15 amino acid residues (e.g., at least 16, 17, 18, 19, 20, 21, 22, 23, 24, 25, 26, 27, 28, 29, 30, 50, 75, 100, 150, 200, 250, 300 or more amino acid residues) and identical to any enzyme disclosed herein or otherwise publicly available.

In addition, the disclosure provides enzyme polypeptides, such as an alanine 2,3-aminomutase peptide (e.g. SEQ ID NO: 21 and/or 30), which includes an amino acid sequence having a variation of the enzyme amino acid sequence. Variant sequences can contain a single insertion, a single deletion, a single substitution, multiple insertions, multiple deletions, multiple substitutions, or any combination thereof (e.g., single deletion together with multiple insertions). Such polypeptides share at least 60, 65, 70, 75, 80, 85, 90, 95, 97, 98, or 99% sequence identity with an enzyme sequence, such as an alanine 2,3-aminomutase sequence, as long as the peptide encoded by the amino acid sequence retains the desired enzyme activity.

Polypeptides having a variant amino acid sequence can retain enzymatic activity, such as alanine 2,3-aminomutase activity. Such polypeptides can be produced by manipulating the nucleotide sequence encoding a polypeptide using standard procedures such as site-directed mutagenesis or PCR. One type of modification includes the substitution of one or more amino acid residues, such as no more than 10 amino acids, for amino acid residues having a similar biochemical property, that is, a conservative substitution.

More substantial changes can be obtained by selecting substitutions that are less conservative, e.g., selecting residues that differ more significantly in their effect on maintaining: (a) the structure of the polypeptide backbone in the area of the substitution, for example, as a sheet or helical conformation; (b) the charge or hydrophobicity of the polypeptide at the target site; or (c) the bulk of the side chain. The substitutions that in general are expected to produce the greatest changes in polypeptide function are those in which: (a) a hydrophilic residue, e.g., serine or threonine, is substituted for (or by) a hydrophobic residue, e.g., leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain, e.g., glycine. The effects of these amino acid substitutions (or other deletions or additions) can be assessed for polypeptides having enzymatic activity by analyzing the ability of the polypeptide to catalyze the conversion of the same substrate as the related native polypeptide to the same product as the related native polypeptide. Accordingly, polypeptides having no more than 5, 10, 20, 30, 40, or 50 conservative substitutions are provided herein.

Also disclosed are isolated nucleic acids that encode polypeptides having alanine 2,3-aminomutase activity, for example a sequence which includes SEQ ID NO: 20 or 29. However, the disclosure also encompasses variants, fusions, and fragments of SEQ ID NOS: 20 and 29 which retain the ability to encode a protein or peptide having alanine 2,3-aminomutase activity. In one example an isolated nucleic acid encoding a polypeptide having alanine 2,3-aminomutase activity is operably linked to a promoter sequence, and can be part of a vector. The nucleic acid can be a recombinant nucleic acid, that can be used to transform cells and make transformed cells and/or transgenic non-human mammals.

Transformed cells including at least one exogenous nucleic acid molecule which encodes a polypeptide having alanine 2,3-aminomutase activity (such as SEQ ID NO: 20 and/or 29 or fragments, fusions, or variants thereof that retain alanine 2,3-aminomutase activity), is disclosed. In one example, such a transformed cell produces beta-alanine from alpha-alanine. In another example, the cell produces 3-HP, pantothenate, CoA, and/or organic compounds such as 1,3-propanediol.

The nucleic acid sequences encoding the enzymes disclosed herein, such as alanine 2,3-aminomutase (SEQ ID NO: 20 and 29), lysine 2,3-aminomutase (SEQ ID NOS: 3 and 28), and beta-alanyl-CoA ammonia lyase (SEQ ID NO: 22), (as well as any other enzyme disclosed herein), can contain an entire nucleic acid sequence encoding the enzyme, as well as a portions thereof that retain the desired enzyme activity. For example, an enzyme nucleic acid can contain at least 15 contiguous nucleotides of an enzyme nucleic acid sequence. It will be appreciated that the disclosure also provides isolated nucleic acid that contains a nucleotide sequence that is greater than 15 nucleotides (e.g., at least 16, 17, 18, 19, 20, 21, 22, 23, 24, 25, 26, 27, 28, 29, 30, 40, 50, 75, 10, 200, 500 or more nucleotides) in length and identical to any portion of an enzyme sequence, such as an alanine 2,3-aminomutase sequence shown in SEQ ID NO: 20 and/or 29.

In addition, the disclosure provides isolated enzyme nucleic acid sequences which contains a variation of an enzyme sequence, such as a variant alanine 2,3-aminomutase nucleic acid sequence. Variants can contain a single insertion, a single deletion, a single substitution, multiple insertions, multiple deletions, multiple substitutions, or any combination thereof (e.g., single deletion together with multiple insertions) as long as the peptide encoded thereby retains alanine 2,3-aminomutase activity. Such isolated nucleic acid molecules can share at least 60, 70, 75, 80, 85, 90, 92, 95, 97, 98, or 99% sequence identity with an enzyme sequence, such as an alanine 2,3-aminomutase sequence, as long as the peptide encoded by the nucleic acid retains the desired enzyme activity, such as alanine 2,3-aminomutase activity. For example, the following variations can be made to the alanine 2,3-aminomutase nucleic acid sequence: for SEQ ID NO: 20, the "a" at position 12 can be substituted with an "g"; the "g" at position 1050 can be substituted with an "a"; the "a" at position 255; can be substituted with an "g" "t" or "c;" for SEQ ID NO: 29, the "a" at position 6 can be substituted with a "g" "t" or "c"; the "t" at position 66 can be substituted with a "c"; and the "g" at position 315; can be substituted with an "a" "t" or "c."

Codon preferences and codon usage tables for a particular species can be used to engineer isolated nucleic acid molecules that take advantage of the codon usage preferences of that particular species. For example, the enzymes disclosed herein can be designed to have codons that are preferentially used by a particular organism of interest.

The disclosure also provides isolated nucleic acid sequences that encode for an enzyme, such as alanine 2,3-aminomutase, wherein the sequence is at least about 12 bases in length (e.g., at least about 13, 14, 15, 16, 17, 18, 19, 20, 25, 30, 40, 50, 60, 100, 250, 500, 750, 1000, 1500, 2000, 3000, 4000, or 5000 bases in length) and hybridizes, under hybridization conditions, to the sense or antisense strand of a nucleic acid encoding the enzyme. The hybridization conditions can be moderately or highly stringent hybridization conditions.

Polypeptides and nucleic acid encoding polypeptide can be produced by standard DNA mutagenesis techniques, for example, M13 primer mutagenesis. Details of these techniques are provided in Sambrook et al. (ed.), Molecular Cloning: A Laboratory Manual 2nd ed., vol. 1-3, Cold Spring Harbor Laboratory Press, Cold Spring, Harbor, N.Y., 1989, Ch. 15. Nucleic acid molecules can contain changes of a coding region to fit the codon usage bias of the particular organism into which the molecule is to be introduced.

Alternatively, the coding region can be altered by taking advantage of the degeneracy of the genetic code to alter the coding sequence in such a way that, while the nucleic acid sequence is substantially altered, it nevertheless encodes a polypeptide having an amino acid sequence identical or substantially similar to the native amino acid sequence. For example, because of the degeneracy of the genetic code, alanine is encoded by the four nucleotide codon triplets: GCT, GCA, GCC, and GCG. Thus, the nucleic acid sequence of the open reading frame can be changed at an alanine position to any of these codons without affecting the amino acid sequence of the encoded polypeptide or the characteristics of the polypeptide. Based upon the degeneracy of the genetic code, nucleic acid variants can be derived from a nucleic acid sequence using a standard DNA mutagenesis techniques as described herein, or by synthesis of nucleic acid sequences. Thus, this disclosure also encompasses nucleic acid molecules that encode the same polypeptide but vary in nucleic acid sequence by virtue of the degeneracy of the genetic code.

Cells with Alanine 2,3-Aminomutase Activity

Cells having alanine 2,3-aminomutase activity are disclosed. Such cells can produce beta-alanine from alpha-alanine. In one example, such cells have alanine 2,3-aminomutase activity due to a naturally occurring mutation, and/or a mutation induced in the chromosome(s) of the cell, for example by exposing the cell to chemical or UV mutagenesis. Cells including alanine 2,3-aminomutase activity can be eukaryotic or prokaryotic. Examples of such cells include, but are not limited to *Lactobacillus, Lactococcus, Bacillus, Escherichia, Geobacillus, Corynebacterium, Clostridium*, fungal, plant, and yeast cells. In one example, a plant cell is part of a plant, such as a transgenic plant.

In one example, cells having alanine 2,3-aminomutase activity are transformed cells. Such cells can include at least one exogenous nucleic acid molecule that encodes an alanine 2,3-aminomutase, for example a sequence comprising SEQ ID NO: 20 or 29, or variants, fragments, or fusions thereof that retain the ability to encode a protein having alanine 2,3-aminomutase activity. In one example, the exogenous nucleic acid molecule is a mutated lysine 2,3-aminomutase, such as a mutated prokaryotic lysine 2,3-aminomutase. In specific examples, the mutated prokaryotic lysine 2,3-aminomutase is a mutated *Bacillus subtilis, Deinococcus radiodurans, Clostridium subterminale, Aquifex aeolicus, Haemophilus influenzae, E. coli*, or *Porphyromonas gingivalis* lysine 2,3-aminomutase. Other lysine 2,3-aminomutases can be identified by using methods known in the art, for example by searching for similar sequences on BLAST and/or by using hybridization methods. In a specific example, the mutated lysine 2,3-aminomutase is a mutated *B. subtilis* or a mutated *P. gingivalis* lysine 2,3-aminomutase. In an another example, the exogenous nucleic acid molecule is a mutated lysine 5,6-aminomutase, such as a mutated prokaryotic lysine 5,6-aminomutase. Alternatively, the exogenous nucleic acid molecule is a mutated leucine 2,3-aminomutase, or a mutated lysine 5,6-aminomutase, such as a mutated *C. sticklandii* lysine 5,6-aminomutase.

In a particular example, the mutated lysine 2,3-aminomutase is a mutated *B. subtilis* lysine 2,3-aminomutase having a substitution at position L103, D339 and/or M136. For example, the substitution can include a L103M, L103K, L103R, L103E, or L103S substitution. In another or additional example, the substitution includes a D339H, D339Q, D339T, or D339N substitution. In yet another example, the substitution can include a L103M, a M136V substitution, a D339H substitution, or any combination thereof.

Cells which include alanine 2,3-aminomutase activity as well as other enzyme activities, are disclosed. Such cells can be used to produce beta-alanine, 3-HP, pantothenate, CoA, and organic acids, polyols such as 1,3-propanediol, acrylic acid, polymerized acrylate, esters of acrylate, polymerized 3-HP, co-polymers of 3-HP and other compounds such as butyrates, valerates and other compounds, and esters of 3-HP.

In one example, such cells also include alanine dehydrogenase or pyruvate/glutamate transaminase activity, CoA transferase activity or CoA synthetase, beta-alanyl-CoA ammonia lyase activity, 3-HP-CoA dehydratase activity, glutamate dehydrogenase activity, 3-hydroxypropionyl-CoA 0.15 hydrolase, or 3-hydroxyisobutryl-CoA hydrolase activity. In another example, such cells also include alanine dehydrogenase or pyruvate-glutamate transaminase activity, 4-aminobutyrate and/or beta-alanine-2-oxoglutarate aminotransferase activity, glutamate dehydrogenase activity, and 3-HP or 3-hydroxyisobutyrate dehydrogenase activity. In these examples, the cells can be used to produce 3-HP.

In another example, the cells also include alanine dehydrogenase or pyruvate/glutamate transaminase activity, CoA transferase or CoA synthetase activity, beta-alanyl-CoA ammonia lyase activity, 3-HP-CoA dehydratase activity, glutamate dehydrogenase activity, and 3-hydroxypropionyl-CoA hydrolaseor 3-hydroxyisobutryl-CoA hydrolase activity. In another example, such cells also include alanine dehydrogenase or pyruvate-glutamate transaminase activity, 4-aminobutyrate and/or beta-alanine-2-oxoglutarate aminotransferase activity, glutamate dehydrogenase activity, and 3-HP or 3-hydroxyisobutyrate dehydrogenase activity; and lipase or esterase activity. Such cells can be used to produce an ester of 3-HP, such as methyl 3-hydroxypropionate, ethyl 3-hydroxypropionate, propyl 3-hydroxypropionate, butyl 3-hydroxypropionate, or 2-ethylhexyl 3-hydroxypropionate.

In another example, the cells also include alanine dehydrogenase or pyruvate/glutamate transaminase activity, CoA synthetase activity, beta-alanyl-CoA ammonia lyase activity, 3-HP-CoA dehydratase activity, glutamate dehydrogenase activity; and poly hydroxacid synthase activity. Such cells can be used to produce polymerized 3-HP.

In yet another example, the cells also include alanine dehydrogenase or pyruvate/glutamate transaminase activity, CoA synthetase activity, beta-alanyl-CoA ammonia lyase activity, glutamate dehydrogenase activity and poly hydroxacid synthase activity. Such cells can be used to produce polymerized acrylate.

In another example, the cells also include alanine dehydrogenase or pyruvate/glutamate transaminase activity, CoA transferase or CoA synthetase activity, beta-alanyl-CoA ammonia lyase activity, glutamate dehydrogenase activity, and lipase or esterase activity, wherein the cells can be used to produce an ester of acrylate, such as methyl acrylate, ethyl acrylate, propyl acrylate, or butyl acrylate.

Alternatively, such cells also include alanine dehydrogenase or pyruvate-glutamate transaminase activity, CoA transferase or CoA synthetase activity, beta-alanyl-CoA ammonia lyase activity, 3-HP-CoA dehydratase activity, glutamate dehydrogenase activity, 3-hydroxypropionyl-CoA hydrolase or 3-hydroxyisobutryl-CoA hydrolase activity, and aldehyde or alcohol dehydrogenase activity. Such cells can be used to produce 1,3-propanediol.

In one example, the cells also have alpha-ketopantoate hydroxymethyltransferase (E.C. 2.1.2.11), alpha-ketopantoate reductase (E.C. 1.1.1.169), and pantothenate synthase (E.C. 6.3.2.1) activity. Such cells can be used to produce pantothenate. Alternatively or in addition, the cells also have pantothenate kinase (E.C. 2.7.1.33), 4'-phosphopantethenoyl-1-cysteine synthetase (E.C. 6.3.2.5),4'-phosphopantothenoylcysteine decarboxylase (E.C. 4.1.1.36), ATP:4'-phosphopantetheine adenyltransferase (E.C. 2.7.7.3), and dephospho-CoA kinase (E.C. 2.7.1.24) activity. Such cells can be used to produce coenzyme A (CoA).

Methods to Identify Cells Having Alanine 2,3-Aminomutase Activity

A method of identifying a cell having alanine 2,3-aminomutase activity is disclosed. The method includes culturing a cell, such as a prokaryotic cell, which is functionally deleted for panD, in media which includes alpha-alanine, but not beta-alanine or pantothenate, or in media in which the cell can produce alpha-alanine from media sources of carbon, oxygen, hydrogen, and nitrogen, but which does not include beta-alanine or pantothenate, and identifying cells capable of growing in the beta-alanine or pantothenate deficient-media. In particular examples, the cell is also functionally deleted for panF. Growth of the cell indicates that the cell is producing beta-alanine from alpha-alanine, which indicates the cell has alanine 2,3-aminomutase activity. In contrast, if a cell does not grow and/or survive on the beta-alanine or pantothenate deficient-media, this indicates that the cell is not producing beta-alanine from alpha-alanine, which indicates the cell does not have alanine 2,3-aminomutase activity.

In one example, the cell functionally deleted for panD is transformed with one or more mutated aminomutases, such as libraries including mutated lysine 2,3-aminomutase, mutated leucine 2,3-aminomutase, and/or mutated lysine 5,6-aminomutase. In a particular example, the cell is transformed with a library of mutated lysine 2,3-aminomutases, prior to culturing and screening the cells. The enzyme lysine 2,3-aminomutase has been previously cloned from *Clostridium subterminale* SB4 (Chirpich et al., J. Biol. Chem. 245:1778-89, 1970) and *Bacillus subtilis* (Chen et al., *Biochem. J.* 348:539-49, 2000), and has been shown to catalyze the interconversion of lysine and beta-lysine. Mutant aminomutases, such as a mutant lysine 2,3-aminomutase, can be screened for their ability to confer alanine 2,3-aminomutase activity. In addition, although a polypeptide having alanine 2,3-aminomutase activity has not been previously described, such an enzyme may exist in nature. Thus, a cell functionally deleted for panD can be transformed with a library including a gene encoding for alanine 2,3-aminomutase, and the gene isolated by its ability to confer growth to this cell in media containing alpha-alanine, or carbon, oxygen, hydrogen, and nitrogen sources such that the cell can generate alpha-alanine, but not containing beta-alanine or pantothenate.

In another example, the method further includes identifying a mutation in the mutated aminomutase(s) following identifying a cell which grows in the media, wherein the mutated aminomutase(s) confers alanine 2,3-aminomutase activity to the cell. To identify the mutation, the aminomutase nucleic acid or amino acid can be sequenced and compared to a non-mutated aminomutase sequence, to identify mutations that confer alanine 2,3-aminomutase activity to the cell.

Methods of Producing a Peptide having Alanine 2,3-Aminomutase Activity

A method for producing alanine 2,3-aminomutase peptides having alanine 2,3-aminomutase activity, is disclosed. The method includes culturing the disclosed cells having alanine 2,3-aminomutase activity under conditions that allow the cell to produce the alanine 2,3-aminomutase peptide. In one example, the method includes culturing cells having one or more exogenous nucleic acid molecules which encode for an alanine 2,3-aminomutase (such as a sequence which includes SEQ ID NO: 20 and/or 29 or variants, fusions, or fragments thereof that retain alanine 2,3-aminomutase activity), such that the alanine 2,3-aminomutase is produced.

A method for making beta-alanine from alpha-alanine is also disclosed. In one example, the method includes culturing the disclosed cells having alanine 2,3-aminomutase activity under conditions that allow the cell to produce beta-alanine from alpha-alanine. In one example, the method includes culturing cells having one or more exogenous nucleic acid molecules which encode for an alanine 2,3-aminomutase, such that the alanine 2,3-aminomutase is capable of producing beta-alanine from alpha-alanine. In one example, the exogenous nucleic acid is a sequence that includes SEQ ID NO: 20 and/or 29 or variants, fusions, or fragments thereof that retain alanine 2,3-aminomutase activity.

In particular examples, the cell is functionally deleted for panD, or panD and panF.

Pathways for Producing 3-HP, Pantothenate and Derivatives Thereof

Methods and materials related to producing beta-alanine from alpha-alanine, via an alanine 2,3-aminomutase, such as using the disclosed alanine 2,3-aminomutase sequences and the disclosed cells having alanine 2,3-aminomutase activity are disclosed. In addition, methods and materials related to producing pantothenate and 3-HP from beta-alanine, as well as CoA and organic compounds such as 1,3-propanediol, acrylic acid, polymerized acrylate, esters of acrylate, polymerized 3-HP, co-polymers of 3-HP and other compounds such as butyrates, valerates and other compounds, and esters of 3-HP, are disclosed. Specifically, the disclosure provides alanine 2,3-aminomutase nucleic acids (such as SEQ ID NO: 20 and 29), polypeptides (such as SEQ ID NO: 21 and 30), host cells, and methods and materials for producing beta-alanine from alpha-alanine, which can be used to more efficiently make beta-alanine pantothenate and 3-HP as well as derivatives thereof such as CoA and organic compounds such as 1,3-propanediol, acrylic acid, polymerized acrylate, esters of acrylate, polymerized 3-HP, and esters of 3-BP.

Figure 3:
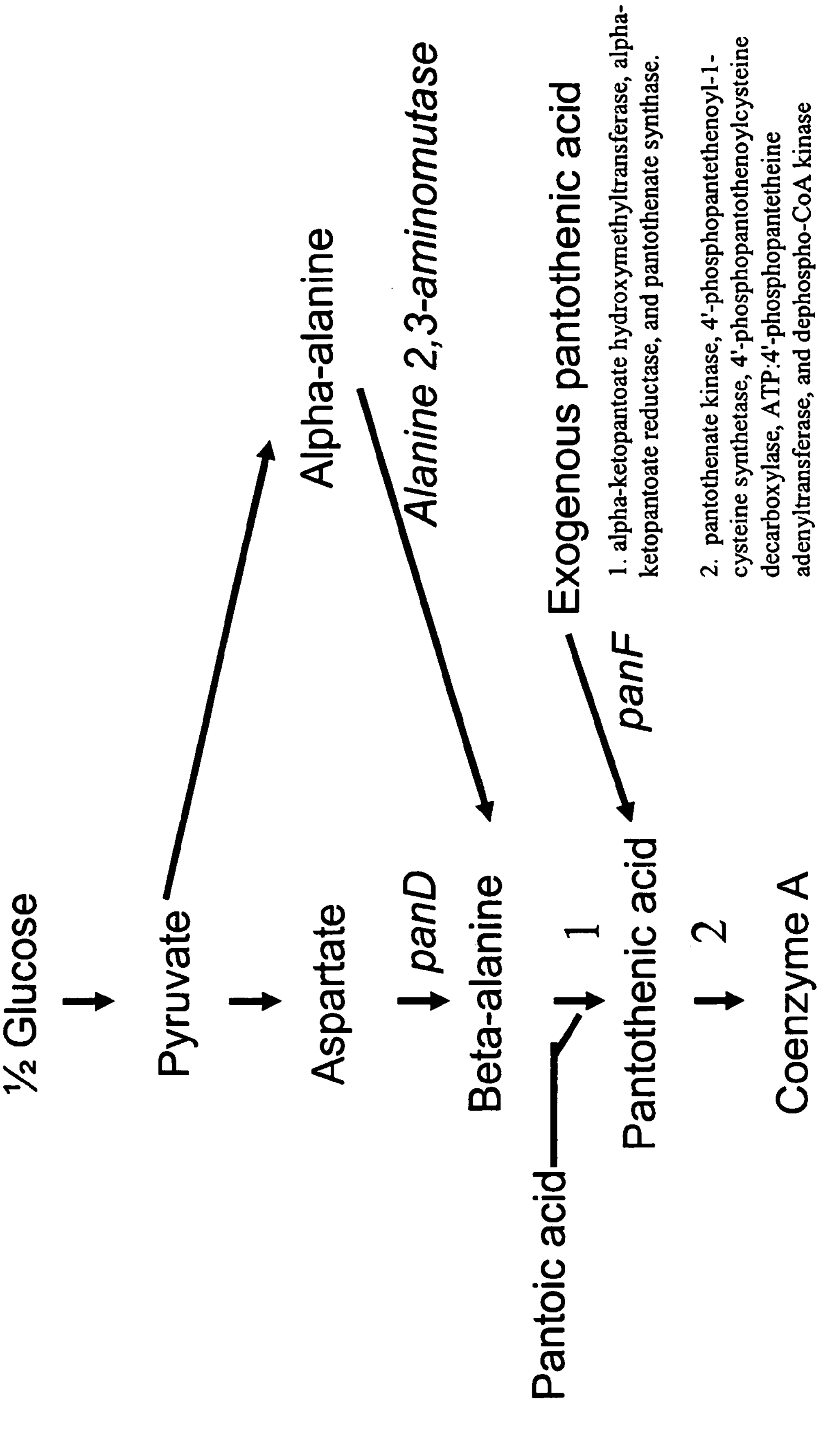
FIG. 3 is a diagram of a pathway for generating coenzyme A and pantothenate from beta-alanine.

Several metabolic pathways can be used to produce organic compounds from beta-alanine which has been produced from alpha-alanine (FIGS. 1 and 3).

Pathways of 3-HP and it Derivatives

As shown in FIG. 1, beta-alanine can be converted into beta-alanyl-CoA through the use of a polypeptide having CoA transferase activity (EC 2.8.3.1) or CoA synthase activity (E.C. 6.2.1.-). Beta-alanine can be produced from alpha-alanine by endogenous polypeptides in a host cell which converts alpha-alanine to beta-alanine, and/or by using a cell transformed with recombinant alanine 2,3-aminomutase, such as a sequence including SEQ ID NO: 20 and/or 29, or fragments, variants, or fusions thereof that retain alanine 2,3-aminomutase activity. Beta-alanyl-CoA can then be converted into acrylyl-CoA through the use of a polypeptide having beta-alanyl-CoA ammonia lyase activity (EC4.3.1.6). Acrylyl-CoA can then be converted into 3-hydroxypropionyl-CoA (3-HP-CoA) through the use of a polypeptide having 3-HP-CoA dehydratase activity (EC 4.2.1.-). 3-HP-CoA can then be converted into 3-HP through several enzymes, including, but not limited to: a polypeptide having CoA transferase activity (EC 2.8.3.1), a polypeptide having 3-hydroxypropionyl-CoA hydrolase activity (EC 3.1.2.-), and a polypeptide having 3-hydroxyisobutryl-CoA hydrolase activity (EC 3.1.2.4) can be used to convert 3-HP-CoA into 3-HP.

As shown in FIG. 1, 3-HP can be made from beta-alanine by use of a polypeptide having 4-aminobutyrate and/or beta-alanine-2-oxoglutarate aminotransferase activity which generates malonic semialdehyde from beta-alanine. The malonic semialdehyde can be converted into 3-HP with a polypeptide having 3-HP dehydrogenase activity (EC 1.1.1.59) or a polypeptide having 3-hydroxyisobutyrate dehydrogenase activity (EC 1.1.1.31).

Derivatives of 3-HP can be made from beta-alanine as shown in FIG. 1. The resulting 3-HP-CoA can be converted into polymerized 3-HP by a polypeptide having poly hydroxyacid synthase activity (EC 2.3.1.-). Alternatively or in addition, 3-HP-CoA can be converted into 1,3-propanediol by polypeptides having oxidoreductase activity or reductase activity.

The resulting acrylyl-CoA can be converted into polymerized acrylate by a polypeptide having poly hydroxyacid synthase activity (EC 2.3.1.-). Alternatively or in addition, acrylyl-CoA can be converted into acrylate by a polypeptide having CoA transferase activity and/or CoA hydrolase activity; and the resulting acrylate can be converted into an ester of acrylate by a polypeptide having lipase or esterase activity.

The resulting 3-HP can be converted into an ester of 3-HP by a polypeptide having lipase or esterase activity (EC 3.1.1.-). Alternatively or in addition, 1,3-propanediol can be created from 3-HP, by a combination of a polypeptide having aldehyde dehydrogenase activity and a polypeptide having alcohol dehydrogenase activity.

Pathways of Pantothenate and it Derivatives

As shown in FIG. 3, pantothenate can be made from beta-alanine by a peptide having alpha-ketopantoate hydroxymethyltransferase (E.C. 2.1.2.11), alpha-ketopantoate reductase (E.C. 1.1.1.169), and pantothenate synthase (E.C. 6.3.2.1) activities, which converts beta-alanine to pantothenate.

Derivatives of pantothenate can be made from beta-alanine as follows. The resulting pantothenate can be converted into CoA by polypeptides having pantothenate kinase (E.C. 2.7.1.33), 4'-phosphopantethenoyl-1-cysteine synthetase (E.C. 6.3.2.5), 4'-phosphopantothenoylcysteine decarboxylase (E.C. 4.1.1.36), ATP:4'-phosphopantetheine adenyltransferase (E.C. 2.7.7.3), and dephospho-CoA kinase (E.C. 2.7.1.24) activities.

Enzymes

Polypeptides having lysine 2,3-aminomutase activity as well as nucleic acid encoding such polypeptides can be obtained from various species including, but not limited to: *Clostridium subterminale, E. coli, B. subtilis, Deinococcus radiodurans, Porphyromonas gingivalis, Aquifex aeolicus*, or *Haemophilus influenza*. For example, amino acid sequences having lysine 2,3-aminomutase activity are shown in SEQ ID NO: 31 for *B. subtilis* and iii SEQ ID NO: 28 for *P. gingivalis.*

In another example, a nucleic acid that encodes a polypeptide having alanine 2,3-aminomutase activity is shown in SEQ ID NO: 20 for *B. subtilis* (the corresponding amino acid sequence is shown in SEQ ID NO: 21), and in SEQ ID NO: 29 for *P. gingivalis* (the corresponding amino acid sequence is shown in SEQ ID NO: 30). In addition, other polypeptides having alanine 2,3-aminomutase activity as well as nucleic acids encoding such polypeptides, can be obtained using the methods described herein. For example, alanine 2,3-aminomutase variants can be used to encode a polypeptide having alanine 2,3-aminomutase activity as described above.

Polypeptides having CoA transferase activity as well as nucleic acid encoding such polypeptides can be obtained from various species including, but not limited to, *Megasphaera elsdenii, Clostridium propionicum, Clostridium kluyveri*, and *E. coli*. For example, nucleic acid that encodes a polypeptide having CoA transferase activity is shown in SEQ ID NO: 24 for *M. eisdenii*. In addition, polypeptides having CoA transferase activity (SEQ ID NO: 25) as well as nucleic acid encoding such polypeptides (SEQ ID NO: 24) can be obtained as described herein. For example, CoA transferase variants can be used to encode a polypeptide having CoA transferase activity. For example, the following variations can be made to the CoA transferase nucleic acid sequence (SEQ ID NO: 24): the "a" at position 49 can be substituted with an "c"; the "a" at position 590 can be substituted with a "atgg"; an "aaac" can be inserted before the "g" at position 393; or the "gaa" at position 736 can be deleted. It will be appreciated that the sequences set forth in the sequence listing can contain any number of variations as well as any combination of types of variations, as long as the peptide retains CoA transferase activity. In addition, the following variations can be made to the CoA transferase amino acid sequence shown in SEQ ID NO: 25: the "k" at position 17 of can be substituted with a "p" or "h"; and the "v" at position 125 can be substituted with an "i" or "f."

Polypeptides having beta-alanyl-CoA ammonia lyase activity as well as nucleic acid encoding such polypeptides can be obtained from various species including, without limitation, *C. propionicum*. For example, nucleic acid encoding a polypeptide complex having beta-alanyl-CoA ammonia lyase activity can be obtained from *C. propionicum* as described in EXAMPLE 10. The nucleic acid encoding a beta-alanyl-CoA ammonia lyase can contain a sequence as set forth in SEQ ID NO: 22. In addition, polypeptides having beta-alanyl-CoA ammonia lyase activity (SEQ ID NO: 23) as well as nucleic acid encoding such polypeptides (SEQ ID NO: 22) can be obtained as described herein. For example, the variations to the beta-alanyl-CoA ammonia lyase sequence shown in SEQ ID NO: 22 can be used to encode a polypeptide having beta-alanyl-CoA ammonia lyase activity.

Polypeptides having 3-hydroxypropionyl-CoA dehydratase activity (also referred to as acrylyl-CoA hydratase activity) as well as nucleic acid encoding such polypeptides can be obtained from various species including, but not limited to, *Chloroflexus aurantiacus, Candida rugosa, Rhodosprillium rubrum*, and *Rhodobacter capsulates*. For example, a nucleic acid that encodes a polypeptide having 3-hydroxypropionyl-CoA dehydratase activity is disclosed in WO 02/42418.

Polypeptides having glutamate dehydrogenase activity as well as nucleic acid encoding such polypeptides can be obtained from various species.

Polypeptides having 3-hydroxypropionyl-CoA or 3-hydroxyisobutryl-CoA hydrolase activity, as well as nucleic acid encoding such polypeptides, can be obtained from various species including, without limitation, *Pseudomonas fluorescens, Rattus rattus*, and *Homo sapiens*. For example, nucleic acid that encodes a polypeptide having 3-hydroxyisobutyryl-CoA hydrolase activity can be obtained from *H. sapiens* and can have a sequence as set forth in GenBank accession number U66669.

Polypeptides having 4-aminobutyrate and/or beta-alanine-2-oxoglutarate aminotransferase activity, 3-HP dehydrogenase activity, and 3-hydroxyisobutyrate dehydrogenase activity, as well as nucleic acid encoding such polypeptides can be obtained from various species.

Polypeptides having poly hydroxyacid synthase activity as well as nucleic acid encoding such polypeptides can be obtained from various species including, without limitation, *Rhodobacter sphaeroides, Comamonas acidororans, Raistonia eutropha*, and *Pseudomonas oleovorans*. For example, nucleic acid that encodes a polypeptide having poly hydroxyacid synthase activity can be obtained from *R. sphaeroides* and can have a sequence as set forth in GenBank accession number X97200. Addition information about poly hydroxyacid synthase can be found in Song et al. (*Biomacromolecules* 1:433-9,2000).

Polypeptides having acetylating aldehyde:NAD(+) oxidoreductase activity (EC 1.2.1.10) as well as nucleic acid encoding such polypeptides can be obtained from various species including, without limitation, *E. coli*. For example, nucleic acid that encodes a polypeptide having acylating aldehyde dehydrogenase activity can be obtained from *E. coli* and can have a sequence as set forth in GenBank accession number Y09555.

Aldehyde:NAD(+) oxidoreductase activity and alcohol: NAD(+) oxidoreductase activities can be carried out by two different polypeptides as described above, or carried out by a single polypeptide, such as a multi-functional aldehyde-alcohol dehydrogenase (EC 1.2.1.10) from *E. coli* (Goodlove et al. Gene 85:209-14, 1989; GenBank Accession No. M33504).

Polypeptides having aldehyde dehydrogenase (NAD(P)+) (EC 1.2.1.-) activity as well as nucleic acid encoding such polypeptides can be obtained from various species including, without limitation, *S. cerevisiae*. For example, nucleic acid that encodes a polypeptide having aldehyde dehydrogenase activity can be obtained from *S. cerevisiae* and can have a sequence as set forth in GenBank Accession No. Z75282 (Tessier et al. *FEMS Microbiol. Lett.* 164:29-34, 1998).

Polypeptides having alcohol dehydrogenase activity (EC 1.1.1.1) as well as nucleic acid encoding such polypeptides can be obtained from various species including, without limitation, Z mobilis. For example, nucleic acid that encodes a polypeptide having alcohol dehydrogenase activity can be obtained from *Z. mobilis* and can have a sequence as set forth in GenBank accession No. M32100.

Polypeptides having lipase activity as well as nucleic acid encoding such polypeptides can be obtained from various species including, without limitation, *Candida rugosa, Candida tropicalis*, and *Candida albicans*. For example, nucleic acid that encodes a polypeptide having lipase activity can be obtained from *C. rugosa* and can have a sequence as set forth in GenBank accession number A81171.

Polypeptides having alpha-ketopantoate hydroxymethyltransferase and pantothenate synthase activity as well as nucleic acid encoding such polypeptides can be obtained from various species including, without limitation, *E. coli*. For example, nucleic acids that encodes polypeptides having alpha-ketopantoate hydroxymethyltransferase and pantothenate synthase activity can be obtained from *E. coli* and can have a sequence as set forth in GenBank accession number L17086.

Polypeptides having alpha-ketopantoate reductase, pantothenate kinase, 4'-phosphopantethenoyl-1-cysteine synthetase, 4'-phosphopantothenoylcysteine decarboxylase, ATP:4'-phosphopantetheine adenyltransferase, and dephospho-CoA kinase activity as well as nucleic acid encoding such polypeptides can be obtained from various species including, without limitation, *E. coli*. For example, nucleic acids that encodes polypeptides having alpha-ketopantoate reductase pantothenate kinase, 4'-phosphopantethenoyl-1-cysteine synthetase, 4'-phosphopantothenoylcysteine decarboxylase, ATP:4'-phosphopantetheine adenyltransferase, and dephospho-CoA kinase activity can be obtained from *E. coli* and can have a sequence as set forth in GenBank accession number NC000913.

The term "polypeptide having enzymatic activity" refers to any polypeptide that catalyzes a chemical reaction of other substances without itself being destroyed or altered upon completion of the reaction. Typically, a polypeptide having enzymatic activity catalyzes the formation of one or more products from one or more substrates. Such polypeptides can have any type of enzymatic activity including, without limitation, the enzymatic activity or enzymatic activities associated with enzymes such as alanine 2,3-aminomutase, dehydratases/hydratases, 3-hydroxypropionyl-CoA dehydratases/hydratases, alanine dehydrogenase, CoA transferases, 3-hydroxypropionyl-CoA hydrolases, 3-hydroxyisobutryl-CoA hydrolases, CoA hydrolases, poly hydroxyacid synthases, beta-alanine ammonia lyases, 4-aminobutyrate or beta-alanine-2-oxoglutarate aminotransferases, 3-HP dehydrogenases, 3-hydroxyisobutyrate dehydrogenases, glutamate dehydrogenases, lipases, esterases, acetylating aldehyde:NAD(+) oxidoreductases, alcohol: NAD(+) oxidoreductases, aldehyde dehydrogenases, alcohol dehydrogenases hydroxymethyltransferases, reductases, synthases, kinases, synthetases, decarboxylases, alpha-ketopantoate hydroxymethyltransferases, alpha-ketopantoate reductases, pantothenate synthases, pantothenate kinases, 4'-phosphopantethenoyl-1-cysteine synthetase, 4'-phosphopantothenoylcysteine decarboxylases, ATP:4'-phosphopantetheine adenyltransferases, dephospho-CoA kinases, acetylating aldehyde:NAD(+) oxidoreductases, alcohol:NAD(+) oxidoreductases, aldehyde dehydrogenases (NAD(P)+), alcohol dehydiogenases and adenyltransferases.

Methods of Making 3-HP, Pantothenate, and Derivatives Thereof

Each step provided in the pathways depicted in FIGS. 1 and 3 can be performed within a cell (in vivo) or outside a cell (in vitro, e.g., in a container or column). Additionally, the organic compound products can be generated through a combination of in vivo synthesis and in vitro synthesis. Moreover, the in vitro synthesis step, or steps, can be via chemical reaction or enzymatic reaction.

For example, a cell or microorganism provided herein can be used to perform the steps provided in FIGS. 1 and 3, or an extract containing polypeptides having the indicated enzymatic activities can be used to perform the steps provided in FIGS. 1 and 3. In addition, chemical treatments can be used to perform the conversions provided in FIGS. 1 and 3. For example, acrylyl-CoA can be converted into acrylate by hydrolysis. Other chemical treatments include, without limitation, trans esterification to convert acrylate into an acrylate ester.

Expression of Polypeptides

The polypeptides described herein, such as the enzymes listed in FIG. 1, can be produced individually in a host cell or in combination in a host cell. Moreover, the polypeptides having a particular enzymatic activity can be a polypeptide that is either naturally-occurring or non-naturally-occurring. A naturally-occurring polypeptide is any polypeptide having an amino acid sequence as found in nature, including wild-type and polymorphic polypeptides. Naturally-occurring polypeptides can be obtained from any species including, but not limited to, animal (e.g., mammalian), plant, fungal, and bacterial species. A non-naturally-occurring polypeptide is any polypeptide having an amino acid sequence that is not found in nature. Thus, a non-naturally-occuring polypeptide can be a mutated version of a naturally-occurring polypeptide, or an engineered polypeptide. For example, a non-naturally-occurring polypeptide having alanine 2,3-aminomutase activity can be a mutated version of a naturally-occurring polypeptide having lysine 2,3-aminomutase activity that has at least some alanine 2,3-aminomutase activity (such as SEQ ID NO: 21 and/or 30). A polypeptide can be mutated by, for example, sequence additions, deletions, substitutions, or combinations thereof.

Genetically modified cells are disclosed which can be used to perform one or more steps of the steps in the pathways described herein or the genetically modified cells can be used to produce the disclosed polypeptides for subsequent use in vitro. For example, an individual microorganism can contain exogenous nucleic acid(s) encoding each of the polypeptides necessary to perform the steps depicted in FIGS. 1 and 3. Such cells can contain any number of exogenous nucleic acid molecules. For example, a particular cell can contain one, two, three, or four different exogenous nucleic acid molecules with each one encoding the polypeptide(s) necessary to convert pyruvate into 3-HP as shown in FIG. 1, or a particular cell can endogenously produce polypeptides necessary to convert pyruvate into acrylyl-CoA while containing exogenous nucleic acid that encodes polypeptides necessary to convert acrylyl-CoA into 3-HP.

In addition, a single exogenous nucleic acid molecule can encode one, or more than one, polypeptide. For example, a single exogenous nucleic acid molecule can contain sequences that encode two, three, or even four different polypeptides. Further, the cells described herein can contain a single copy, or multiple copies (e.g., about 5, 10, 20, 35, 50, 75, 100 or 150 copies), of a particular exogenous nucleic acid molecule, such as a particular enzyme. The cells described herein can contain more than one particular exogenous nucleic acid. For example, a particular cell can contain about 50 copies of exogenous nucleic acid molecule X as well as about 75 copies of exogenous nucleic acid molecule Y.

In another example, a cell can contain an exogenous nucleic acid molecule that encodes a polypeptide having alanine 2,3-aminomutase activity, for example SEQ ID NO: 20 and/or 29 (or variants, fragments, or fusions thereof that retain alanine 2,3-aminomutase activity). Such cells can have any detectable level of alanine 2,3-aminomutase activity, including activity detected by the production of metabolites of beta-alanine, such as pantothenate. For example, a cell containing an exogenous nucleic acid molecule that encodes a polypeptide having alanine 2,3-aminomutase activity can have alanine 2,3-aminomutase activity with a specific activity greater than about 1 μg beta-alanine formed per gram dry cell weight per hour (e.g., greater than about. 10, 20, 30, 40, 50, 60, 70, 80, 90, 100, 125, 150, 200, 250, 300, 350, 400, 500, or more μg beta-alanine formed per gram dry cell weight per hour). Alternatively, a cell can have alanine 2,3-aminomutase activity such that a cell extract from $1\times10^6$ cells has a specific activity greater than about 1 ng beta-alanine formed per mg total protein per minute (e.g., greater than about 10, 20, 30, 40, 50, 60, 70, 80, 90, 100, 125, 150, 200, 250, 300, 350, 400, 500, or more ng beta-alanine formed per mg total protein per minute).

A nucleic acid molecule encoding a polypeptide having enzymatic activity can be identified and obtained using any method such as those described herein. For example, nucleic acid molecules that encode a polypeptide having enzymatic activity can be identified and obtained using common molecular cloning or chemical nucleic acid synthesis procedures and techniques, including PCR. In addition, standard nucleic acid sequencing techniques and software programs that translate nucleic acid sequences into amino acid sequences based on the genetic code can be used to determine whether or not a particular nucleic acid has any sequence homology with known enzymatic polypeptides. Sequence alignment software such as MEGALIGN (DNASTAR, Madison, Wis., 1997) can be used to compare various sequences.

In addition, nucleic acid molecules encoding known enzymatic polypeptides can be mutated using common molecular cloning techniques (e.g., site-directed mutagenesis). Possible mutations include, without limitation, deletions, insertions, and base substitutions, as well as combinations of deletions, insertions, and base substitutions. Further, nucleic acid and amino acid databases (e.g., GenBank) can be used to identify a nucleic acid sequence that encodes a polypeptide having enzymatic activity. Briefly, any amino acid sequence having some homology to a polypeptide having enzymatic activity, or any nucleic acid sequence having some homology to a sequence encoding a polypeptide having enzymatic activity can be used as a query to search GenBank. The identified polypeptides then can be analyzed to determine whether or not they exhibit enzymatic activity.

In addition, nucleic acid hybridization techniques can be used to identify and obtain a nucleic acid molecule that encodes a polypeptide having enzymatic activity. Briefly, any nucleic acid molecule that encodes a known enzymatic polypeptide, or fragment thereof, can be used as a probe to identify a similar nucleic acid molecules by hybridization under conditions of moderate to high stringency. Such similar nucleic acid molecules then can be isolated, sequenced, and analyzed to determine whether the encoded polypeptide has enzymatic activity.

Expression cloning techniques also can be used to identify and obtain a nucleic acid molecule that encodes a polypeptide having enzymatic activity. For example, a substrate known to interact with a particular enzymatic polypeptide can be used to screen a phage display library containing that enzymatic polypeptide. Phage display libraries can be generated as described (Burritt et al., *Anal. Biochem.* 238:1-13, 1990), or can be obtained from commercial suppliers such as Novagen (Madison, Wis.).

Further, polypeptide sequencing techniques can be used to identify and obtain a nucleic acid molecule that encodes a polypeptide having enzymatic activity. For example, a purified polypeptide can be separated by gel electrophoresis, and its amino acid sequence determined by, for example, amino acid microsequencing techniques. Once determined, the amino acid sequence can be used to design degenerate oligonucleotide primers. Degenerate oligonucleotide primers can be used to obtain the nucleic acid encoding the polypeptide by PCR. Once obtained, the nucleic acid can be sequenced, cloned into an appropriate expression vector, and introduced into a microorganism.

Any method can be used to introduce an exogenous nucleic acid molecule into a cell. For example, heat shock, lipofection, electroporation, conjugation, fusion of protoplasts, and biolistic delivery are common methods for introducing nucleic acid into bacteria and yeast cells. (See, e.g., Ito et al., *J. Bacterol.* 153:163-8, 1983; Durrens et al., *Curr. Genet.* 18:7-12, 1990; Sambrook et al., Molecular cloning: A laboratory manual, Cold Spring Harbour Laboratory Press, New York, USA, second edition, 1989; and Becker and Guarente, *Methods in Enzymology* 194:182-7, 1991). Other methods for expressing an amino acid sequence from an exogenous nucleic acid molecule include, but are not limited to, constructing a nucleic acid such that a regulatory element promotes the expression of a nucleic acid sequence that encodes a polypeptide. Typically, regulatory elements are DNA sequences that regulate the expression of other DNA sequences at the level of transcription. Thus, regulatory elements include, without limitation, promoters, enhancers, and the like. Any type of promoter can be used to express an amino acid sequence from an exogenous nucleic acid molecule. Examples of promoters include, without limitation, constitutive promoters, tissue-specific promoters, and promoters responsive or unresponsive to a particular stimulus (e.g., light, oxygen, chemical concentration). Methods for transferring nucleic acids into mammalian cells are also known, such as using viral vectors.

An exogenous nucleic acid molecule contained within a particular cell of the disclosure can be maintained within that cell in any form. For example, exogenous nucleic acid molecules can be integrated into the genome of the cell or maintained in an episomal state. That is, a cell can be a stable or transient transformant. A microorganism can contain single or multiple copies (e.g., about 5, 10, 20, 35, 50, 75, 100 or 150 copies), of a particular exogenous nucleic acid molecule, such as a nucleic acid encoding an enzyme.

Production of Organic Acids and Related Products Via Host Cells

The nucleic acid and amino acid sequences provided herein can be used with cells to produce beta-alanine, pantothenate and 3-HP, as well as derivatives thereof such as CoA, and organic compounds such as 1,3-propanediol, acrylic acid, polymerized acrylate, esters of acrylate, esters of 3-HP, and polymerized 3-HP. Such cells can be from any species, such as those listed within the taxonomy web pages at the National Institutes of Health. The cells can be eukaryotic or prokaryotic. For example, genetically modified cells can be mammalian cells (e.g., human, murine, and bovine cells), plant cells (e.g., corn, wheat, rice, and soybean cells), fungal cells (e.g., *Aspergillus* and *Rhizopus* cells), yeast cells, or bacterial cells (e.g., *Lactobacillus, Lactococcus, Bacillus, Escherichia*, and *Clostridium* cells). In one example, a cell is a microorganism. The term "microorganism" refers to any microscopic organism including, but not limited to, bacteria, algae, fungi, and protozoa. Thus, *E. coli, B. subtilis, B. licheniformis, S. cerevisiae, Kluveromyces lactis, Candida blankii, Candida rugosa*, and *Pichia pastoris* are microorganisms and can be used as described herein. In another example, the cell is part of a larger organisim, such as a plant, such as a transgenic plant. Examples of plants that can be used to make 3-HP, pantothenate, or other organic compounds from beta-alanine include, but are not limited to, genetically engineered plant crops such as corn, rice, wheat, and soybean.

In one example, a cell is genetically modified such that a particular organic compound is produced. In one embodiment, cells make 3-HP and/or pantothenate from beta-alanine, such as the pathways shown in FIGS. 1 and 3. In another embodiment, the cells make derivatives of 3-HP and/or pantothenate, such as CoA, and organic compounds such as 1,3-propanediol, acrylic acid, polymerized acrylate, esters of acrylate, esters of 3-HP, and polymerized 3-HP.

In one example, cells that are genetically modified to synthesize a particular organic compound contain one or more exogenous nucleic acid molecules that encode polypeptides having specific enzymatic activities. For example, a microorganism can contain exogenous nucleic acid that encodes a polypeptide having 3-hydroxypropionyl-CoA dehydratase activity. In this case, acrylyl-CoA can be converted into 3-hydroxypropionic acid-CoA which can lead to the production of 3-HP. A cell can be given an exogenous nucleic acid molecule that encodes a polypeptide having an enzymatic activity that catalyzes the production of a compound not normally produced by that cell. Alternatively, a cell can be given an exogenous nucleic acid molecule that encodes a polypeptide having an enzymatic activity that catalyzes the production of a compound that is normally produced by that cell. In this case, the genetically modified cell can produce more of the compound, or can produce the compound more efficiently, than a similar cell not having the genetic modification.

In another example, a cell containing an exogenous nucleic acid molecule that encodes a polypeptide having enzymatic activity that leads to the formation of 3-HP, pantothenate, and/or derivatives thereof, is disclosed. The produced product(s) can be secreted from the cell, eliminating the need to disrupt cell membranes to retrieve the organic compound. In one example, the cell produces 3-HP, pantothenate, and/or derivatives thereof, with the concentration of the product(s) being at least about 100 mg per L (e.g., at least about 1 g/L, 5 g/L, 10 g/L, 25 g/L, 50 g/L, 75 g/L, 80 g/L, 90 g/L, 100 g/L, or 120 g/L). When determining the yield of a compound such as 3-HP, pantothenate, and/or derivatives thereof for a particular cell, any method can be used. See, e.g., Applied Environmental Microbiology 59(12):4261-5 (1993). A cell within the scope of the disclosure can utilize a variety of carbon sources.

A cell can contain one or more exogenous nucleic acid molecules that encodes a polypeptide(s) having enzymatic activity that leads to the formation of 3-HP, pantothenate, and/or derivatives thereof, such as CoA, 1,3-propanediol, acrylic acid, poly-acrylate, acrylate-esters, 3-HP-esters, and polymers and copolymers containing 3-HP. Methods of identifying cells that contain exogenous nucleic acid(s) are well known. Such methods include, without limitation, PCR and nucleic acid hybridization techniques such as Northern and Southern analysis (see hybridization described herein). In some cases, immunohisto-chemical and biochemical techniques can be used to determine if a cell contains particular nucleic acid(s) by detecting the expression of the polypeptide(s) encoded by that particular nucleic acid molecule(s). For example, an antibody having specificity for a polypeptide can be used to determine whether or not a particular cell contains nucleic acid encoding that polypeptide. Further, biochemical techniques can be used to determine if a cell contains a particular nucleic acid molecule encoding a polypeptide having enzymatic activity by detecting an organic product produced as a result of the expression of the polypeptide having enzymatic activity. For example, detection of 3-HP after introduction of exogenous nucleic acid that encodes a polypeptide having 3-hydroxypropionyl-CoA dehydratase activity into a cell that does not normally express such a polypeptide can indicate that the cell not only contains the introduced exogenous nucleic acid molecule but also expresses the encoded polypeptide from that introduced exogenous nucleic acid molecule. Methods for detecting specific enzymatic activities or the presence of particular organic products are well known, for example, the presence of an organic compound such as 3-HP can be determined as described in Sullivan and Clarke (*J. Assoc. Offic. Agr. Chemists,* 38:514-8, 1955).

Cells with Reduced Polypeptide Activity

Genetically modified cells having reduced polypeptide activity are disclosed. The term "reduced" or "decreased" as used herein with respect to a cell and a particular polypeptide's activity refers to a lower level of activity than that measured in a comparable cell of the same species. For example, a particular microorganism lacking enzymatic activity X has reduced enzymatic activity X if a comparable microorganism has at least some enzymatic activity X.

A cell can have the activity of any type of polypeptide reduced including, without limitation, enzymes, transcription factors, transporters, receptors, signal molecules, and the like. For example, a cell can contain an exogenous nucleic acid molecule that disrupts a regulatory and/or coding sequence of a polypeptide having panD activity. Disrupting panD can prevent a cell from making beta-alanine.

Reduced polypeptide activities can be the result of lower polypeptide concentration, lower specific activity of a polypeptide, or combinations thereof. Many different methods can be used to make a cell having reduced polypeptide activity. For example, a cell can be engineered to have a disrupted regulatory sequence or polypeptide-encoding sequence using common mutagenesis or knock-out technology. (Methods in Yeast Genetics (1997 edition), Adams, Gottschling, Kaiser, and Stems, Cold Spring Harbor Press, 1998; Datsenko and Wanner, Proc. Natl. Acad. Sci. USA 97: 6640-5, 2000). Alternatively, antisense technology can be used to reduce the activity of a particular polypeptide. For example, a cell can be engineered to contain a cDNA that encodes an antisense molecule that prevents a polypeptide from being translated. The term "antisense molecule" encompasses any nucleic acid molecule or nucleic acid analog (e.g., peptide nucleic acids) that contains a sequence that corresponds to the coding strand of an endogenous polypeptide. An antisense molecule also can have flanking sequences (e.g., regulatory sequences). Thus, antisense molecules can be ribozymes or antisense oligonucleotides. A ribozyme can have any general structure including, without limitation, hairpin, hammerhead, or axhead structures, provided the molecule cleaves RNA. Further, gene silencing can be used to reduce the activity of a particular polypeptide.

A cell having reduced activity of a polypeptide can be identified using any method. For example, enzyme activity assays such as those described herein can be used to identify cells having a reduced enzyme activity.

Production of Organic Acids and Related Products Via In Vitro Techniques

Purified polypeptides having enzymatic activity can be used alone or in combination with cells to produce pantothenate, 3-HP, and/or derivatives thereof such as CoA, and organic compounds such as 1,3-propanediol, acrylic acid, polymerized acrylate, esters of acrylate, esters of 3-HP, and polymerized 3-HP. For example, a preparation including a substantially pure polypeptide having 3-hydroxypropionyl-CoA dehydratase activity can be used to catalyze the formation of 3-HP-CoA, a precursor to 3-HP.

Further, cell-free extracts containing a polypeptide having enzymatic activity can be used alone or in combination with purified polypeptides and/or cells to produce pantothenate, 3-HP, and/or deviates thereof. For example, a cell-free extract which includes a polypeptide having CoA transferase activity can be used to form beta-alanyl-CoA from beta-alanine, while a microorganism containing polypeptides which have the enzymatic activities necessary to catalyze the reactions needed to form 3-HP from beta-alanyl-CoA can be used to produce 3-HP. In another example, a cell-free extract which includes alpha-ketopantoate hydroxymethyltransferase (E.C. 2.1.2.11), alpha-ketopantoate reductase (E.C. 1.1.1.169), and pantothenate synthase (E.C. 6.3.2.1) can be used to form pantothenate from beta-alanine. Any method can be used to produce a cell-free extract. For example, osmotic shock, sonication, and/or a repeated freeze-thaw cycle followed by filtration and/or centrifugation can be used to produce a cell-free extract from intact cells. A cell, purified polypeptide, and/or cell-free extract can be used to produce 3-HP that is, in turn, treated chemically to produce another compound. For example, a microorganism can be used to produce 3-HP, while a chemical process is used to modify 3-HP into a derivative such as polymerized 3-HP or an ester of 3-HP. Likewise, a chemical process can be used to produce a particular compound that is, in turn, converted into 3-HP or other organic compound (e.g., 1,3-propanediol, acrylic acid, polymerized acrylate, esters of acrylate, esters of 3-HP, and polymerized 3-HP) using a cell, substantially pure polypeptide, and/or cell-free extract described herein. For example, a chemical process can be used to produce acrylyl-CoA, while a microorganism can be used convert acrylyl-CoA into 3-HP.

Similarly, a cell, purified polypeptide, and/or cell-free extract can be used to produce pantothenate that is, in turn, treated chemically to produce another compound. For example, a microorganism can be used to produce pantothenate, while a chemical process is used to modify pantothenate into a derivative such as CoA. Likewise, a chemical process can be used to produce a particular compound that is, in turn, converted into pantothenate or other compound (e.g., CoA) using a cell, substantially pure polypeptide, and/or cell-free extract described herein. For example, a chemical process can be used to produce pantothenate, while a microorganism can be used convert pantothenic acid into CoA.

Fermentation of Cells to Produce Organic Acids

A method for producing pantothenate, 3-HP, and/or derivatives thereof by culturing a production cells, such as a microorganism, in culture medium such that pantothenate, 3-HP, and/or derivatives thereof, is produced, is disclosed. In general, the culture media and/or culture conditions can be such that the microorganisms grow to an adequate density and produce the product efficiently. For large-scale production processes, any method can be used such as those described elsewhere (Manual of Industrial Microbiology and Biotechnology, $2^{nd}$ Edition, Editors: Demain and Davies, ASM Press; and Principles of Fermentation Technology, Stanbury and Whitaker, Pergamon).

Briefly, a large tank (e.g., a 100 gallon, 200 gallon, 500 gallon, or more tank) containing appropriate culture medium with, for example, a glucose carbon source is inoculated with a particular microorganism. After inoculation, the microorganisms are incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank. For example, the first tank can contain medium with xylose, while the second tank contains medium with glucose.

Once transferred, the microorganisms can be incubated to allow for the production of pantothenate, 3-HP, and/or derivatives thereof. Once produced, any method can be used to isolate the formed product. For example, common separation techniques can be used to remove the biomass from the broth, and common isolation procedures (e.g., extraction, distillation, and ion-exchange procedures) can be used to obtain the pantothenate, 3-HP, and/or derivatives thereof from the microorganism-free broth. Alternatively, the product can be isolated while it is being produced, or it can be isolated from the broth after the product production phase has been terminated.

Products Created From the Disclosed Biosynthetic Routes

The compounds produced from any of the steps provided in FIGS. 1 and 3 can be chemically converted into other organic compounds. For example, 3-HP can be hydrogenated to form 1,3-propanediol, a valuable polyester monomer. Hydrogenating an organic acid such as 3-HP can be performed using any method such as those used to hydrogenate succinic acid and/or lactic acid. For example, 3-HP can be hydrogenated using a metal catalyst. In another example, 3-HP can be dehydrated to form acrylic acid. Any method can be used to perform a dehydration reaction. For example, 3-HP can be heated in the presence of a catalyst (e.g., a metal or mineral acid catalyst) to form acrylic acid. 1,3-propanediol also can be created using polypeptides having oxidoreductase activity (e.g., enzymes in the 1.1.1.- class of enzymes) in vitro or in vivo.

In another example, pantothenate can be used to form coenzyme A. Polypeptides having pantothenate kinase (E.C. 2.7.1.33), 4'-phosphopantethenoyl-1-cysteine synthetase (E.C. 6.3.2.5), 4'-phosphopantothenoylcysteine decarboxylase (E.C. 4.1.1.36), ATP:4'-phosphopantetheine adenyltransferase (E.C. 2.7.7.3), and dephospho-CoA kinase (E.C. 2.7.1.24) activities can be used to produce coenzyme A.

Production of 1,3-propanediol

Methods of producing 1,3-propanediol, and cells for such production, are disclosed. 1,3-propanediol can be generated from either 3-HP-CoA or 3-HP. Cells or microorganisms producing 3-HP-CoA or 3-HP can be engineered to make 1,3-propanediol by cloning genes which encode for enzymes having oxidoreductase/dehydrogenase type activity.

For example, 3-HP-CoA can be converted to 1,3-propanediol in the presence of an enzyme having acetylating aldehyde:NAD(+) oxidoreductase and alcohol:NAD(+) oxidoreductase activities. Such conversion can be performed in vivo, in vitro, or a combination thereof. These activities can be carried out by a single polypeptide or by two different polypeptides. Single enzymes include the multi-functional aldehyde-alcohol dehydrogenase (EC 1.2.1.10) from *E. coli* (Goodlove et al. Gene 85:209-14, 1989; GenBank Accession No. M33504). Enzymes having a singular activity of acetylating aldehyde:NAD(+) oxidoreductase (EC 1.2.1.10) or alcohol:NAD(+) oxidoreductase (EC 1.1.1.1) have been described. Genes encoding for acylating aldehyde dehydrogenase from *E. coli* (GenBank Accession No. Y09555) and alcohol dehydrogenase from *Z. mobilis* (GenBank Accession No. M32100) have been isolated and sequenced. The genes encoding for these enzymes can be cloned into a 3-HP-CoA producing organism or cell by well-known molecular biology techniques. Expression of these enzymes in 3-HP-CoA producing organisms or cells will impart it the ability to convert 3-HP-CoA to 1,3-propanediol. The substrate specificity of these enzymes for 3-HP-CoA can be changed or improved using well-known techniques such as error prone PCR or mutator *E. coli* strains.

Conversion of 3-HP to 1,3-propanediol can be achieved by contacting 3-HP with enzymes having aldehyde dehydrogenase (NAD(P)+) (EC 1.2.1.-) and alcohol dehydrogenase (EC 1.1.1.1) activity. Such conversion can be performed in vivo, in vitro, or a combination thereof. For example, cloning and expressing these genes in a 3-HP producing microorganism or cell will impart the ability of the cell or organism to convert 3-HP to 1,3-propanediol. The substrate specificity of these enzymes for 3-HP-CoA can be changed or improved using well-known techniques as described above.

The formation of 1,3-propanediol during fermentation or in an in vitro assay can be analyzed using a High Performance Liquid Chromatography (HPLC). The chromatographic separation can be achieved by using a Bio-Rad 87H ion-exchange column. A mobile phase of 0.01N sulfuric acid is passed at a flow rate of 0.6 ml/min and the column maintained at a temperature of 45-65° C. The presence of 1,3-propanediol in the sample can be detected using a refractive index detector (Skraly et al., *Appl. Environ. Microbiol.* 64:98-105, 1998).

EXAMPLE 1

Cloning a *Bacillus subtilis* lysine 2,3-aminomutase (KAM gene)

To identify an alanine 2,3-aminomutase that produces beta-alanine for alanine, enzymes which carry out similar reactions, but which do not accept alanine or beta-alanine as substrates, were randomly mutated and then screened to identify mutant enzymes that have alanine 2,3-aminomutase activity. This example describes cloning lysine 2,3-aminomutase (E.C. 5.4.3.2) from *Bacillus subtilis* (SEQ ID NO: 3 and 31). One skilled in the art will understand that similar methods can be used to clone a lysine 2,3-aminomutase from any desired organism.

The *B. subtilis* lysine 2,3-aminomutase was chosen because it was reported to be stable to air, thus permitting selection for activity under both anaerobic and aerobic conditions. In addition, because this enzyme has lower specific activity than the lysine 2,3-aminomutase of *C. subterminale*, deleterious effects to the *E. coli* host by overexpression of active lysine 2,3-aminomutase or alanine 2,3-aminomutase were reduced.

To clone the *B. subtilis* KAM gene encoding lysine 2,3-aminomutase, the following methods were used. *B. subtilis* ATCC 6051 was obtained from ATCC (American Type Culture Collection (ATCC), Manassas, Va.) and chromosomal DNA prepared using the Genomic Tip 20/G (Qiagen, Valencia, Calif.) following the procedure recommended by the manufacturer. Primers designed to amplify the KAM gene by PCR were based on the complete *B. subtilis* genome sequence (GenBank Accession No: NC 000964) and the sequences disclosed in Chen et al. (Biochem. J. 348:539-49, 2000) and in U.S. Pat. No. 6,248,874. The PCR primers:

GCGCGAGGAGGAGTT CATATGAAAAACAAATGGTATAAAC (SEQ ID NO: 1), and

CGGGCACCGCTTCGAG GCGGCCGCACCATTCGCATG (SEQ ID NO: 2) were used, where the underlined nucleotides are the NdeI and NotI sites used for cloning the PCR product into plasmids.

The PCR reaction (100 μl total volume) contained 0.5 μg *B. subtilis* chromosomal DNA, 0.2 μM each primer (SEQ ID NOS: 1 and 2), 10 μL 10×PfuTurbo reaction buffer (Stratagene, Inc., La Jolla, Calif.), 0.2 mM each nucleotide triphosphate, and 5 units of PfuTurbo DNA polymerase (Stratagene). The PCR reaction was heated at 95° C. for 2 minutes, then subjected to 30 cycles of 95° C. for 30 seconds, 58° C. for 30 seconds, 72° C. for 2 minutes, and then held at 72° for an additional 10 minutes.

The resulting PCR product was precipitated by the addition of 3 μl Pellet Paint Co-Precipitant (Novagen, Inc., Madison, Wis.), 100 μl 5M ammonium acetate, and 400 μl ethanol. The resuspended reaction was digested with NdeI and NotI (New England Biolabs, Inc., Beverly, Mass.), purified with the QIAquick PCR Purification Kit (Qiagen), and ligated with the Rapid DNA Ligation Kit (Roche Molecular Biochemicals, Indianapolis, Ind.) into pET-22b (+) (Novagen) or pPRONde digested with the same enzymes to generate the plasmids pET-KAM1 and pPRO-KAM1, respectively. Plasmid pPRONde is a derivative of pPRO-Lar.A122 (Clontech Laboratories, Inc., Palo Alto, Calif.) in which an NdeI site was constructed at the intiator ATG codon by oligonucleotide-directed mutagenesis using the QuikChange Site-Directed Mutagenesis kit from Stratagene. Expression of lysine 2,3-aminomutase in these vectors is driven by the T7 promoter in pET22(b) or a hybrid lac/ara promoter in pPRO-Nde. Ligations were transformed into *E. coli* DH5α (Life Technologies, Gaithersburg, Md.) and clones verified by sequencing. The *B. subtilis* KAM gene is shown in SEQ ID NO: 3 (the amino acid sequence is shown in SEQ ID NO: 31), and was mutagenized as described below, to identify mutants having alanine 2,3-aminomutase activity.

EXAMPLE 2

In Vitro Mutagenesis of a *B. subtilis* KAM Gene

To introduce mutations into the *B. subtilis* KAM gene (SEQ ID NO: 3) in vitro, several error-prone PCR methods were used. Similar methods can be used to introduce mutations into any KAM gene encoding a lysine 2,3-aminomutase, such as a KAM gene from *Deinococcus radiodurans* (GenBank Accession No: RDR02336), which is 52% identical to the *B. subtilis* KAM protein sequence, *Clostridium subterminale* (GenBank Accession No: AF159146), or *P. gingivalis* (Incomplete genome, The Institute for Genomic Research, see EXAMPLE 5).

In one method, a GeneMorph PCR Mutagenesis Kit (Stratagene) was used as follows. Reactions of 50 μL were set up with 10, 1, 0.1, or 0.01 ng of template pET-KAM1 DNA and 125 ng each of the T7 promoter primer and the T7 terminator primer (sequences as given in the Novagen product catalog) as recommended by the manufacturer, heated at 94° C. for 30 seconds, subjected to 30 cycles of 94° C. for 30 seconds, 50° C. for 30 seconds, 72° C. for 2 minutes, and then held at 72° for an additional 10 minutes.

The resulting PCR products were precipitated with 3 μl Pellet Paint Co-Precipitant (Novagen), 50 μl 5M ammonium acetate, 200 μl ethanol, resuspended, digested with NdeI and NotI, and 120 ng of each mutagenic PCR product was ligated to pPRONde digested with the same endonucleases using the Rapid DNA Ligation Kit (Roche Molecular Biochemicals). The ligation mixes were digested with restriction endonuclease BamHI (New England Biolabs) to linearize residual vector DNA without insert, precipitated with ethanol as described, and transformed into electrocompetent ElectroMax DH10B *E. coli* cells (Invitrogen, Carlsbad, Calif.). Kanamycin-resistant transformants from each library, containing 15,000-20,000 clones, were scrapped off the selection plates and the mutagenized plasmid libraries prepared using Plasmid Midi Kit (Qiagen).

In a second method, based on the Mn-dITP PCR method of Xu et al. (BioTechniques 27:1102-8, 1999), an initial round of manganese-induced error-prone PCR was conducted using pET-KAM1 DNA as template and primers homologous to the T7 promoter and T7 terminator regions. The reaction mixture (50 μL) contained 1×Taq PCR buffer with 2 mM $MgCl_2$, 100 ng of DNA, 40 μM $MnCl_2$, 0.2 μM of each primer, 200 μM of each dNTP, and five units of Taq polymerase (Roche Molecular Biochemicals). The PCR program included of an initial denaturation at 94° C. for 2 minutes; 20 cycles of 94° C. for 30 seconds, 54° C. for 1 minute, and 72° C. for 2.25 minutes; and a final extension at 72° C. for 7 minutes.

Three microliters of PCR product was used as template in a second round of PCR using dITP to enhance mispairing of nucleotides during amplification. The second-round PCR mixture (100 μL) contained 1×Taq polymerase PCR buffer with 2 mM $MgCl_2$, 40 μM dITP, 0.2 μM of each primer. 200 μM of each dNTP, and 10 units of Taq DNA polymerase. The PCR program was identical to that for the first round but consisted of 30 cycles. The PCR product was separated on a 1% TAE-agarose gel and purified using a QIAquick Gel Purification procedure (Qiagen). The purified PCR product was digested with the restriction enzymes NdeI and NotI and ligated into pPRO-Nde vector that had been digested with the same enzymes, gel purified, and dephosphorylated with shrimp alkaline phosphatase (Roche). The ligation reaction was conducted using T4 DNA ligase (New England BioLabs) at 16° C. for 16 hours, after which another volume of 1× ligation buffer and ligase was added and the reaction continued for two hours at room temperature.

The ligation reaction was purified using a QIAquick PCR Purification column and eluted in 30 μL of water. Two microliters of the reaction were transformed into *E. coli* Electromax™ DH10B™ (Life Technologies, Inc.) cells and plated on LB media containing 25 μg/mL of kanamycin. Control ligations indicated a background level (vectors with no insert) of less than 3%. Multiple transformations were done to obtain approximately 40,000 colonies. Colonies were scrapped from plates and plasmid DNA prepared using the Qiagen MiniSpin Plasmid procedure. Plasmid DNA was precipitated with ammonium acetate and ethanol to increase its concentration before transformation into selection hosts. Plasmid DNA was also isolated from single colonies and sequenced to obtain an estimate of the mutation rate. The average mutation rate with this method was 1.3 altered nucleotides per Kb.

In a third method, mutagenic PCR was conducted based on the protocol of Cadwell and Joyce (*PCR Methods Appl.* 2:28-33, 1992). This method used various dilutions of a mutagenic buffer containing 21.2 mM $MgCl_2$, 2.0 mM $MnCl_2$, 3.2 mM dTTP,: and 3.2 mM dCTP. The following volumes of mutagenic buffer were added to separate PCR reactions (each of final volume 100 µl): 0, 1.56, 3.13, 6.25, 12.5, and 25 µL, in addition to 1×Taq PCR buffer with 1.5 mM $MgCl_2$.0.25 µM of each primer, 200 µM of each dNTP, 50 ng of pET-KAM1 template DNA, and 10 units of Taq DNA polymerase (Roche). The PCR program included an initial denaturation at 94° C. for 2 minutes; 30 cycles of 94° C. for 30 seconds, 54° C. for 1 minute, and 72° C. for 2.25 minutes; and a final extension at 72° C. for 7 minutes.

Following PCR, the reactions were treated to eliminate the Taq polymerase by adding EDTA to a final concentration of 5 mM, SDS to 0.5%, and proteinase K to 50 µg/mL (Matsumura and Ellington, Mutagenic PCR of Protein-Coding Genes for In Vitro Evolution. Methods in *Molecular Biology*. Vol 182: In Vitro Mutagenesis, $2^{nd}$ ed. Ed. J. Braman Hamana. Press Inc. Totowa, N.J., 2001). The reactions were heated to 65° C. for 15 minutes and gel purified as described above. The first four treatments produced sufficient PCR product for cloning. PCR product was digested, ligated into pPRO-Nde, and transformed into *E. coli* Electromax™ DH10B™ cells. Plasmid DNA was isolated from single colonies and sequenced to obtain an estimate of the mutation rate. The average mutation rate for treatments 1-4 varied from 0 to 0.47% (0 to 4.7 altered nucleotides per Kb). Multiple transformations were conducted to obtain approximately 50,000 colonies for each selected treatment. Colonies were scrapped from plates and plasmid DNA prepared using a Qiagen MiniSpin Plasmid procedure. Plasmid DNA was precipitated with ammonium acetate and ethanol to increase its concentration before transformation into selection hosts.

EXAMPLE 3

In Vivo Mutagenesis of a *B. subtilis* KAM Gene

To introduce mutations into the *B. subtilis* KAM gene (SEQ ID NO: 3) in vivo, pPRO-KAM1 was passaged through the *E. coli* XL1Red (Stratagene) mutator strain. Approximately 50 ng of plasmid pPRO-KAM1 was transformed into competent XL1-Red cells as directed by the manufacturer, and transformants plated on LB medium containing 25 µg/ml kanamycin. Approximately 200 transformants selected at random were scrapped off the transformation plates and inoculated into two portions of 5 ml LB broth containing 25 µg/ml kanamycin. One portion was grown overnight at 30° C., the other at 37° C.

A small aliquot of each portion was inoculated into fresh LB broth containing 25 µg/ml kanamycin, while mutagenized plasmid DNA was extracted from 1.5 ml of each culture using the QiaSpin Mini kit (Qiagen). Overnight growth and plasmid DNA extraction was repeated two more times, generating mutagenized plasmid libraries from two different temperatures and three cycles of increasing exposure to the mutator strain. The plasmid DNAs were concentrated by ethanol precipitation prior to transformation into selection strains.

EXAMPLE 4

Construction of *E. coli* ΔpanD::CAT Strain

To identify genes encoding polypeptides that can perform the alanine 2,3-aminomutase reaction, an efficient screen or selection for the desired activity is needed. Therefore, a selection method was developed by recognizing that *E. coli* uses beta-alanine for the synthesis of pantothenic acid which in turn is a component of coenzyme A (CoA) and of acyl carrier protein (ACP). CoA and ACP are the predominant acyl group carriers in living organisms, and are essential for growth.

In *E. coli*, the primary route to beta-alanine is from aspartate in a reaction catalyzed by aspartate decarboxylase (E.C. 4.1.1.11), which is encoded by the panD gene (FIG. 3). A functional deletion mutation of panD results in beta-alanine auxotrophy and growth inhibition, which can alleviated by the exogenous addition of pantothenate or beta-alanine, or by the production of beta-alanine from another source.

Two *E. coli* strains were used in the screen, both of which are deficient in beta-alanine synthesis. The strain DV 1 (#6865, *E. coli* Genetic Stock Center, New Haven Conn.; Vallari and Rock, *J. Bacteriol.* 164:136-42, 1985) is an *E. coli* mutant made by chemical mutagenesis, which has host (chromosomal) mutations of both the panF and panD genes which renders both genes non-functional.

The panF gene encodes the uptake of pantothenate from the medium, and thus the combination of panD and panF provides a more stringent requirement for beta-alanine for growth. Therefore, although the DV1 strain was known, its use for selecting cells having alanine 2,3-aminomutase activity was not previously known.

The other selection strain, BW25113 ΔpanD::CAT, includes a deletion of the panD locus, to prevent revertants of the panD mutation which would be able to grow without exogenous beta-alanine. This strain, which has an insertion of a chloramphenicol resistance marker conferred by the CAT gene into the panD locus, was constructed using the gene inactivation method of Datsenko and Wanner (*Proc. Natl. Acad. Sci. USA* 97: 6640-5, 2000) using *E. coli* strains BW25113/pKD46 and BW 25141/pKD3 for the *E. Coli* Genetic Stock Center.

The CAT gene of pKD3 was amplified using primers TATCAATTCGTTACAGGCGATACATGGCACGCTTC-GGCGCGTGTAGGCTGGAGCTGCTTC (SEQ ID NO: 4) and GATGTCGCGGCTGGTGAGTAACCAGCCGCAGGGA-TAACAACATATGAATATCCTCCTTAG (SEQ ID NO: 5), where the underlined sequence corresponds to the regions in the *E. coli* chromosome immediately upstream and downstream of the panD locus, respectively, and the non-underlined regions are homologous to regions in pKD3 that permit amplification of a fragment containing the CAT gene. The PCR reaction included 30 µl 10× concentrated PCR buffer (Roche Molecular Biochemicals), plasmid pKD3, 0.2 mM each dNTP, 0.21M each primer, and 15 units Taq polymerase (Roche Molecular Biochemicals) in a final volume of 300 µl. The PCR reaction was incubated at 95° C. for 30 seconds followed by 30 cycles of 95° C. for 30 seconds, 45° C. for 30 seconds, 72° C. for 1 min, then 72° C. for 10 min. The PCR product was precipitated with ethanol, digested with Dpnl, purified with the QIAquick PCR Purification Kit (Qiagen), and transformed into BW25113/pKD46 expressing the recombination functions. Transformants were plated on LB plates containing 25 μg/ml chloramphenicol and 5 μM beta-alanine.

Chloramphenicol-resistant transformations were single-colony purified on non-selective LB medium supplemented with 5 μM beta-alanine at 43° C., and single colonies tested for retention of chloramphenicol resistance, loss of ampicillin resistance (indicating curing of pKD46), and requirement for beta-alanine for growth on M9-glucose minimal medium. Confirmation of correct insertion of the CAT gene into the panD locus was carried out by colony PCR of the resultant ΔpanD::CAT strain using primers that flank the insertion locus (TTACCGAGCAGCGTTCAGAG, SEQ ID NO: 6; and CACCTGGCGGTGACAACCAT, SEQ ID NO: 7). While the wild-type panD locus is expected to yield a PCR product of 713 basepairs, the ΔpanD::CAT construct yielded a 1215-basepair product. A derivative of the ΔpanD::CAT strain, in which the inserted CAT gene is removed by the activity of the FLP recombinase encoded by plasmid pCP20, was constructed as described previously (Datsenko and Wanner, *Proc. Natl. Acad. Sci. USA* 97: 6640-5, 2000). This strain is referred to as ΔpanD.

Figure 2:
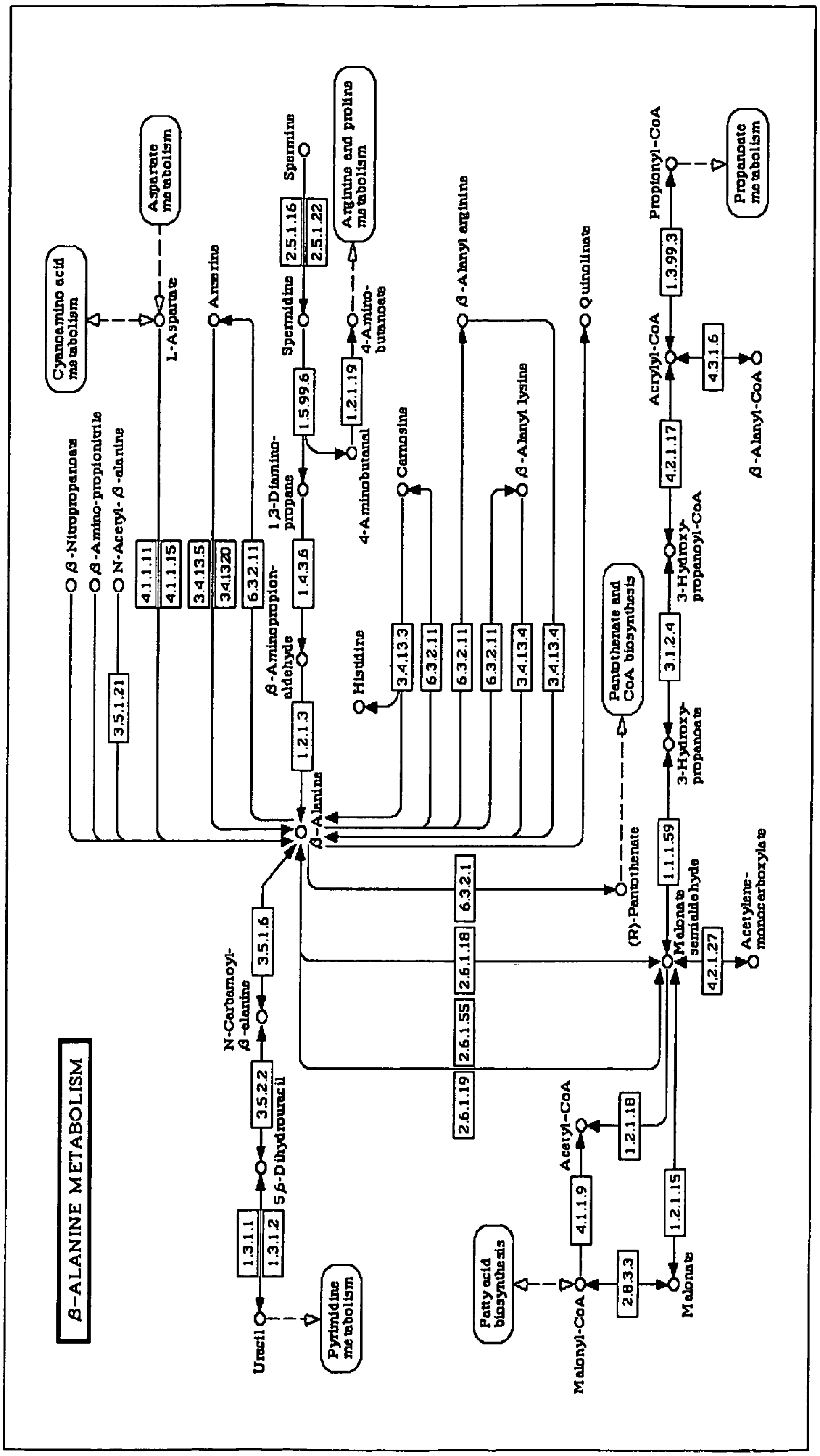
FIG. 2 is a diagram of a pathway for generating beta-alanine.

A secondary route to beta-alanine exists in *E. coli* based on the reductive pathway of uracil catabolism (West, *Can. J. Microbiol.* 44: 1106-9, 1998, FIG. 2). In this pathway, uracil is reduced to dihydrouracil by the enzyme dihydropyrimidine dehydrogenase (E.C. 1.3.1.2). Dihydrouracil is then converted by dihydropyrimidinase (E.C. 3.5.2.2) to N-carbamoyl-beta-alanine, which in turn is hydrolyzed by N-carbamoyl-beta-alanine amidohydrolase (E.C. 3.5.1.6) to beta-alanine, $CO_2$, and $NH_3$. To prevent the formation of beta-alanine by this pathway, the gene encoding dihydropyrirnidine dehydrogenase, yeiA (GenBank Accession No. AAC75208), was insertionally deleted by the method of Datsenko and Wanner as described above. The CAT gene of pKD3 was amplified using primers GCGGCGTGAAGTTTCCCAACCCGTTCTGCCTCTCT-TCTCGTGTAGGCTGGAGCTGCTTC (SEQ ID NO: 8), and TTACAACGTTACCGGGTGTTCTTTCTCGCCTTTCTT-AAACCATATGAATATCCTCCTTAG (SEQ ID NO: 9), where the underlined sequence corresponds to the regions in the *E. coli* chromosome immediately upstream and downstream of the yeiA locus, respectively, and the non-underlined sequence are homologous to the regions in pKD3 that permit amplification of a fragment containing the CATgene. Chloramphenicol-resistant insertion mutants were isolated as described above, and the resistance marker transduced into the ΔpanD strain to generate the double mutant ΔpanD/ΔyeiA::CAT.

Electrocompetent cells of *E. coli* BW 25115 ΔpanD::CAT, ΔpanD, or ΔpanD/ΔyeiA::CAT, were generated and used as hosts for the transformation of libraries of mutant lysine 2,3-aminomutase DNAs as described in EXAMPLE 6.

EXAMPLE 5

Cloning and In Vitro Mutagenesis of a *Porphyromonas Gingivalis* KAM Gene

The lysine 2,3-aminomutase gene from *Porphyromonas gingivalis* was amplified by PCR from genomic DNA and cloned into the NdeI and NotI sites of vector pET22B (Novagen). Mutagenic PCR was conducted by the method of Cadwell and Joyce (*PCR Methods Appl.* 2:28-33, 1992), using T7 promoter and T7 terminator primers for amplification and 6.25 μL or 9.38 μL of mutagenic buffer per 100 μL reaction. The PCR products were gel purified (Qiagen) and digested sequentially with NdeI and NotI. The digested PCR products were ligated into pPRONde vector and transformed into *E. coli* Electromax™ DH10B™ as described in EXAMPLE 2. Multiple transformations were conducted to obtain at least 60,000 colonies per mutation treatment. Colonies were scrapped from plates and plasmid DNA was prepared and precipitated to increase its concentration. The resulting libraries had mutation rates of 0.3% and 0.35%.

EXAMPLE 6

Identification of Clones having Alanine 2,3-Aminomutase Activity

The mutagenized lysine 2,3-aminomutase plasmid libraries generated above in EXAMPLE 2 was transformed into electrocompetent *E. coli* strain DV 1 cells. Transformants were plated on LB containing 25 μg/ml kanamycin at the appropriate dilution to obtain an estimate of total transformants and on M9 minimal medium supplemented with 0.4% glucose, 0.2% Vitamin Assay Casamino Acids (DIFCO/Becton Dickinson, Sparks, Md.), and 25 μg/ml kanamycin (Sigma, St. Louis, Mo.). For some selections, IPTG was added to 0.25 mM.

The ΔpanD::CAT strain of *E. coli* described in EXAMPLE 4 was transformed in a similar manner with libraries generated in EXAMPLES 2, 3, and 5, except that transformants were plated on M9 minimal medium supplemented with 0.4% glucose, and 25 μg/ml kanamycin (Sigma, St. Louis, Mo.). For some selections on *B. subtilis* libraries, IPTG was added to 0.25 mM, $Fe_2(NH_4)_2SO_4$ was added to 50 μM, and chloroamphenicol was added to 25 μg/mL. For some selections on *P. gingivalis* libraries, IPTG was added to 50 μM, $Fe_2(NH_4)_2SO_4$ was added to 50 μM, chloroamphenicol was added to 25 μg/mL, L-alanine was added to 1 mg/mL and L-lysine was added to 2 mg/mL.

Transformants growing on the minimal medium plates arose at a frequency of approximately $1\times10^{-4}$ relative to the number to total transformants as measured by the number of colonies growing on LB plus 25 μg/ml kanamycin. Plasmid DNA from the colonies growing on minimal medium was prepared using the Qiagen Miniprep kit and retransformed into the ΔpanD::CAT strain of *E. coli* to confirm that the ability to grow in the absence of added beta-alanine was conferred by a function carried by the plasmid. Plasmid DNA was prepared from retransformed colonies and the kam gene sequenced to determine any changes relative to the wildtype *B. subtilis* or *P. gingivalis* kam gene sequences.

A mutated *B. subtilis* kam gene sequence, which encodes for an alanine 2,3-aminomutase, is shown in SEQ ID NO: 20, and the corresponding amino acid sequence shown in SEQ ID NO: 21. The plasmid carrying this sequence is designated pLC4-7LC1. There were three amino acid changes observed in the mutated sequence, as compared to the wildtype *B. subtilis* kam gene sequence (FIG. 4). There was a L103M substitution, a M136V substitution, and a D339H substitution in the alanine 2,3-aminomutase protein (where the first amino acid is the wild-type sequence, the number is the amino acid position, and the second amino acid is the sequence observed in the alanine 2,3-aminomutase sequence). The FeS cluster-binding motif (amino acids 134-146 of SEQ ID NO: 21) and the putative PLP-binding motif (amino acids of 288-293 SEQ ID NO: 21) are also shown in FIG. 4. This is the first demonstration of alanine 2,3-aminomutase nucleic acid and amino acid sequences.

A mutated *P. gingivalis* kam gene sequence, which encodes for an alanine 2,3-aminomutase, is shown in SEQ ID NO. 29, and the corresponding amino acid sequence shown in SEQ ID NO 30. There were five amino acid changes observed in the mutated sequence, as compared to the wildtype *P. gingivalis* sequence (FIG. 5). There was a N19Y substitution, a L53P substitution, a H85Q substitution, a D331 G substitution, and a M342T substitution in the alanine 2,3-aminomutase protein. However, it is possible that not all of these mutations are necessary to have alanine 2,3-aminomutase activity. In aligning the *B. subtilis* and *P. gingivalis* mutant proteins, the *P. gingivalis* D331G substitution is located at the corresponding location within the protein as the *B. subtilis* D339H sustitution (FIG. 6), indicating that it may be of particular importance. The FeS cluster-binding motif (amino acids 126-138 of SEQ ID NO: 30) and the putative PLP-binding motif (amino acids 280-285 of SEQ ID NO: 30) are also shown in FIG. 5. This is another demonstration of alanine 2,3-aminomutase nucleic acid and amino acid sequences.

The ability of the mutated kam genes to convert alpha-alanine to beta-alanine, and thus to allow production of pantothenate, was determined using liquid growth tests that compare the growth of ΔpanD transformants in minimal media containing panthothenate with growth in media lacking pantothenate. The starting inoculum included washed cells from a growing culture, or cells scrapped from a plate.

As an example of using washed cells as inoculum, 3-5 mL cultures were started from single colonies and grown overnight at 30° C. in LB broth plus 40 μg/ml kanamycin. The $OD_{600}$ of the cultures were read and equivalent numbers of cells from each culture harvested by centrifugation (approximately 600 total OD×μL, e.g. OD 4.0×150 μL). The cells were washed twice with 0.85% NaCl, resuspended in 200 μL 0.85% NaCl, and 30 μL was used to inoculate 3 ml of M9-based minimal media (6 g/L $Na_2HPO_4$, 3 g/L $KH_2PO_4$, 0.5 g/L NaCl, 1 g/L $NH_4Cl$, 2 mM $MgSO_4$, 4 g/L glucose, 1 mM $CaCl_2$, 250 μM IPTG, 40 μg/mL kanamycin, 50 μM $Fe(NH_4)_2(SO_4)_2$) in glass 13 mm diameter tubes to a starting $OD_{600}$ of about 0.05. Control cultures contained either minimal media supplemented with 20 μM pantothenate, or LB broth with 40 μg/mL kanamycin. Cultures were grown at 37° C. without shaking for about 18 hours and the $OD_{600}$ measured.

As shown in Table 1, whereas the cells carrying the vector control grew in minimal medium without added pantothenate or beta-alanine to an average $OD_{600}$ of 0.21 using residual reserves of pantothenate or beta-alanine (approximately 30% of the $OD_{600}$ achieved in the presence of pantothenate), the cells carrying the alanine 2,3-aminomutase clone grew to an average $OD_{600}$ of 0.50, approximately 90% of that achieved in the presence of pantothenate. The addition of $Fe^{2+}$ did not increase the growth of the vector control cells, but allowed the alanine 2,3-aminomutase-bearing cells to achieve growth densities equal to that obtained in the presence of pantothenate or in rich LB broth medium. This indicates that the alanine 2,3-aminomutase gene provides a source of beta-alanine that complements the panD mutation.

TABLE 1

Growth test

| Plasmid | Replicate | Medium Minimal ($OD_{600}$) | Minimal + $Fe^{2+}$ | Minimal + pantothenate | LB |
|---|---|---|---|---|---|
| pPRONde | 1 | 0.206 | 0.210 | 0.670 | 0.647 |
| | 2 | 0.217 | 0.209 | 0.683 | 0.640 |
| pLC4-7LC1 | 1 | 0.458 | 0.550 | 0.522 | 0.572 |
| | 2 | 0.460 | 0.541 | 0.576 | 0.552 |

As an example of using plated cultures as inoculum, a colony was scrapped off a plate and resuspended in 50 μL of minimal media lacking pantothenate. The resuspension (20 μL) was used to inoculate 1 mL of minimal media in a 1.5 mL microtube and 20 μL was used to inoculate one mL of minimal media supplemented with pantothenate. The latter culture served as a control for the varying amount of inoculum added. The response of the culture to growth without pantothenate was expressed as a ratio of growth on media lacking pantothenate to growth on media containing pantothenate. Cultures were grown at 25-37° C. for 1-3 days with no shaking and $OD_{600}$ measured. A more anaerobic growth test was obtained by filling tubes to a greater extent. This was helpful in testing the *P. gingivalis* mutants.

TABLE 2

Test with scrapped colonies/semi-anaerobic.

| | $OD_{600}$:M9 | $OD_{600}$:M9 + pantothenate | Ratio $OD_{600}$:M9/$OD_{600}$:M9 + pantothenate |
|---|---|---|---|
| Pg aam | 0.711 | 0.791 | 0.90 |
| Pg aam | 0.617 | 0.77 | 0.80 |
| Pg aam | 0.702 | 0.811 | 0.87 |
| Pg aam | 0.712 | 0.879 | 0.81 |
| Pg aam | 0.689 | 0.843 | 0.82 |
| Pg aam | 0.719 | 0.851 | 0.84 |
| pPRONde | 0.148 | 0.824 | 0.18 |
| Bs aam | 0.783 | 0.801 | 0.98 |
| Bs aam | 0.777 | 0.838 | 0.93 |
| Pg kam | 0.064 | 0.792 | 0.08 |
| Pg kam | 0.195 | 0.876 | 0.22 |

Pg aam = Cells with plasmid carrying mutated *P. gingivalis* kam gene with alanine 2,3-aminomutase activity
Bs aam = Cells with plasmid carrying mutated *B. subtilis* kam gene with alanine 2,3-aminomutase activity
Pg kam = Cells with plasmid carrying wildtype *P. gingivalis* kam gene

EXAMPLE 7

Generation of Indivudual Mutations in *B. subtilis* Lysine 2,3-Aminomutase

The mutations identified in the wildtype *B. subtilis* lysine 2,3-aminomutase gene above in EXAMPLE 5 were individually constructed in the wildtype *B. subtilis* lysine 2,3-aminomutase gene (SEQ ID NO: 3) using the Stratagene QuikChange™ Site-Directed Mutagenesis Kit. The oligonucleotides used to generate the L103M mutation were: CACAAAACAAAATACGATATGGAAGAC-CCGCTCCATGAGGATGAAGATTCA (SEQ ID NO: 10), and TGAATCTTCATCCTCATGGAGCGGGTCT- TCCATATCGTATTTTGTTTTGTG (SEQ ID NO: 11). The oligonucleotides used to generate the M136V mutation were: GAATCAATGTTCCGTATACTGCCGCTAC (SEQ ID NO: 12), and GTAGCGGCAGTATACGGAACATTGATTC (SEQ ID NO: 13). The oligonucleotides to generate the D339H mutation were: GTTCCTACCTTTGTTGTACACGCACCAGGCG (SEQ ID NO: 14), and CGCCTGGTGCGTGTACAACAAAGGTAGGAAC (SEQ ID NO: 15).

Using the liquid growth test described in EXAMPLE 6, cells with plasmids carrying the L103M mutation alone were capable of growth in minimal medium without added pantothenate or beta-alanine, however not to the same extent as cells with plasmid pLC4-7LC1, whereas those carrying the M136V or D339H mutations alone had the host ΔpanD phenotype. Combinations of the L103M mutation with the M136V and D339H mutations in an otherwise wildtype *B. subtilis* kam sequence yielded a gene that confered the same ability to grow in the absence of beta-alanine or pantothenate as did pLC4-7LC1, confirming that these three mutations, or a subset of them, are sufficient to confer alanine 2,3-aminomutase activity.

One skilled in the art will understand that alternative substitutions in these positions can be generated. Thus, using oligonucleotides similar to SEQ ID NOS: 10 and 11 in which the codon corresponding to L103 was randomized, mutants with substitutions L103K, L103R, L103E, and L103S were obtained that conferred to the ΔpanD strain the ability to grow in the absence of beta-alanine or pantothenate. Further, using oligonucleotides similar to SEQ ID NO: 14 and 15 in which the codon corresponding to D339 was randomized, mutants with substitutions D339Q, D339T, D339N, were obtained that conferred to the ΔpanD strain the ability to grow in the absence of beta-alanine or pantothenate.

EXAMPLE 8

Selection for Alanine 2,3-Aminomutase Activity without Using Mutagenized Lysine 2,3-Aminomutase An alternative method to identifying cells having alanine 2,3-aminomutase activity is to plate cells, such as the DV1 or ΔpanD::CAT cells described above, on the media described above, without transfecting them with the mutagenized lysine 2,3-aminomutase library. Such cells are selected as described above, and verified for the presence of alanine 2,3-aminomutase activity as described in EXAMPLES 6 and 9.

Cells can be mutagenized before plating, for example by exposing the cells to UV irradiation or chemicals (such as MES). This permits isolation of mutants having mutations in one or more other genes which result in the cell having alanine 2,3-aminomutase activity.

Alternatively, the cells can be unaltered before plating (e.g. not transformed, not mutagenized). This method permits isolation of naturally occurring strains having alanine 2,3-aminomutase activity.

EXAMPLE 9

Demonstration of Alanine 2,3-Aminomutase Activity

Cells obtained using the screening methods described above were verified for their alanine 2,3-aminomutase activity. For cells that were transformed with a mutagenized library (EXAMPLES 2, 3 and 5), plasmids were isolated from selection host using standard molecular biology methods. The resulting plasmids were retransformed into the selection host, the plasmids reisolated, and the resulting clones sequenced as described in EXAMPLE 6. For untransformed cells (EXAMPLE 8), the gene conferring the alanine 2,3-aminomutase activity can be cloned, for example using shotgun cloning.

Several assays can be used to assay for alanine 2,3-aminomutase activity, such as measuring biosynthesis of $[^{13}C]$coenzyme A from $[3-^{13}C]$alanine via $[3-^{13}C]$beta-alanine, by using an enzyme assay that measures the conversion of alpha-alanine to beta-alanine, or an assay that measures the presence of beta-alanine in cells or extracts of cells carrying alanine 2,3-aminomutase.

Biosynthesis of $[^{13}C]$coenzyme A from $[3-^{13}C]$alpha-alanine via $[3-^{13}C]$beta-alanine Insertional deletion of the panD gene, whose gene product (aspartate 1-decarboxylase) catalyzes the production of beta-alanine from aspartate, results in pantothenate deficiency and hence the inability to produce coenzyme A. However, ΔpanD cells possessing an alanine 2,3-aminomutase capable of producing beta-alanine from alpha-alanine would be able to bypass this deficiency; in particular, these cells, when grown in the presence of $[3-^{13}C]$alpha-alanine, would incorporate the $[^{13}C]$ label into coenzyme A. This test was used to confirm that the *B. subtilis* alanine 2,3-aminomutase sequence isolated in EXAMPLE 6 (SEQ ID NOS: 20 and 21) could catalyze the conversion of alpha-alanine to beta-alanine.

Cells of *E. coli* ΔpanD/ΔyeiA::CAT transformed with pPRONde, pPRO-KAM1, or pLC4-7LC1 were grown overnight at 37° C. in minimal medium (EXAMPLE 6) except with 25 μg/ml kanamycin and 10 μM $Fe(NH_4)_2(SO_4)_2$, and with 1 mM alanine (unlabeled), and 10 μM beta-alanine. The cultures were diluted 100-fold in minimal medium with 25 μg/ml kanamycin,. 10 μM $Fe(NH_4)_2(SO_4)_2$, and 11 mM $[3-^{13}C]$alpha-alanine (99%, Cambridge Isotope Laboratories, Andover, Mass.) but no unlabeled alpha-alanine or beta-alanine. Following growth at 30° C. for approximately 20 hours, the cells were recovered by centrifugation and extracts generated by the method of Jaskowski and Rock (J. Bacteriol. 148: 926-32, 1981) in the presence of 10 mM dithiothreitol to convert thioesters of coenzyme A to the free sulfhydryl form.

The extracts were analyzed using a Micromass ultima LC/MS system which included of a Waters 2690 liquid chromatograph with a Waters 996 Photo-Diode Array (PDA) absorbance monitor placed in series between the chromatograph and the triple quadrupole mass spectrometer. LC separations were made using a 4.6×150 mm YMC ODS-AQ (3 μm particles, 120 Å pores) reversed-phase chromatography column at room temperature. Gradient elution of the analytes was performed using aqueous 25 mM ammonium acetate containing 0.5% (v/v) acetic acid (Buffer A), and acetonitrile containing 0.5% (v/v) acetic acid (Buffer B). The elution was isocratic at 10% B, 0-10 min, then linear from 10% B to 100% B, 10-12 min. The flow rate was 0.250 mL/min and photodiode array UV absorbance was monitored from 200 nm to 400 nm. All parameters of the electrospray MS system were optimized and selected based on generation of protonated molecular ions ($[M+H]^+$) of the analytes of interest, and production of characteristic fragment ions. The following instrumental parameters were used for ESI-MS detection of Coenzyme A in the positive ion mode: capillary: 4.0 V; cone: 80 V; hex 1: 25 V; aperture: 0 V; hex 2: 0 V; source temperature: 100° C.; desolvation temperature: 350° C.; desolvation gas: 500 L/h; cone gas: 40 L/h; low mass resolution: 15.0; high mass resolution: 15.0; ion energy: 0; multiplier: 650. Uncertainties for reported mass/charge ratios (m/z) and molecular masses are ±0.01%. The ratio of peak areas with m/z 769 ([$^{13}$C]coenzyme A) to peak area with m/z 768 (unlabeled coenzyme A) are shown in Table 3.

TABLE 3

Biosynthesis of [$^{13}$C]Coenzyme A

| Plasmid or sample | Ratio m/z = 769:m/z = 768 |
|---|---|
| Coenzyme A standard | 0.26 |
| pPRONde | 0.36 |
| pPRO-KAM1 | 0.53 |
| pLC4-7LC1 | 1.90 |

The results shown in Table 3 confirm that cells bearing the plasmid carrying the mutant with alanine 2,3-aminomutase activity (SEQ ID NOS: 20 and 21), when grown on [$^{13}$C] alpha-alanine, produce a higher ratio of [$^{13}$C]coenzyme A to [$^{12}$C]coenzyme A compared to normal abundance [$^{13}$C] coenzyme A or with cells bearing either the vector or the wildtype *B. subtilis* lysine 2,3-aminomutase gene. This demonstrates that the alanine 2,3-aminomutase sequence can produce beta-alanine, an obligatory intermediate in the biosynthesis of coenzyme A.

Enzyme Assays

An enzyme assay which measures the conversion of alpha-alanine to beta-alanine, or which measures for the presence of beta-alanine, can be performed to determine if a cell has alanine 2,3-aminomutase activity. For example, the method described by Chen et al. (*Biochem. J.* 348:539-49, 2000) to determine the lysine 2,3-aminomutase activity can be applied to the determination of alanine 2,3-aminomutase activity by substituting L-[U-$^{14}$C]alanine for L-[U-$^{14}$C]lysine in the incubation with reductively preincubated enzyme or cell extract, and separation of the radioactive alpha-alanine and beta-alanine by paper electrophoresis followed by scintillation counting of the spots corresponding to alpha-alanine and beta-alanine, respectively. Alternatively, the purified and reductively preincubated alanine 2,3-aminomutase can be incubated with alpha-alanine and the reaction mixture separated by high performance liquid chromatography to separate the product beta-alanine from alpha-alanine and quantify the product (Abe et al., *J. Chromatography B,* 712:43-9, 1998).

The formation of beta-alanine from alpha-alanine can also be monitored in whole cells of the *E. coli* ΔpanD::CAT strain transformed with a plasmid expressing an alanine 2,3-aminomutase by incubation of the cells in M9 minimal medium (Sambrook et al., *Molecular Cloning: A Laboratory Manual*, Cold Spring Harbor, N.Y., 1989) containing 0.4% (w/v) glucose, 25 μg/ml kanamycin (for a plasmid conferring resistance to kanamycin), 0.25 mM IPTG, and 1 mg/ml [$^{13}$C]-labeled alpha-alanine, extracting the cells, and detecting the [$^{13}$C]-beta alanine by high performance liquid chromatography/mass spectrometry using methods known by those skilled in the art.

EXAMPLE 10

Synthetic Operons for 3-HP Production from Beta-Alanine

Biosynthetic pathways that allow production of 3-HP via beta-alanine were generated (FIG. 1). One pathway to 3-HP from beta-alanine involves the use of a polypeptide having CoA transferase activity, that is, an enzyme from a class of enzymes that transfers a CoA group from one metabolite to the other. As shown in FIG. 1, beta-alanine can be converted to beta-alanyl-CoA using a polypeptide having CoA transferase activity and CoA donors such as acetyl-CoA or propionyl-CoA. Alternatively, beta-alanyl-CoA can be generated by the action of a polypeptide having CoA synthetase activity. The beta-alanyl-CoA can be deaminated to form acrylyl-CoA by a polypeptide having beta-alanyl-CoA ammonia lyase activity. The hydration of acrylyl-CoA at the beta position to yield 3-HP-CoA can be carried out by a polypeptide having 3-HP-CoA dehydratase activity. The 3-HP-CoA can act as a CoA donor for beta-alanine, a reaction that can be catalyzed a polypeptide having CoA transferase activity, thus yielding 3-HP as a product. Alternatively, 3-HP-CoA can be hydrolyzed to yield 3-HP by a polypeptide having specific CoA hydrolase activity.

These pathways use several enzymes that were cloned and expressed as described in WO 02/42418 (herein incorporated by reference) or below. *Megasphaera elsdenii* cells (ATCC 17753), *Chloroflexus aurantiacus* cells (ATCC 29365), *Clostridium propionicum* (ATCC 25522), *Clostridium acetobutylicum* (ATCC 824), *Pseudomonas aeruginosa* (ATCC 17933), *Bacillus subtilis* (ATCC 23857), *Alcaligenes faecalis* (ATCC 25094), and rat cDNA (Clontech, Palo Alto, Calif.) were used as sources of DNA. One skilled in the art will understand that similar methods can be used to obtain the sequence of these enzymes from any organism.

Individual genes were cloned, expressed and assayed prior to operon constructions. The synthetic operons for production of 3-HP in *E. coli* were cloned into pET-11a (5.7 kb) expression vector under control of the T7 promoter (Novagen), pPROLar.A (2.6 kb) vector with lac/ara-1-promoter (Clontech, Palo Alto, Calif.), and pTrc99A (4.2 kb) vector with trc promoter (Pharmacia Biotech, Uppsala, Sweden). Several operons with different combinations of relevant genes were generated as described below. Assays for propionyl-CoA transferase and acrylyl-CoA hydratase (or 3-HP dehydratase) are described in WO 02/42418 (herein incorporated by reference).

Isolation of a 3-HP Dehydrogenase Gene from *Alcaligenes faecalis* M3A

*A. faecalis* (ATCC #700596) is salt marsh bacterium that metabolizes acrylate via 3-HP.

The 3-HP produced from acrylate is likely converted to malonic semialdehyde by a 3-HP dehydrogenase. To isolate the gene encoding this dehydrogenase, *A. faecalis* genomic DNA was isolated as follows. A five-mL *A. faecalis* culture was grown at 37° C. in trypticase soy broth, and cells harvested then resuspend in 400 mL TE buffer. Subsequently, 20 mL of 10% SDS, 100 μl 10 mg/ml proteinase K, and 10 mL 100 mg/ml lysozyme were added to the cell suspension and the mixture incubated for two hours at 42° C. with occasional mixing. To this mix, 150 mL phenol was added and the mixture shaken for at least two hours at 37° C., then approximately 800 mL chloroform added. The mixture was mixed by vortexing and centrifuged for 30 minutes at 15000 rpm. The uppper aqueous phase was transferred to a clean microfuge tube, and the DNA precipitated with 60 mL 3M NaOAc and approximately 1 mL ethanol, and recovered by spooling. The DNA was resuspended with 400 mL TE buffer and 20 mL 200 mg/ml RNase added, and the mixture incubated for 1 hour at 37° C. The DNA was re-precipitated with NaOAC and ethanol, rinsed several times with 70% ethanol and resuspend in TE buffer.

The following degenerate primers were designed based on conserved regions of publicly known amino acid sequences of the 3-hydroxyisobutrate dehydrogenase genes which are expected to be homologous to the desired 3-HP dehydrogenase. AFHPDHF1: 5' TTYATYGGBYTSGGBAAYATGGG 3' (SEQ ID NO: 16); AFHPDHF2: 5' GAYGCNCCNGTB-WSSGGBGG 3' (SEQ ID NO: 17); and AFHPDHR2: 5' CATRTTRTTRCARATYTTNGC 3' (SEQ ID NO: 18). PCR reactions using *A. faecalis* genomic DNA as template were carried out using Taq DNA polymerase (Roche) according to the manufacturer's instructions, using either SEQ ID NOS: 16 and 18 (reaction A) or SEQ ID NOS: 17 and 18 (reaction B). The PCR program consisted of an initial incubation of 94° C. for 2 minutes, 4 cycles of 94° C., 30 seconds; 56° C., 45 seconds, 72° C. 3 minutes; 4 cycles of 94° C., 30 seconds; 54° C., 45 seconds, 72° C. 3 minutes; 4 cycles of 94° C., 30 seconds; 52° C., 45 seconds, 72° C. 3 minutes; 4 cycles of 94° C., 30 seconds; 50° C., 45 seconds, 72° C. 3 minutes; and 16 cycles of 94° C., 30 seconds; 47° C., 45 seconds, 72° C. 3 minutes, followed by a final incubation of 7 minutes at 72° C. Both reactions gave products of approximately 500 bp. The PCR product from reaction A was gel isolated, cloned into pCR11 and transformed into TOP10 chemical competent cells, selected on LB medium containing 50 mg/ml kanamycin. Clones having the right size insert were selected and their plasmids isolated and sequenced. Based on these sequences the following gene specific nested primers were designed: GWHPDF1: 5' GGTTTACGAGGGC-GAGAACGGCTTGCT 3' (SEQ ID NO: 19); GWHPDF2: 5'CAAGCTGGGTCTGTTCATGCTGGATG 3' (SEQ ID NO: 26); GWHPDR1: 5' AAGCGGTTCTCGCCCTCG-TAAACCTGA 3' (SEQ ID NO: 27); and GWHPDR2: 5' CGCATTCAAGTCAAAGACGTTCAGGCTA 3' (SEQ ID NO: 32) and the Genome Walk technique used to isolate the entire ORF of the gene encoding the 3-HP dehydrogenase. The sequence of this ORF is shown in SEQ ID NO: 33, and the corresponding protein sequence in SEQ ID NO: 34. The start codon of the 3-HP dehydrogenase is at position 408 of SEQ ID NO: 33 and is preceeded by a ribosome-binding site at positions 397-403 of SEQ ID NO: 33. The stop codon is at position 1304 of SEQ ID NO: 33.

Cloning, Expression, and Assay of β-alanine-CoA Ammonia Lyase (A CL)

Two acl genes were cloned from *C. propionicum*. acl-1 (SEQ ID NO: 22) encodes a 145 amino acid protein (SEQ ID NO: 23) and acl-2 (SEQ ID NO: 53) encodes a 144 amino acid protein (SEQ ID NO: 54). These two proteins are highly homologous and differ by only 8 amino acids at the C-terminus. The acl-1 and acl-2 genes were cloned using the following primers: OSaclNdeF: 5'-GGGAATTCCATATG-GTAGGTAAAAAGGTTGTACATC-3' (SEQ ID NO: 35), and OSaclBamR: 5'-CGACGGATCCATTCGTCCGCT-TGAATAACTAAAG-3' (SEQ ID NO. 36) for α-1, and SEQ ID NO: 35 and OSacl2BamR: 5'-CGACGGATC-CCGAAAATGTCACCAAAAATTATTGAG-3' (SEQ ID NO: 37) for acl-2. The resulting sequences were cloned into the pET11a vector digested with NdeI and BamHI. Resulting plasmids pACL-1 and pACL-2 were transformed into BL21 (DE3) cells. BL21(DE3) carrying pET11a (control), pACL-1 and pACL-2 were grown in 10 ml LB medium supplemented with 50 μg/ml carbenicillin to $OD_{600}$~0.5 and induced with 100 μM IPTG for 4 hours. The induced cells were collected by centrifugation at 3500 rpm in Avanti J20 centrifuge (Beckman, Fullerton, Calif.) and treated with Bug Buster (Novagen, Madison, Wis.) according to the manufacturer instruction. The resulting cell extract was used in an enzyme assay that followed the conversion of acrylyl-CoA to beta-alanine-CoA (the reverse reaction with respect to the pathway in FIG. 1).

The assay mixture contained 10 μl M TAE, 20 μl 1M $NH_4Cl$, 2 μl 100 μM acrylyl-CoA, 10 μl cell extract, and 158 μl $H_2O$. The enzymatic reaction was incubated for five minutes at 37° C. and stopped by addition of 200 μl 10% TFA. The mixture was loaded on C18 Sep-Pak Vac 1 cc column (Waters, Milford, Mass.), eluted with 200 μl 40% acetonitrile, 0.1% TFA and reduced in volume to 100 μl by centrifugation in SpeedVac (Savant Instruments, Holbrook, N.Y.). Formation of beta-alanyl-CoA was detected by LC-MS using standard methods. Both ACL-1 and ACL-2 enzymes were active and used for beta-alanine operon construction.

Cloning, Expression, and Assay of CoA Transferase from *E. coli*

The open reading frame yfdE (identified as a hypothetical protein in the PubMed database) was amplified using PCR. Because the open reading frame had two potential start sites, the following primers were used to clone and express both genes: yfdE gtg nde sen (5'AGAGAGCATAT-GTCTTTTCACCTTCGGC-3'; SEQ ID NO: 38), and yfdE atg nde sen (5'-AGAGAGGGATCCGCGGCTCCCACAAT-GTTGAAATG-3' SEQ ID NO: 39) for yfdE-1, and yfde gtg nde sen (SEQ ID NO: 38) and yfde bam anti (5'-AGAGAG-CATATGACAAATAATGAAAGCAAAGG-3', SEQ ID NO: 40) for yfdE-2.

Chromosomal DNA from *E. coli* MG1655 was used as template for PCR performed with Pfu Turbo (Stratagene) using the following PCR conditions: 94° C. for 5 minutes; 25 cycles of 94° C. for 30 seconds, 55° C. for 30 seconds, and 72° C. for 2 minutes 20 seconds, followed by incubation at 72° C. for 7 minutes. The PCR reaction was purified using QIAquick PCR purification Kit (Qiagen), digested with NdeI and BamHI, cloned into pET28b (Novagen) digested with the same restriction enzymes, and transformed into chemically competent TOP10 cells (Invitrogen). Plasmids from positive clones were isolated and transformed intoBL21(DE3) expression cells (Novagen). Cells were grown in LB media at 37° C. to an $OD_{600}$ of 0.6 and were induced with 100 μM IPTG and incubated an additional 3 hours after induction. The cells were harvested by centrifugation and washed once with 0.85% NaCl. The cell pellet was stored at −80° C. until further use. The cell pellet was thawed on ice, and resuspended in 4 ml binding buffer (Novagen HisBind purification kit). The cells were lysed by three passages through a French Pressure Cell (SLM Aminco) (10000 psi). The cell debris was removed by centrifugation (30,000×g for 30 minutes). The extract was filtered through a 0.45 μm syringe filter before loading on a Quick 900 cartridge following the manufacturer's instructions (Novagen). Purified protein was desalted using a PD-10 column (Pharmacia) according to the manufacturer's instructions. The buffer used was 5 mM boric acid, 5 mM Tris, 5 mM citric acid, 5 mM $NaH_2PO_4$ pH 7.0.

Purified protein was assayed using a reaction mix containing 100 mM K phosphate, pH 7.0, 100 mM beta-alanine, 1 mM acetyl-CoA, and 20 μl purified CoA transferase in a total assay volume of 200 μl. The reaction was incubated for 20 minutes at room temperature and then stopped with 100 μl 10% trifluroacetic acid (TFA). The reactions were purified using 1 cc SepPak Vac cartridges (Waters Milford, Mass.) conditioned with 1 ml methanol and washed twice with 1 ml 0.1% TFA. The sample was applied and the cartridge washed twice with 1 ml 0.1% TFA. The sample was eluted with 200 μl 40% acetonitrile containing 0.1% TFA, dried to ½ volume in a rotary evaporator and analyzed by liquid chromatography/mass spectrometry. A peak corresponding to the expected mass for beta-alanyl-CoA was present in assays with yfdE-1 or yfdE-2 proteins, and this peak was not present in the controls omitting the purified proteins, indicating that the CoA transferases are responsible for the synthesis of beta-alanyl-CoA.

Operons 1 and 2: ACL-propionyl-CoA transferase-Acrylyl-CoA hydratase

Operons for the following conversion: beta-alanine to beta-alanyl-CoA to acrylyl-CoA to 3-HP were constructed. A gene encoding CoA transferase was amplified from genomic DNA of *M. elsdenii* by PCR with OSNBpctF (5'-GGGAATTCCATATGAGAAAAGTAGAAATCATTACAGCTG-3'; SEQ ID NO: 41) and OSHTR (OSHTR: 5'-ACGTTGATCTCCTTCTACATTATTTTTTCAGTCCCATG-3'; SEQ ID NO: 42) primers.

A CoA hydratase gene was amplified from genomic DNA of C aurantiacus by PCR with OSTHF (5'-CATGGGACTGAAAAAATAATGTAGAAGGAGATCAACGT-3'; SEQ ID NO: 43) and OSHBR (5'-CGACGGATCCTCAACGACCACTGAAGTTGG-3'; SEQ ID NO: 44) primers.

ACL-1 and ACL-2 (beta-alanine-CoA ammonia lyase) genes were amplified from *C. propionicum* genomic DNA with primer pairs OsaclXbaF (5'-CTAGTCTAGAGCTTTCTAAGAAACGATTTCCG-3'; SEQ ID NO: 45) and OSaclNdeR (5'-GGGAATTCCATATGCGTAACTTCCTCCTGCTATCATTCACCGGGTGCTTTCT-3'; SEQ ID NO: 46) for acl-1; and OSacl2XbaF (5'-CTAGTCTAGAGGAAACCGCTTAACGAACTC-3'; SEQ ID NO: 47) and OSacl2-2NdeR (5'-GGGAATTCCATATGCGTAACTTCCTCCTGCTATTATTGAGGGTGCTTTGCATCC-3'; SEQ ID NO: 48) for acl-2.

PCR was conducted in a Perkin Elmer 2400 Thermocycler using Pfu Turbo polymerase (Stratagene) according to the manufacturer instructions. PCR was performed under the following conditions: initial denaturation step 94° C. for 2 minutes; 25 cycles of 94° C. for 30 seconds, 55° C. for 30 seconds, 72° C. for 2 minutes; final extention at 72° C. for 7 minutes. Resulting PCR products were gel purified using Qiagen Gel Extraction Kit (Qiagen, Inc.).

CoA-transferase and CoA-hydratase PCR products were assembled together in assembly PCR. OSTHF and OSHTR primers (SEQ ID NOS: 42 and 43) are complementary to each other which allowed the complementary DNA ends to anneal to each other during PCR and to extend the DNA in both directions. To ensure the efficiency of the assembly and the following amplification, two end primers OSNBpctF and OSHBR (SEQ ID NOS: 41 and 44) were added to the assembly PCR mixture containing 100 ng of the purified CoA-transferase and CoA-hydratase PCR products and the mix of rTth polymerase (Applied Biosystems, Foster City, Calif.) and Pfu Turbo polymerase (Stratagene) in a ratio of 8:1. The polymerase mix ensured higher fidelity of the PCR reaction. Assembly PCR was run under the following conditions: initial denaturation step 94° C. for 1 minute; 20 cycles of 94° C. for 30 seconds, 54° C. for 30 seconds, 68° C. for 2.5 minutes; final extention at 68° C. for 7 minutes. The assembled PCR product was gel purified as described above and digested with NdeI and BamHI. The sites for these restriction enzymes were introduced to assembled PCR product with OSNBpctF (NdeI) and OSHBR (BamHI) primers (SEQ ID NOS: 41 and 44). The digested PCR product was incubated at 80° C. for 30 minutes (to inactivate the restriction enzymes) and used directly for ligation to pET11a vector.

Vector pET11a was digested with NdeI and BamHI, gel purified using Qiagen Gel Extraction kit, treated with shrimp alkaline phosphatase as suggested by the manufacturer (Roche Molecular Biochemicals) and used for ligation with the assembled PCR product. Ligation was performed at 16° C. overnight using T4 ligase (Roche Molecular Biochemicals). The ligation mixture was transformed into chemically competent NovaBlue cells (Novagen) and plated on LB plates supplemented with 50 μg/ml carbenicillin. Individual colonies were selected for plasmid DNA purification; plasmid DNA was obtained using Qiagen Spin Miniprep Kit. Plasmids were digested with NdeI and BamHI and analyzed by gel electrophoresis.

The resulting plasmid was named pTH, digested with XbaI and NdeI, purified using gel electrophoresis and Qiagen Gel Extraction kit as described above, and used as a vector for consequent cloning of ACL-1 and ACL-2 PCR products digested with the same enzymes. The ligation was performed as described above, and the ligation mixture transformed into chemically competent NovaBlue cells as described above. Individual colonies were selected for plasmid DNA purification; plasmid DNA was obtained using Qiagen Spin Miniprep Kit. Plasmids were digested with XbaI and NdeI and analyzed by gel electrophoresis. Resulting pATH plasmids carrying the constructed operon were transformed into *E. coli* BL21(DE3) cells to determine the expression of the cloned genes.

To measure the gene expression and 3-HP production, BL21(DE3) cells carrying pATH-1 and pATH-2 plasmids were grown to $OD_{600}$~0.5 in M9CA medium (Difco Laboratories, Sparks, Mass.) supplemented with 10 g/l glucose, 5 g/l beta-alanine and 50 μg/ml carbenicillin, and induced with 100 μM IPTG underaerobic conditions. BL21(DE3) cells carrying pET11a vector served as a control. Cell samples were taken 2 and 4 hours after IPTG induction for polyacrylamide gel electrophoresis analysis. All three enzymes were expressed as shown by the appropriate sized band on the gel. Production of 3-HP from beta-alanine was detected with both operon constructs, pATH-1 and pATH-2, but not in the control cells by LC-MS analysis.

Operon 3: 4-aminobutyrate aminotransferase-3-hydroxyisobutyrate dehydrogenase In an alternative or additional pathway, beta-alanine can be deaminated by a polypeptide having beta-alanine-2-oxoglutarate aminotransferase activity to yield malonate semialdehyde, which can be further reduced to 3-HP by a polypeptide having 3-HP dehydrogenase activity or a polypeptide having 3-hydroxyisobutyrate dehydrogenase activity.

Methods for isolating, sequencing, expressing, and testing the activity of such polypeptides are described in WO 02/42418 (herein incorporated by reference). One skilled in the art will understand that similar methods can be used to obtain the sequence of any such polypeptide from any organism.

The gene encoding 4-aminobutyrate aminotransferase was amplified from genomic DNA of *C. acetobutylicum* by PCR with OsabatF (5'-CCGGAATTCTTTAATATGC-GATTTGGAGGAG-3'; SEQ ID NO: 49) and OSDATR (5'-GTCCGTCTCCCTTTCAGCTTAAATCGC-TATTCTTATAGC-3'; SEQ ID NO: 50) primers. A gene encoding 3-hydroxyisobutyrate dehydrogenase was amplified from genomic DNA of *P. aeruginosa* by PCR with OSATDF (5'-GCTATAAGAATAGCGATTTAAGCT-GAAAGGGAGACGGAC-3'; SEQ ID NO: 51) and OSibdR (5'-CGACGGATCCGCAGTGAGTGAGCCTTGGAG-3'; SEQ ID NO: 52) primers. PCR was conducted in a Perkin Elmer 2400 Thermocycler using Pfu Turbo polymerase according to the manufacturer instructions under the following conditions: initial denaturation step 94° C. for 2 minutes; 25 cycles of 94° C. for 30 seconds, 56° C. for 30 seconds, 72° C. for 1.5 minutes; final extention at 72° C. for 10 minutes. Resulting PCR products were gel purified using Qiagen Gel Extraction Kit.

PCR products of 4-aminobutyrate aminotransferase and 3-hydroxyisobutyrate dehydrogenase were assembled together in assembly PCR. The primers shown in SEQ ID NOS: 50 and 51 are complementary to each other and therefore complementary DNA ends could anneal to each other during PCR reaction and to extend the DNA in both directions. To ensure the efficiency of the assembly and the following amplification, two end primers OSabatF and OSibdR (SEQ ID NOS: 49 and 52) were added to the assembly PCR mixture containing 100 ng of the purified 4-aminobutyrate aminotransferase and 3-hydroxyisobutyrate dehydrogenase PCR products and the mix of rTth polymerase and Pfu Turbo polymerase in 8:1 ratio. Assembly PCR was run under the following conditions: initial denaturation step 94° C. for 1 minute; 25 cycles of 94° C. for 30 seconds, 55° C. for 30 seconds, 68° C. for 3 minutes; final extention at 68° C. for 7 minutes. The assembled PCR product was gel purified as described above and digested with EcoR1 and BamH1. The sites for these restriction enzymes were introduced to assembled PCR product with OSabatF (EcoR1) (SEQ ID NO: 49) and OSibdR (BamH1) (SEQ ID NO: 52) primers. The digested PCR product was heated at 80° C. for 30 minutes, gel purified using Qiagen Gel Extraction kit, and used for ligation to pPROLar.A vector.

pPROLar.A was digested with EcoR1 and BamH1, gel purified using Qiagen Gel Extraction kit, treated with shrimp alkaline phosphatase as suggested by the manufacturer and used for ligation with the assembled PCR product. The ligation was performed as described above and transformed into chemically competent TOP10 cells (Novagen) and plated on LB plates supplemented with 25 μg/ml kanamycin. Individual colonies were selected for plasmid DNA purification; plasmid DNA was obtained using Qiagen Spin Miniprep Kit. Plasmids were digested with EcoR1 and BamH1 and analyzed by gel electrophoresis. The resultant plasmid carrying the 4-aminobutyrate aminotransferase and 3-hydroxyisobutyrate dehydrogenase genes was designated pATD.

To observe gene expression and 3-HP production, TOP 10 cells carrying pATD plasmids or without plasmids (control) were grown to $OD_{600}$~0.5 in LB medium supplemented with 5 g/l glucose, 5 g/l beta-alanine and 25 μg/ml kanamycin and induced with 100 μM IPTG and 0.5% arabinose under aerobic conditions. Production of 3-HP from beta-alanine was detected with cells carrying pATD, but not in the control cells by LC-MS analysis. 3-HP was observed in cell supernatants after 6 and 24 hours of IPTG induction.

EXAMPLE 11

Synthetic Operons for 3-HP Production from Alpha-Alanine

Several operons were generated in EXAMPLE 10 which permit production of 3-HP via beta-alanine through several alternative pathways. The methods disclosed in this example expand on that, by including the disclosed alanine 2,3-aminomutase sequences disclosed herein in an operon. This allows production of 3-HP via alpha-alanine.

Operon 4: alpha-alanine aminomutase-ACL-propionyl-CoA transferase-acrylyl-CoA hydratase An operon for the conversion of alpha-alanine to beta-alanine to beta-alanyl-CoA to acrylyl-CoA to 3-HP was constructed as follows. Plasmid pLC4-7LC1 plasmid carrying alanine 2,3-aminomutase (EXAMPLE 6; SEQ ID NOS: 20 and 21) was used for the construction of pLCATH2-1. The ATH-2 operon was amplified from pATH-2 (EXAMPLE 10) with the following primers: OSacl2NotF2: 5'-AAGGAAAAAAGCGGCCGCAGATTAAAG-GAGGAATTCTCAATGG-3' (SEQ ID NO: 55) and OShydXbaR: 5'-CTAGTCTAGATCAACGACCACTGAAGT-TGG-3' (SEQ ID NO: 56). PCR was conducted as described above using the mix of rTth polymerase and Pfu Turbo polymerase in 8:1 ratio under the following conditions: initial denaturation step 94° C. for 2 minutes; 25 cycles of 94° C. for 30 seconds, 56° C. for 30 seconds, 68° C. for 2 minutes; final extention at 68° C. for 7 minutes.

The resulting PCR product was purified using Qiagen PCR Purification Kit and digested with NotI and XbaI. Digested DNA was heated at 65° C. for 30 minutes for enzyme inactivation, gel purified using Qiagen Gel Extraction Kit, and cloned into pLC4-7LC—I plasmid digested with the same enzymes. The ligation was performed at 16° C. overnight using T4 ligase. The ligation mixture was transformed into chemically competent Tuner cells (Novagen) and plated on LB plates supplemented with 25 μg/ml kanamycin. Individual colonies were selected for plasmid DNA purification; plasmid DNA was obtained using Qiagen Spin Miniprep Kit. Plasmids were digested with NotI and XbaI and analyzed by gel electrophoresis. Resulting Tuner (pLCATH2-1) cells were used to observe expression of the cloned genes and production of 3-HP from alpha-alanine and beta-alanine.

Operon 5: α-alanine aminomutase-4-aminobutyrate aminotransferase-3-hydroxyisobutyrate dehydrogenase An operon for the conversion of alpha-alanine to beta-alanine to malonic semialdehyde to 3-HP was constructed as follows. Plasmid pLC4-7LC1 (EXAMPLE 6) carrying alanine 2,3-aminomutase (EXAMPLE 6; SEQ ID NOS: 20 and 21) was used for the construction of pLCATD1. The ATD operon was amplified from pATD plasmid (EXAMPLE 10) with: OSabatNotF: 5'-AAGGAAAAAAGCGGCCGCTT-TAATATGCGATTTGGAGGAG-3' (SEQ ID NO: 57) and OsibdXbaR: 5'-CTAGTCTAGAGCAGTGAGTGAGCCT-TGGAG-3' (SEQ ID NO: 58). PCR was conducted as described above for operon 4, and the resulting PCR product purified, digested with NotI and XbaI, cloned into pLC4-7LC-1 plasmid, transformed into chemically competent Tuner cells, and individual colonies selected as described for Operon 4.

Induction of Operons and 3-HP Production To observe gene expression and 3-HP production, Tuner cells carrying pLCATH2-1, pLCATD1 plasmids or pPROLar vector (control) were grown to $OD_{600}$~0.5 in LB medium supplemented with 5 g/l glucose, 5 g/l alpha-alanine or 5 g/l beta-alanine and 25 μg/ml kanamycin and induced with 100 μM IPTG and 0.5% arabinose under aerobic conditions. Production of 3-HP from beta-alanine was detected with cells carrying pLCATH2-1 and pLCATD1, but not in the control cells by LC-MS analysis. 3-HP was observed in cell supernatants after 22 hours of induction.

Operon 6: Alanine aminomutase-beta-alanine Aminotransferase-3-hp dehydrogenase-alpha-alanine aminotreansferase An operon for the conversion of pyruvate to alpha-alanine to beta-alanine to malonic semialdehyde to 3-HP was constructed as follows. The gene encoding for alanine 2,3-aminomutase was amplified from pLC4-7LC1 by PCR with KAM10F (5'-CACACAGAATTCATTAAAGAGGAG-3'; SEQ ID NO: 59) and KAMRBATR 5'-CATAATCAAACTCAAAGTCAACCATATAAGATCTCCTCCTTACTTCATGAAGAATCCCCT CC-3'; SEQ ID NO: 60) primers. A beta-alanine aminotransferase gene was amplified from rat cDNA by PCR with KAMRBATF (5'-GGAGGGGATTCTTCATGAAGTAAGGAGGAGATCTTATATGGTTGACTTTGAGTTTGATTA TG-3'; SEQ ID NO: 61) and RBATAFDR (5'-CGTGTTACTCATTTTGTCTCCTCGTCATTTACTTGAAGTCTCGCTAAGATAC-3' (SEQ ID NO: 62) primers. 3-HP dehydrogenase was amplified from *A. faecalis* genomic DNA by PCR with RBATAFDF (5'-GTATCTTAGCAGACTTCAAGTAAATGACGAGGAGACAAAATGAGTAACACG-3'; SEQ ID NO: 63) and AFDRAATR (5'-TCATTCACCCGTGAGGCCATGAATATATCTCCTTCTTAAGCTTAGTGCTTCTGACGGTAC-3'; SEQ ID NO: 64) primers. Alpha-alanine aminotransferase gene was amplified from rat cDNA with AFDRAATF (5'-GTACCGTCAGAAGCACTAAGCTTAAGAAGGAGATATATTCATGGCCTCACGGGTGAATG A-3'; SEQ ID NO: 65) and RATGPTOR (5'-GACTAGATATCTCAGGAGTACTCATGGGTGAA-3' (SEQ ID NO: 66) primers.

PCR was conducted as described above under the following conditions: initial denaturation step of 94° C. for 2 minutes; 10 cycles of 94° C. for 30 seconds, 48° C. for 30 seconds, 72° C. for 2 minutes; 5 cycles of 94° C. for 30 seconds, 52° C. for 30 seconds, 72° C. for 2 minutes; 10 cycles of 94° C. for 30 seconds, 60° C. for 30 seconds, 72° C. for 2 minutes; final extention at 72° C. for 7 minutes. PCR products were gel purified using Qiagen Gel Extraction Kit.

PCR products of alanine 2,3-aminomutase and beta-alanine aminotransferase, as well as PCR products of 3-HP dehydrogenase and alpha-alanine aminotransferase, were assembled as pairs in two assembly PCR. Primer pairs SEQ ID NOS: 60 and 61, as well as SEQ ID NOS: 64 and 65 were complementary to each other and therefore complementary DNA ends could anneal to each other during PCR reaction and extend the DNA in both directions. To ensure the efficiency of the assembly and the following amplification, two end primers (SEQ ID NOS: 59 and 62) were added to the assembly PCR mixture containing 100 ng of two purified alanine aminomutase and beta-alanine aminotransferase PCR products and the mix of rTth polymerase and Pfu Turbo polymerase in a ratio of 8:1. Other two end primers, SEQ ID NOS: 63 and 66 were added to the assembly PCR mixture containing 100 ng of purified 3-HP dehydrogenase and alpha-alanine aminotransferase, and the mix of rTth polymerase and Pfu Turbo polymerase in a ratio of 8:1. Assembly PCR was run under the following conditions: initial denaturation step 94° C. for 2 minutes; 5 cycles of 94° C. for 30 seconds, 48° C. for 30 seconds, 68° C. for 4 minutes; 5 cycles of 94° C. for 30 seconds, 52° C. for 30 seconds, 68° C. for 4 minutes; 5 cycles of 94° C. for 30 seconds, 55° C. for 30 seconds, 68° C. for 4 minutes; 10 cycles of 94° C. for 30 seconds, 50° C. for 30 seconds, 68° C. for 4 minutes; final extention at 68° C. for 7 minutes.

A second assembly PCR was performed to combine the assembled pairs to make Operon 6 which contained all four genes. Two end primers (SEQ ID NOS: 59 and 66) were added to the PCR mixture containing 100 ng of the purified pair of alanine aminomutase/beta-alanine aminotransferase; 100 ng of the purified pair of 3-HP dehydrogenase/alpha-alanine aminotransferase, and the mix of rTth polymerase and Pfu Turbo polymerase in a ratio of 8:1. The assembly PCR was run under the following conditions: initial denaturation step 94° C. for 2 minutes; 15 cycles of 94° C. for 30 seconds, 50° C. for 30 seconds, 70° C. for 5 minutes; 10 cycles of 94° C. for 30 seconds, 55° C. for 30 seconds, 70° C. for 5 minutes; final extention at 70° C. for 7 minutes.

The assembled PCR product was gel purified as described above and digested with EcoRI and EcoRV. The sites for these restriction enzymes were introduced to assembled PCR product with SEQ ID NO: 59 (EcoRI) and SEQ ID NO: 66 (EcoRV) primers. The digested PCR product was heated at 65° C. for 30 minutes, gel purified using Qiagen Gel Extraction kit and used for ligation to pTrc99A vector digested with EcoRI and SmaI. The ligation was performed at 16° C. overnight using T4 ligase, and the mixture transformed into chemically competent Tuner cells and plated on LB plates supplemented with 50 μg/ml carbenicillin. Individual colonies were selected for plasmid DNA 0.25 purification; plasmid DNA was obtained using Qiagen Spin Miniprep Kit. Plasmids were screened by PCR with SEQ ID NOS: 59 and 66 primers and analyzed by gel electrophoresis. The resulting plasmid was named pTrcβ-ala.

Tuner(pTrcβ-ala) cells were used to determine the expression of the cloned genes and production of 3-HP from glucose, alpha-alanine and beta-alanine. Tuner(pTrc99A) were used as a control. Cells were grown to $OD_{600}$~0.5 in M9CA medium (Difco Laboratories) supplemented with 5 g/l glucose and 50 μg/ml carbenicillin; or 5 g/l glucose, 5 g/l alpha-alanine and 50 μg/ml carbenicillin; or 5 g/l glucose,5 g/1 beta-alanine and 50 μg/ml carbenicillin; and induced with 100 μM IPTG and 0.5% arabinose under aerobic conditions. Production of 3-HP from beta-alanine was detected with cells carrying pTrcβ-ala, but not in the control cells by LC-MS analysis. 3-HP was observed in cell supernatants after 22 hours of induction.

EXAMPLE 12

Production of Pantothenate from Beta-Alanine

Pantothenate can be produced from beta-alanine by a polypeptides having alpha-ketopantoate hydroxymethyltransferase (E.C. 2.1.2.11), alpha-ketopantoate reductase (E.C. 1.1.1.169), and pantothenate synthase (E.C. 6.3.2.1) activity (FIG. 3).

Using the cloning methods described in EXAMPLES 10 and 11, alpha-ketopantoate hydroxymethyltransferase (E.C. 2.1.2.11), alpha-ketopantoate reductase (E.C. 1.1.1.169), and pantothenate synthase (E.C. 6.3.2.1) polypeptides can be isolated, sequenced, expressed, and tested. One skilled in the art will understand that similar methods can be used to obtain the sequence of any such polypeptides from any organism.

EXAMPLE 13

Recombinant Expression

With publicly available enzyme cDNA and amino acid sequences, and the enzymes and sequences disclosed herein, such as alanine 2,3-aminomutase, CoA transferase, beta-alanyl-CoA ammonia lyase, 3-HP-CoA dehydratase, 4-aminobutyrate aminotransferase, beta-alanine-2-oxo-glutarate aminotransferase, 3-hydroxypropionate dehydrogenase, 3-hydroxyisobutyrate dehydrogenase, glutamate dehydrogenase, 3-HP-CoA hydrolase, 3-hydroxyisobutryl-CoA hydroiase poly hydroxyacid synthase, lipase, esterase, CoA hydrolase, alpha-ketopantoate hydroxymethyltransferase, alpha-ketopantoate reductase, pantothenate synthase, pantothenate kinase, 4'-phosphopantethenoyl-1-cysteine synthetase, 4'-phosphopantothenoylcysteine decarboxylase, ATP:4'-phosphopantetheine adenyltransferase, dephospho-CoA kinase acetylating aldehyde:NAD(+) oxidoreductase, alcohol:NAD(+) oxidoreductase, aldehyde dehydrogenase (NAD(P)+) and alcohol dehydrogenase, as well as variants, polymorphisms, mutants, fragments and fusions thereof, the expression and purification of any protein, such as an enzyme, by standard laboratory techniques is enabled. One skilled in the art will understand that enzymes and fragments thereof can be produced recombinantly in any cell or organism of interest, and purified prior to use, for example prior to production of 3-HP, pantothenate and derivatives thereof.

Methods for producing recombinant proteins are well known in the art. Therefore, the scope of this disclosure includes recombinant expression of any protein or fragment thereof, such as an enzyme. For example, see U.S. Pat. No. 5,342,764 to Johnson et al.; U.S. Pat. No. 5,846,819 to Pausch et al.; U.S. Pat. No. 5,876,969 to Fleer et al. and Sambrook et al. (*Molecular Cloning: A Laboratory Manual*, Cold Spring Harbor, N.Y., 1989, Ch. 17).

Briefly, partial, full-length, or variant cDNA sequences, which encode for a protein or peptide, can be ligated into an expression vector, such as a bacterial expression vector. Proteins and/or peptides can be produced by placing a promoter upstream of the cDNA sequence. Examples of promoters include, but are not limited to lac, trp, tac, trc, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

Vectors suitable for the production of intact native proteins include pKC30 (Shimatake and Rosenberg, 1981, *Nature* 292:128), pKK177-3 (Amann and Brosius, 1985, *Gene* 40:183) and pET-3 (Studier and Moffatt, 1986, *J. Mol. Biol.* 189:113). A DNA sequence can be transferred to other cloning vehicles, such as other plasmids, bacteriophages, cosmids, animal viruses and yeast artificial chromosomes (YACs) (Burke et al., 1987, *Science* 236:806-12). These vectors can be introduced into a variety of hosts including somatic cells, and simple or complex organisms, such as bacteria, fungi (Timberlake and Marshall, 1989, *Science* 244:1313-7). invertebrates, plants (Gasser and Fraley, 1989, *Science* 244:1293), and mammals (Pursel et al., 1989, *Science* 244:1281-8), which are rendered transgenic by the introduction of the heterologous cDNA.

For expression in mammalian cells, a cDNA sequence can be ligated to heterologous promoters, such as the simian virus SV40, promoter in the pSV2 vector (Mulligan and Berg, 1981, *Proc. Natl. Acad. Sci. USA* 78:2072-6), and introduced into cells, such as monkey COS-1 cells (Gluzman, 1981, *Cell* 23:175-82), to achieve transient or long-term expression. The stable integration of the chimeric gene construct may be maintained in mammalian cells by biochemical selection, such as neomycin (Southern and Berg, 1982, *J. Mol. Appl. Genet.* 1:327-41) and mycophoenolic acid (Mulligan and Berg, 1981, *Proc. Natl. Acad. Sci. USA* 78:2072-6).

The transfer of DNA into eukaryotic, such as human or other mammalian cells, is a conventional technique. The vectors are introduced into the recipient cells as pure DNA (transfection) by, for example, precipitation with calcium phosphate (Graham and vander Eb, 1973, Virology 52:466) strontium phosphate (Brash et al., 1987, *Mol. Cell Biol.* 7:2013), electroporation (Neumann et al., 1982, *EMBO J.* 1:841), lipofection (Feigner et al., 1987, *Proc. Natl. Acad. Sci USA* 84:7413), DEAE dextran (McCuthan et al., 1968, *J. Natl. Cancer Inst.* 41:351), microinjection (Mueller et al., 1978, *Cell* 15:579), protoplast fusion (Schafner, 1980, *Proc. Natl. Acad. Sci. USA* 77:2163-7), or pellet guns (Klein et al., 1987, *Nature* 327:70). Alternatively, the cDNA can be introduced by infection with virus vectors, for example retroviruses (Bernstein et al., 1985, *Gen. Engrg.* 7:235) such as adenoviruses (Ahmad et al., 1986, *J. Virol.* 57:267) or Herpes (Spaete et al., 1982, *Cell* 30:295).

EXAMPLE 14

Peptide Synthesis and Purification

The enzymes disclosed herein, such as alanine 2,3-aminomutase, CoA transferase, beta-alanyl-CoA ammonia lyase, 3-HP-CoA dehydratase, 4-aminobutyrate aminotransferase, beta-alanine-2-oxo-glutarate aminotransferase, 3-hydroxypropionate dehydrogenase, 3-hydroxyisobutyrate dehydrogenase, glutamate dehydrogenase, 3-HP-CoA hydrolase, 3-hydroxyisobutryl-CoA hydrolase, poly hydroxyacid synthase, lipase, esterase, CoA hydrolase, alpha-ketopantoate hydroxymethyltransferase, alpha-ketopantoate reductase, pantothenate synthase, pantothenate kinase, 4'-phosphopantethenoyl-1-cysteine synthetase, 4'-phosphopantothenoylcysteine decarboxylase, ATP:4'-phosphopantetheine adenyltransferase, dephospho-CoA kinase acetylating aldehyde:NAD(+) oxidoreductase, alcohol:NAD(+) oxidoreductase, aldehyde dehydrogenase (NAD(P)+) and alcohol dehydrogenase (and variants, fusions, polymorphisms, fragments, and mutants thereof) can be chemically synthesized by any of a number of manual or automated methods of synthesis known in the art. For example, solid phase peptide synthesis (SPPS) is carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/ hydroxybenzotriazole or 2-(1H-benzo-triazol-1-yl)-1,1,3,3-tetramethyluronium hexafluorophosphate/hydroxybenzotriazole (HBTU/HOBT), and using p-hydroxymethylphenoxymethylpolystyrene (HMP) or Sasrin resin for carboxyl-terminus acids or Rink amide resin for carboxyl-terminus amides.

Fmoc-derivatized amino acids are prepared from the appropriate precursor amino acids by tritylation and triphenylmethanol in trifluoroacetic acid, followed by Fmoc derivitization as described by Atherton et al. (*Solid Phase Peptide Synthesis*, IRL Press: Oxford, 1989).

Sasrin resin-bound peptides are cleaved using a solution of 1% TFA in dichloromethane to yield the protected peptide. Where appropriate, protected peptide precursors are cyclized between the amino- and carboxyl-termini by reaction of the amino-terminal free amine and carboxyl-terminal free acid using diphenylphosphorylazide in nascent peptides wherein the amino acid sidechains are protected.

HMP or Rink amide resin-bound products are routinely cleaved and protected sidechain-containing cyclized peptides deprotected using a solution comprised of trifluoroacetic acid (TFA), optionally also comprising water, thioanisole, and ethanedithiol, in ratios of 100:5:5:2.5, for 0.5-3 hours at RT.

Crude peptides are purified by preparative high pressure liquid chromatography (HPLC), for example using a Waters Delta-Pak C18 column and gradient elution with 0.1% TFA in water modified with acetonitrile. After column elution, acetonitrile is evaporated from the eluted fractions, which are then lyophilized. The identity of each product so produced and purified may be confirmed by fast atom bombardment mass spectroscopy (FABMS) or electrospray mass spectroscopy (ESMS).

In view of the many possible embodiments to which the principles of our disclosure may be applied, it should be recognized that the illustrated embodiments are only particular examples of the disclosure and should not be taken as a limitation on the scope of the disclosure. Rather, the scope of the disclosure is in accord with the following claims. We therefore claim as our invention all that comes within the scope and spirit of these claims.

We claim:

1. An isolated polypeptide comprising an amino acid sequence having at least 95% sequence identity to the amino acid sequence of SEQ ID NO:30 and in which the amino acid at position corresponding to position 331 of SEQ ID NO:30 is Glycine, wherein the polypeptide has alanine 2.3 aminomutase activity.

2. The polypeptide of claim 1, wherein the polypeptide comprises a mutated lysine 2,3-aminomutase amino acid sequence.

3. The polypeptide of claim 2, wherein the mutated lysine 2,3-aminomutase amino acid sequence is a mutated *Porphyromonas gingivalis* lysine 2,3-aminomutase.

4. An isolated polypeptide comprising amino acids 15-390 of SEQ ID NO: 30, wherein the polypeptide has alanine 2,3 amminomutase activity.

5. The polypeptide of claim 1, wherein the polypeptide comprises SEQ ID NO: 30.

6. The polypeptide of claim 1, wherein the polypeptide comprises one or more conservative amino acid substitutions.

7. The polypeptide of claim 1, wherein the polypeptide comprises no more than 10 conservative amino acid substitutions.

8. An isolated nucleic acid comprising a nucleic acid sequence that encodes the polypeptide of claim 1.

9. The isolated nucleic acid of claim 8 operably linked to a promoter sequence.

10. The isolated nucleic acid of claim 8, wherein the nucleic acid comprises nucleotides 55-1026 of SEQ ID NO: 29.

11. The isolated nucleic acid of claim 8, wherein the nucleic acid comprises a sequence having at least 95% identity to SEQ ID NO: 29.

12. The isolated nucleic acid of claim 11, wherein the nucleic acid sequence includes one or more substitutions which results in one or more conservative amino acid substitutions.

13. The isolated nucleic acid of claim 11, wherein the nucleic acid sequence includes one or more substitutions which results in no more than 10 conservative amino acid substitutions.

14. The isolated nucleic acid of claim 11, wherein the nucleic acid comprises SEQ ID NO: 29.

15. A vector comprising the isolated nucleic acid of claim 8.

16. A recombinant nucleic acid comprising the isolated nucleic acid of claim 8.

17. A cell transformed with the recombinant nucleic acid of claim 16.

18. An isolated transformed cell comprising at least one exogenous nucleic acid molecule, wherein the at least one exogenous nucleic acid molecule comprises a nucleic acid sequence that encodes the polypeptide of claim 1.

19. The transformed cell of claim 18, wherein the cell produces beta-alanine from alpha-alanine.

20. The cell of claim 19, wherein the cell produces 3-HP, and comprises:

beta alanine;

an enzyme comprising CoA transferase activity, thereby producing beta-alanyl-CoA from the beta-alanine;

an enzyme comprising beta-alanyl-CoA ammonia lyase activity, thereby producing acrylyl-CoA from the beta-alanyl-CoA;

an enzyme comprising 3-HP-CoA dehydratase activity, thereby producing 3-HP-CoA from the acrylyl-CoA; and an enzyme comprising CoA transferase activity, 3-HP-CoA hydrolase activity, and/or 3-hydroxyisobutryl CoA hydroase activity, to produce 3-HP from 3-HP-CoA.

21. The cell of claim 20, wherein the cell produces 1,3-propanediol and comprises:

aldehyde:NAD(+) oxidoreductase activity and alcohol: NAD(+) oxidorecluctase activity, thereby producing 1,3-propanediol from the 3-HP.

22. The cell of claim 19, wherein the cell produces pantothenate and comprises:

beta alanine; and alpha-ketopantoate hydroxymethyltransferase activity, alpha-ketopantoate reductase activity, and pantothenate synthase activity, thereby producing pantothenate from the beta-alanine.

23. The cell of claim 22, wherein the cell produces CoA and comprises:

pantothenate; and pantothenate kinase activity, 4'-phosphopantethenoyl-1-cysteine synthetase activity, 4'-phosphopantothenoyl-cysteine decarboxylase activity, ATP:4'-phosphopantetheine adenyltransferase activity, and denhospho-CoA kinase activity, thereby producing CoA from the pantothenate.

24. A method of producing a polypeptide comprising alanine 2,3-aminomutase activity, comprising culturing the cell of claim 17 under conditions that allow the cell to produce the polypeptide having alanine 2,3-aminomutase activity.

25. A transgenic plant comprising the recombinant nucleic acid of claim 8.

26. The cell of claim 19, wherein the cell produces 3-HP and comprises:

beta alanine;

an enzyme comprising 4-aminobutyrate aminotransferase activity and/or beta-alanine-2-oxoglutarate aminotransferase activity, thereby producing malonic semialdehyde from the beta-alanine; and an enzyme comprising 3-HP dehydrogenase activity and/or 3-hydroxyisobutyrate dehydrogenase activity, thereby producing 3-HP from the malonic semialdehyde.

27. The cell of claim 20, wherein the cell produces 1,3-propanediol and comprises:

an enzyme comprising acetylating aldehyde dehydrogenase (NAD(P)+) activity and an enzyme Comprising alcohol dehydrogenase activity, thereby producing 1,3-propanediol from the 3-HP.

28. The cell of claim 20, wherein the cell produces a 3-HP ester and comprises:

lipase activity or esterase activity, thereby producing 3-HP ester from the 3-HP.

29. The cell of claim 20, wherein the cell produces polymerized 3-HP and comprises:

polyhydroxyacid synthase activity, thereby producing polymerized 3-HP from the 3-HP.

30. The polypeptide of claim 1, wherein the polypeptide comprises a sequence having at least 97% sequence identity to SEQ ID NO: 30 and has alanine 2,3 aminomutase activity.

31. The polypeptide of claim 1, wherein the polypeptide comprises a sequence having at least 98% sequence identity to SEQ ID NO: 30 and has alanine 2,3 aminomutase activity.

32. The polypeptide of claim 1, wherein the polypeptide comprises a sequence having at least 99% sequence identity to SEQ ID NO: 30 and has alanine 2,3 aminomutase activity.

33. The isolated nucleic acid of claim 8, wherein the nucleic acid comprises a sequence having at least 97% identity to SEQ ID NO: 29.

34. The isolated nucleic acid of claim 8, wherein the nucleic acid comprises a sequence having at least 98% identity to SEQ ID NO: 29.

35. The isolated nucleic acid of claim 8, wherein the nucleic acid comprises a sequence having at least 99% identity to SEQ ID NO: 29.

* * * * *